US012697491B2

(12) United States Patent
Bonutti et al.

(10) Patent No.: US 12,697,491 B2
(45) Date of Patent: Aug. 4, 2026

(54) SYSTEM AND METHOD FOR AFFECTING POROSITY OF TISSUE BARRIERS, INCLUDING BLOOD BRAIN BARRIER, AND DELIVERY OF ACTIVE AGENTS

(71) Applicant: Realeve, LLC, Manalapan, FL (US)

(72) Inventors: Peter M. Bonutti, Manalapan, FL (US); Justin E. Beyers, Effingham, IL (US)

(73) Assignee: Realeve, LLC, Manalapan, FL (US)

( * ) Notice: Subject to any disclaimer, the term of this patent is extended or adjusted under 35 U.S.C. 154(b) by 0 days.

(21) Appl. No.: 19/304,548

(22) Filed: Aug. 19, 2025

(65) Prior Publication Data

US 2026/0048264 A1    Feb. 19, 2026

Related U.S. Application Data

(60) Provisional application No. 63/755,763, filed on Feb. 7, 2025, provisional application No. 63/684,560, filed on Aug. 19, 2024.

(51) Int. Cl.
  *A61N 1/36*        (2006.01)
  *A61N 1/05*        (2006.01)
(52) U.S. Cl.
  CPC ....... *A61N 1/36139* (2013.01); *A61N 1/0548* (2013.01); *A61N 1/36157* (2013.01); *A61N 1/36171* (2013.01); *A61N 1/36175* (2013.01)
(58) Field of Classification Search
  CPC .............. A61N 1/36139; A61N 1/0548; A61N 1/36157; A61N 1/36171; A61N 1/36175;
  (Continued)

(56) References Cited

U.S. PATENT DOCUMENTS 765,731 A      7/1904  Hooton et al.
6,405,079 B1   6/2002  Ansarina
        (Continued)

FOREIGN PATENT DOCUMENTS

CN      113368386 A      9/2021
CN      116930614 A     10/2023
        (Continued)

OTHER PUBLICATIONS

International Search Report and Written Opinion for for PCT Application No. PCT/US2025/042653, Oct. 16, 2025, 14 pages.
        (Continued)

*Primary Examiner* — Carl H Layno
*Assistant Examiner* — Mary Grace Schlueter
(74) *Attorney, Agent, or Firm* — Stinson LLP

(57)        ABSTRACT

Systems, devices, and methods for modulating permeability of a membrane barrier (e.g., BBB), such as by increasing and/or decreasing porosity of the membrane barrier. The membrane barrier may be modulated indirectly through neuromodulation, which may include stimulation of an upstream neural body (e.g., a ganglion) that affects, either directly or indirectly, the permeability of the membrane barrier. Modulating a membrane barrier has uses in selective delivery of active agents or other substances through the membrane barrier into tissues or cells. In some situations, these active agents or other substances would not be able to pass through the barrier without modulation. Modulating a membrane barrier has uses in selective drainage of fluid, waste, and/or byproducts from the tissue or cells from one side of the membrane barrier, or reducing the porosity of the membrane barrier to correct a leaky barrier.

20 Claims, 21 Drawing Sheets

(58) Field of Classification Search

CPC .. A61N 1/327; A61N 1/0526; A61N 1/37235;
A61N 1/3606

USPC ........................................................ 607/62

See application file for complete search history.

(56) References Cited

U.S. PATENT DOCUMENTS

| | | | |
|---|---|---|---|
| 6,429,217 | B1 | 8/2002 | Levin |
| 6,432,986 | B2 | 8/2002 | Levin |
| 6,479,523 | B1 | 11/2002 | Puskas |
| 6,491,940 | B1 | 12/2002 | Levin |
| 6,526,318 | B1 | 2/2003 | Ansarinia |
| 6,656,960 | B2 | 12/2003 | Puskas |
| 6,778,854 | B2 | 8/2004 | Puskas |
| 6,853,858 | B2 * | 2/2005 | Shalev .................. A61N 1/205 604/20 |
| 6,885,888 | B2 | 4/2005 | Rezai |
| 7,117,033 | B2 | 10/2006 | Shalev et al. |
| 7,142,910 | B2 | 11/2006 | Puskas |
| 7,310,552 | B2 | 12/2007 | Puskas |
| 7,340,299 | B2 | 3/2008 | Puskas |
| 7,477,945 | B2 | 1/2009 | Rezai et al. |
| 7,532,938 | B2 | 5/2009 | Machado et al. |
| 7,561,919 | B2 | 7/2009 | Shalev et al. |
| 7,636,597 | B2 | 12/2009 | Gross et al. |
| 7,684,859 | B2 | 3/2010 | Shalev et al. |
| 7,799,337 | B2 | 9/2010 | Levin |
| 7,860,569 | B2 | 12/2010 | Solberg et al. |
| 8,010,189 | B2 | 8/2011 | Shalev |
| 8,055,347 | B2 * | 11/2011 | Lamensdorf ....... A61N 1/36082 607/45 |
| 8,206,369 | B2 | 6/2012 | Ansarinia |
| 8,229,571 | B2 | 7/2012 | Lorian et al. |
| 8,283,793 | B2 | 10/2012 | Pless |
| 8,311,632 | B2 | 11/2012 | Pless et al. |
| 8,339,262 | B2 | 12/2012 | Pless |
| 8,355,779 | B2 | 1/2013 | Ansarinia |
| 8,394,075 | B2 | 3/2013 | Ansarinia |
| 8,406,869 | B2 | 3/2013 | Lamensdorf et al. |
| 8,412,336 | B2 | 4/2013 | Pless et al. |
| 8,473,062 | B2 | 6/2013 | Pless |
| 8,494,641 | B2 | 7/2013 | Boling et al. |
| 8,686,858 | B2 | 4/2014 | Pless |
| 8,781,574 | B2 | 7/2014 | Pless et al. |
| 8,870,773 | B2 | 10/2014 | Narouze |
| 8,954,149 | B2 | 2/2015 | Shalev |
| 8,958,881 | B2 | 2/2015 | Lamensdorf et al. |
| 8,983,609 | B2 | 3/2015 | Rezai et al. |
| 9,211,133 | B2 | 12/2015 | Papay |
| 9,220,524 | B2 | 12/2015 | Boling et al. |
| 9,233,245 | B2 | 1/2016 | Lamensdorf et al. |
| 9,320,908 | B2 | 4/2016 | Fletcher et al. |
| 9,456,836 | B2 | 10/2016 | Boling et al. |
| 9,550,057 | B2 | 1/2017 | Papay et al. |
| RE46,307 | E | 2/2017 | Ansarinia |
| RE46,332 | E | 3/2017 | Ansarinia |
| 9,604,057 | B2 | 3/2017 | Caparso |
| 9,607,195 | B2 | 3/2017 | Pless |
| 9,610,441 | B2 | 4/2017 | Goodman et al. |
| 9,662,140 | B2 | 5/2017 | Powell et al. |
| 9,700,721 | B2 | 7/2017 | Goodman et al. |
| 9,757,572 | B2 | 9/2017 | Boling et al. |
| 9,763,581 | B2 | 9/2017 | Bonutti et al. |
| 9,861,295 | B2 | 1/2018 | Powell et al. |
| 10,058,393 | B2 | 8/2018 | Bonutti et al. |
| 10,068,318 | B2 | 9/2018 | Dzyubak et al. |
| 10,098,662 | B2 | 10/2018 | Boling et al. |
| 10,286,213 | B2 | 5/2019 | Boling et al. |
| 10,322,279 | B2 | 6/2019 | Papay |
| 11,478,641 | B2 | 10/2022 | Luhrs et al. |
| 11,679,263 | B2 | 6/2023 | Hsu et al. |
| 11,687,800 | B2 | 6/2023 | Bonutti et al. |
| 11,883,665 | B2 | 1/2024 | Hsu et al. |
| 12,070,596 | B2 | 8/2024 | Smyth |
| 12,383,735 | B2 | 8/2025 | Bonutti et al. |
| 12,544,569 | B2 | 2/2026 | Bonutti et al. |
| 2002/0008723 | A1 | 1/2002 | Wen et al. |
| 2004/0015068 | A1 | 1/2004 | Shalev et al. |
| 2005/0074506 | A1 | 4/2005 | Natan et al. |
| 2005/0266099 | A1 | 12/2005 | Shalev |
| 2006/0020299 | A1 | 1/2006 | Shalev |
| 2009/0210026 | A1 | 8/2009 | Solberg et al. |
| 2009/0299418 | A1 | 12/2009 | Shalev et al. |
| 2010/0274313 | A1 | 10/2010 | Boling et al. |
| 2012/0253261 | A1 | 10/2012 | Poletto et al. |
| 2013/0184803 | A1 | 7/2013 | Altman |
| 2013/0304141 | A1 | 11/2013 | Goodman et al. |
| 2015/0174406 | A1 * | 6/2015 | Lamensdorf ....... A61N 1/36057 607/62 |
| 2016/0151646 | A1 | 6/2016 | Bonutti et al. |
| 2019/0336073 | A1 | 11/2019 | Kirkup et al. |
| 2021/0178154 | A1 | 6/2021 | Bonutti et al. |
| 2021/0401507 | A1 | 12/2021 | Stylos et al. |
| 2022/0101999 | A1 | 3/2022 | Bonutti et al. |
| 2023/0233858 | A1 * | 7/2023 | Minar ................ A61N 1/36157 607/50 |
| 2024/0065550 | A1 | 2/2024 | Conner |
| 2024/0359005 | A1 | 10/2024 | Bonutti et al. |

FOREIGN PATENT DOCUMENTS

| | | |
|---|---|---|
| WO | 2004010923 A2 | 2/2004 |
| WO | 2025106975 A1 | 5/2025 |

OTHER PUBLICATIONS

Alahmari, A., Blood-Brain Barrier Overview: Structural and Functional Correlation, Hindawi Neural Plasticity vol. 2021, Article ID 6564585, Dec. 6, 2021, 10 pages, https://doi.org/10.1155/2021/6564585.

Bornstein, MD, et al., Sphenopalatine Ganglion Stimulation to Augment Cerebral Blood Flow a Randomized, Sham-Controlled Trail vol. 50, No. 8, May 23, 2019, 17 pages, Stroke https://doi.org/10.1161/STROKEAHA.118.024582.

Biose et al., Promising Cerebral Blood Flow Enhancers in Acute Ischemic Stroke, Transl. Stroke Res., vol. 14, pp. 863-889, (2023) Nov. 17, 2022, https://doi.org/10.1007/s12975-022-01100-w.

Feigin et al., World Stroke Organization (WSO): Global Stroke Fact Sheet 2022, International Journal of Stroke, Jan. 5, 2022, pp. 18-29, vol. 17—Issue 1, World Stroke Organization.

Goadsby Md, P., et al., Safety and Efficacy of sphenopalatine ganglion stimulation for chronic cluster headache: a double-blind, randomized controlled trial, Lancet Neurology, Dec. 2019, pp. 1081-1090, vol. 18, Issue 12, Elsevier Ltd.

Hosseini et al, Mechanisms of action of acute and subacute sphenopalatine ganglion stimulation for ischemic stroke, International Journal of Stroke, Apr. 23, 2020, vol. 15(8) 839-848, https://journals.sagepub.com/doi/10.1177/1747493020920739.

Khurana et al. Implant for Augmentation of Cerebral Blood Flow Trial-1 (ImpACT-1). A single-arm feasibility study evaluating the safety and potential benefit of the Ischemic Stroke System for treatment of acute ischemic stroke, Jul. 3, 2019, 14 pages, https://doi.org/10.1371/journal.pone.0217472.

Lang, Md et al., 155 Enhanced Stem Cell Delivery by Functional Blood-Brain Barrier Modulation Improves Neurological Recovery in a Rodent Stroke Model, Neurosurgery, vol. 63, pp. 162-163, Aug. 2016, https://doi.org/10.1227/01.neu.0000489724.69358.b7.

Levi et al., Stimulation of the Sphenopalatine Ganglion Induces Reperfusion and Blood-Brain Barrier Protection in the Photothrombotic Stroke, Jun. 22, 2012, 10 pages, https://doi.org/10.1371/journal.pone.0039636.

Mordor Intelligence, Neurodegenerative Disease Market Size & Share Analysis—Growth Trends & Forecasts (2024-2029) 7 pp. Jan. 29, 2024, https://www.mordorintelligence.com/industry-reports/neurodegenerative-disease-marke.

Powell et al., The Potential Role of Neuromodulation in Subarachnoid Hemorrhage, Neuromodulation: Technology at the Neural Interface, Dec. 2, 2022, pp. 1215-1226, vol. 25—Issue 8, Elsevier Inc.

(56)                    References Cited

OTHER PUBLICATIONS

Puris, E. et al., Targeting Transporter for Drug Delivery to the Brain: Can we do Better?, Mar. 31, 2022, 41 pages, Pharmaceutical Research (2002) 39:1415-1455.

Saver, Md, et al., Refined Sphenopalatine Ganglion Stimulator Placement and Intensity Setting to Augment Blood Flow and Neurologic Function, Stroke, vol. 50, No. 12, Nov. 19, 2019, https://doi. org/10.1161/ STROKEAHA.119.027177.

Schmidt et al., Sphenopalatine Ganglion Stimulation is a Reversible and Frequency-Dependent Modulator of the Blood-Brain Barrier, Apr. 26, 2019, Brain Research 1718, pp. 231-241, https://doi.org/10.1016/j.brainres.2019.04.030.

Schoenen et al., Stimulation of the Sphenopalatine ganglion (SPG) for cluster headache treatment. Pathway CH 1: a randomized sham-controlled study, Cephalalia an International Journal of Headache, vol. 33, Issue 10, pp. 816-830, Jul. 10, 2013, https://doi.org/10.1177/0333102412473667.

Stamatovic et al., Junctional proteins of the blood-brain barrier: New insights into function and dysfunction, Jan., Feb., Mar. 2016, 12 pages, Taylor & Francis Group, LLC.

Stricsek Md et al., 221 Functional Modulation of the Blood Brain Barrier, Neurosurgery, vol. 64, Issue CN suppl. 1, p. 260, Sep. 1, 2017, https://doi.org/10.1093/neuros/nyx417.221.

Stroke Management Market Poised to Surge from $36.94 Billion to $39.00 Billion in 2024, Jan. 28, 2028, https://finance.yahoo.com/news/stroke-management-market-poised-surge-005600586.html, Research and Markets, Dublin.

Tamayo et al., Regulation of Blood Flow in the Cerebral Posterior Circulation by Parasympathetic Nerve Fibers: Physiological Background and Possible Clinical Implications in Patients with Vertebrobasilar Stroke, Front. Neurol., Stroke, vol. 12, Oct. 29, 2021, https://doi.org/10.3389/fneur.2021.660373.

Tepper et al., Acute Treatment of Intractable Migraine with Sphenopalatine Ganglion Electrical Stimulation, Jul. 6, 2009, American Headache Society, https://doi.org/10.1111/j.1526-4610.2009.01451.x.

Theofanis, Md, et al. Sphenopalatine Ganglion Stimulation Upregulates Transport of Intra-Arterial Temozolomide Across the Blood-Brain Barrier, Neurosurgery, 66(Supplement_1):p. 310-151, Sep. 2019, https://doi.org/10.1093/neuros/nyz310_151.

Thiel et al., Forumm Mini-Review, Nitric Oxide and Blood-Brain Barrier Integrity, Antioxidants & Redox Signaling, vol. 3, No. 2, pp. 273-278, (2001), Mary Ann Liebert, Inc.

Yarnitsky, et al., Blood-brain barrier opened by stimulation of the parasympathetic sphenopalatine ganglion: a new method for macromolecule delivery to the brain, J Neurosurg. 101:303-309, Aug. 2004.

Yarnitsky et al., Increased BBB permeability by parasympathetic sphenopalatine ganglion stimulation in dogs—ScienceDirect, Brain Research, vol. 1018, Issue 2, pp. 236-240, Aug. 27, 2024.

* cited by examiner

FIG. 9
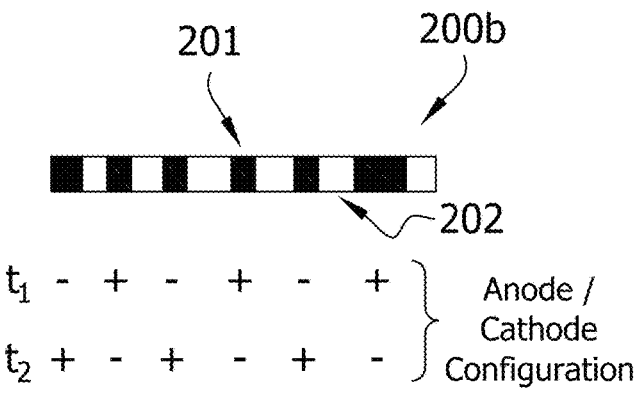
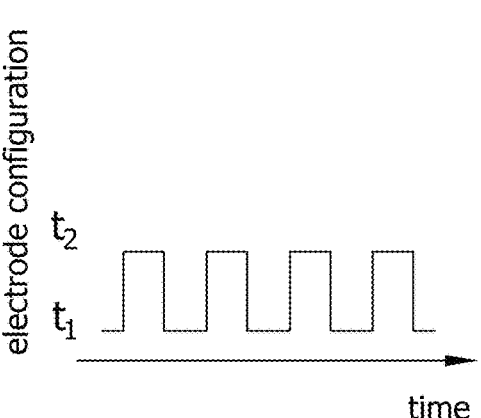
FIG. 10
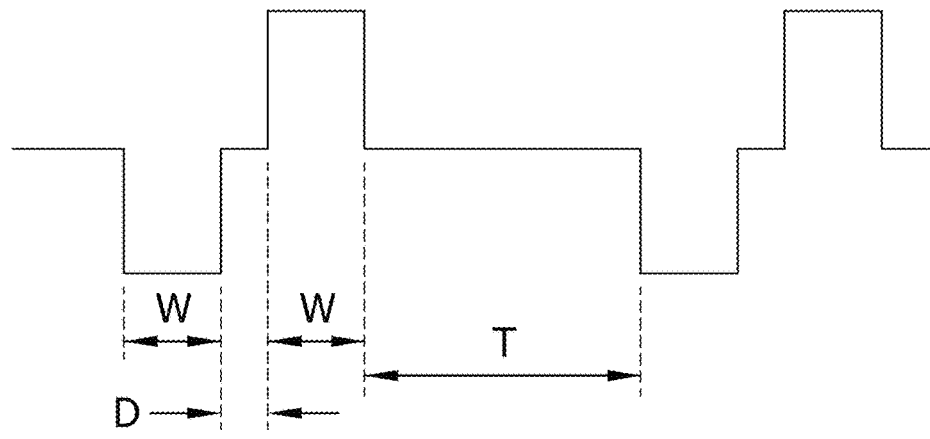
W = pulse width
D = inter phase interval
T = inter pulse interval Amplitude Modulated
Biphasic Waveform Frequency modulated
pulse width Frequency modulated
inter pulse interval

FIG. 15
:Stand Alone Operation
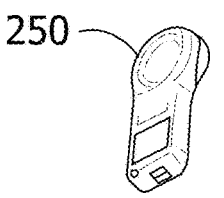
250
FIG. 16
:Tethered Operation
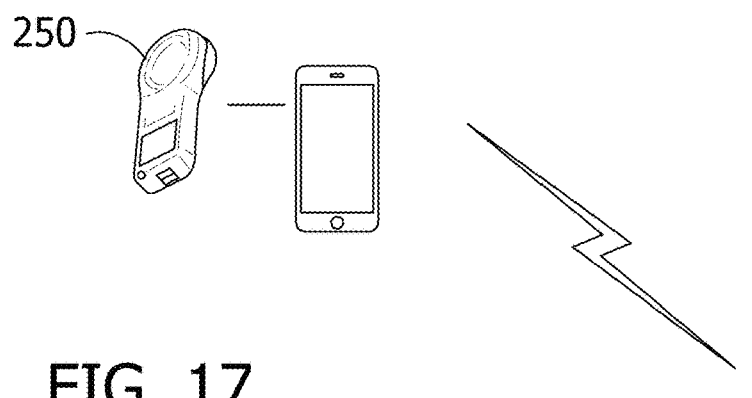
250
FIG. 17
:Wireless Operation
(Passthrough)
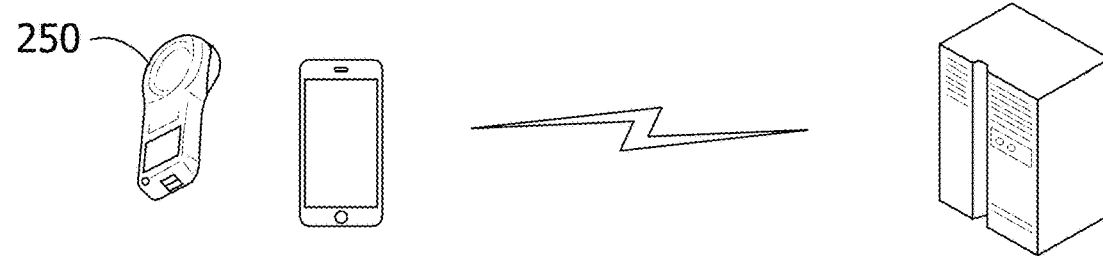
250
FIG. 18
:IOT Operation
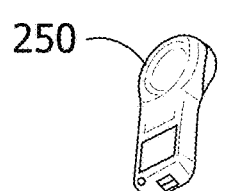
250
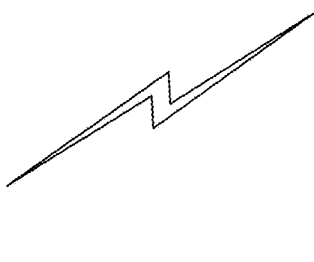

18    19

400

400b

401

402

401

402

500

500b

501

502

501

502

SYSTEM AND METHOD FOR AFFECTING POROSITY OF TISSUE BARRIERS, INCLUDING BLOOD BRAIN BARRIER, AND DELIVERY OF ACTIVE AGENTS

CROSS-REFERENCE TO RELATED APPLICATIONS

The present application claims priority to U.S. Provisional Application Ser. No. 63/684,560, filed Aug. 19, 2024, and U.S. Provisional Application Ser. No. 63/755,763, filed Feb. 7, 2025, the entirety of each of which is incorporated by reference herein.

FIELD OF THE DISCLOSURE

The present disclosure generally relates to a method and system for using devices and/or methods (e.g., stimulation) to open and/or close a tissue barrier (e.g., the blood-brain barrier) to enable delivery of a drug (i.e., an active agent) to a patient's tissue (e.g., brain tissue) and/or drainage or removal of biologicals (e.g., blood) and/or waste.

BACKGROUND OF THE DISCLOSURE

The body includes tissue barriers, such as blood vessels, membranes, other tissues, to limit transport of particles across the barrier to other cells or tissues. For example, the blood-brain barrier (BBB) is a highly specialized and selectively permeable membrane that separates the circulating blood from the brain tissue. It is formed by a layer of tightly packed endothelial cells that line the capillaries in the brain. These endothelial cells are bound together by tight junctions and surrounded by pericytes, astrocytes, and basement membrane, which provide structural support to the BBB. The BBB also contains efflux pumps that actively remove unwanted substances, including potential drugs, from the brain back into the blood stream.

The BBB plays a crucial role in maintaining a stable environment for the brain by regulating the passage of substances between the bloodstream and the brain tissue. It allows the passage of essential nutrients such as glucose and oxygen while restricting the entry of harmful substances such as toxins and pathogens. This selective permeability is achieved through several mechanisms, including active transport, receptor-mediated transport, and enzymatic degradation.

The BBB also helps to protect the brain from fluctuations in the levels of hormones, neurotransmitters, and other chemicals in the bloodstream. It also prevents the entry of large molecules such as proteins and immune cells, which can trigger inflammation and damage the brain tissue.

However, the BBB can also pose a challenge in the treatment of neurological disorders, as it can limit the delivery of drugs to the brain (e.g., by either the permeability of the BBB or by enzymes present in the BBB environment that may breakdown the drugs before entering the brain tissue). Researchers are exploring various strategies to overcome this barrier, such as using nanoparticles or modifying the properties of the drugs to enable them to cross the BBB.

Other barrier membranes may also pose a challenge to the delivery of active agents to targeted tissue and cells.

SUMMARY OF THE DISCLOSURE

The present disclosure is generally directed to systems, devices, and methods for modulating permeability of a membrane barrier (e.g., BBB), such as by increasing and/or decreasing porosity of the membrane barrier. The membrane barrier may be modulated indirectly through neuromodulation, which may include stimulation of an upstream neural body (e.g., a ganglion) that affects, either directly or indirectly, the permeability of the membrane barrier. Modulating a membrane barrier has uses in selective delivery of active agents or other substances through the membrane barrier into tissues or cells. In some situations, these active agents or other substances would not be able to pass through the barrier without modulation. Modulating a membrane barrier has uses in selective drainage of fluid, waste, and/or byproducts from the tissue or cells from one side of the membrane barrier. Other features of the systems, devices, and methods are described herein.

BRIEF DESCRIPTION OF DRAWINGS

FIG. 9 is an exemplary electrode including an electrode configuration.

FIG. 10 is a biphasic waveform.

FIG. 15 is a standalone, handheld device for operating the stimulator.

FIG. 16 is the handheld device tethered to and in electrical communication with a smart mobile device.

FIG. 17 is the handheld device in wireless communication with a smart mobile device.

FIG. 18 is the handheld device in direct communication with a remote server.

FIG. 21 is a perspective of a drug dispersion member from the '710 application.

DETAILED DESCRIPTION OF THE DISCLOSURE

Figure 1:
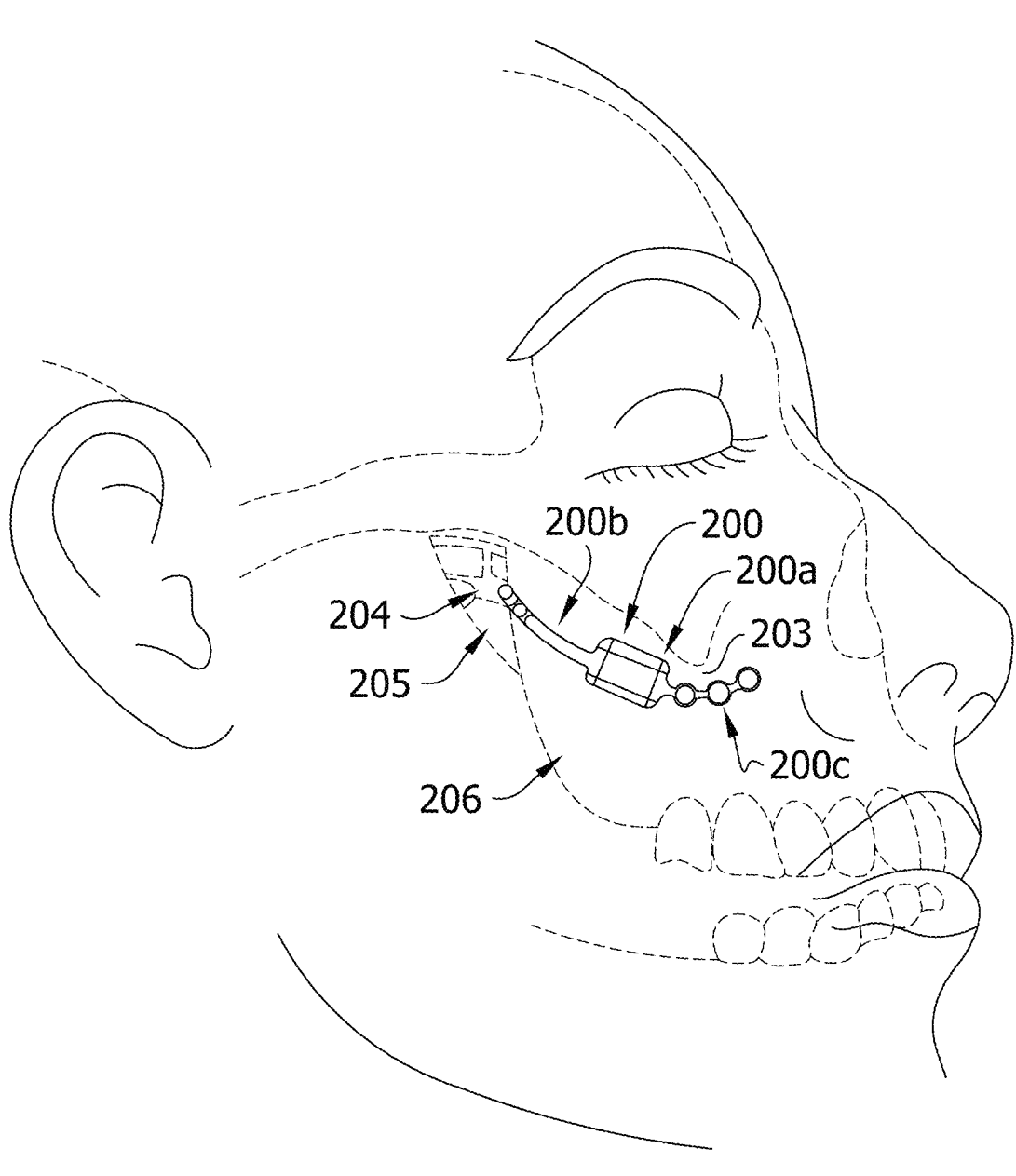
FIG. 1 is a schematic representation of one embodiment of a stimulator or electrode assembly implanted extracranially in a human body.
Figure 1A:
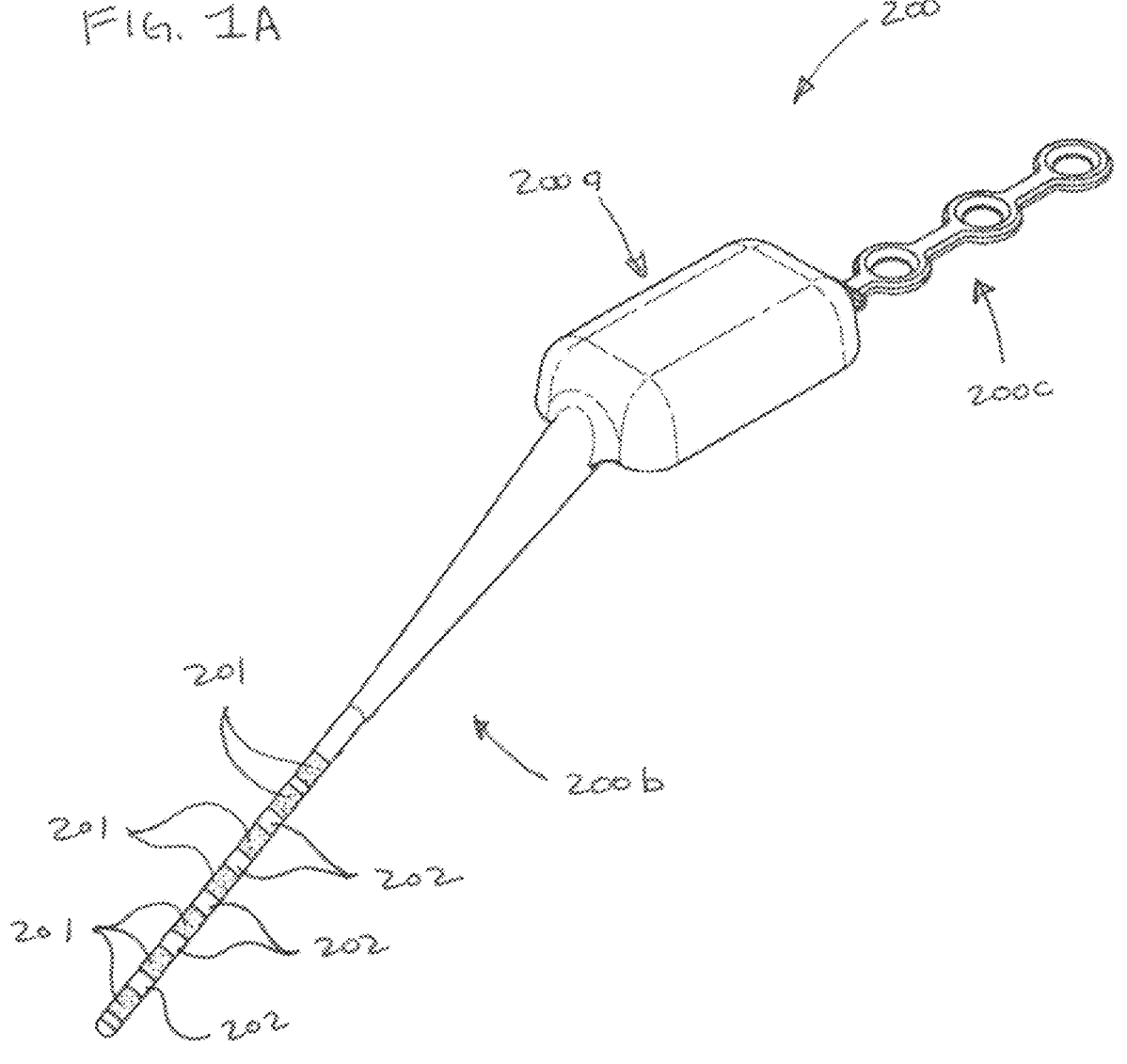
FIG. 1A is an enlarged perspective of the electrode assembly.

The following description sets forth exemplary aspects of the present disclosure. It should be recognized, however, that such description is not intended as a limitation on the scope of the present disclosure. Rather, the description also encompasses combinations and modifications to those exemplary aspects described herein.

In one embodiment, a method of delivering one or more active agents (e.g., medicine, drugs, other agents) through the blood-brain barrier (BBB) and into brain tissue is described. Stimulation, such as electrical stimulation, ultrasound, or other stimulation or energy, is used to affect porosity of the BBB (e.g., increase porosity of larger molecules or types of molecules) to enable the active agent to cross into brain tissue (i.e., increasing porosity of BBB increases its permeability). In other embodiments, a system and method includes stimulation used to affect porosity (i.e., increase porosity) of other barrier membranes of the body (e.g., bursae wall, synovial membrane, blood vessels, etc.) and delivery of one or more active agents through the barrier membrane after stimulation and into tissue or space enclosed or surrounded by the barrier membrane (i.e., increasing porosity increases permeability). Although stimulation devices are discussed herein, it will be understood that, in one or more embodiments, other neuromodulation device or external device for neuromodulation which enables an active agent to cross a barrier membrane and into brain tissue may be used in place of or as a complement to the discussed stimulation neuromodulation devices.

In one embodiment, the systems and methods described herein may be configured to increase porosity of the barrier or barrier membrane (e.g., BBB) during a first step to enable delivery of the active agent through the barrier (i.e., increase permeability), and then during a subsequent second step after a predetermined or other parameter, decrease the porosity of the barrier to inhibit other molecules and/or additional amounts of active agent from passing through the barrier (i.e., decrease permeability). Broadly, the systems and methods may "open" the barrier and then subsequently "close" the barrier upon a determining a predetermined parameter, such as time or active agent concentration in the tissue. As used herein, to "open" the barrier (and other "open" iterations) means increasing the overall porosity and/or the selective porosity of types or sizes of molecules to enable selective molecule parameters to pass through the barrier; and to "close" the barrier (and other "close" iterations) means decreasing the overall porosity and/or the selective porosity of types or sizes of molecules to inhibit selective molecule parameters from passing through the barrier.

In another embodiment, systems and methods described herein may be used to open (increase porosity of) the barrier (and optional close) without the use of one or more active agents to increase function of the barrier. For example, systems and methods may be used to facilitate stroke rehabilitation.

In another embodiment, systems and method described herein may be used to decrease the porosity of the barrier (e.g., decrease natural porosity of membrane barrier) with or without the use of one or more active agents. For example, certain conditions, such as a stroke, can cause the BBB to become leaky and not function as it should in prohibiting materials (active agents, molecules, chemicals, other substances, etc.) from passing through the BBB into the brain or from passing through the BBB and out of the brain.

In another embodiment, the stimulator implant can be used arterially or percutaneously. The lead or electrode portion of the implant can also be designed such that components or the entire system is biodegradable. Relevant disclosure for biodegradable components is disclosed in U.S. Ser. No. 11/123,497, filed May 5, 2005, the entirety of which is hereby incorporated by reference.

In one embodiment, a neuromodulation system may comprise several integrated components working in coordination to deliver precise stimulation parameters. An electrode assembly may be configured with specialized surface modifications to optimize charge injection efficiency and reduce impedance at target frequency ranges. The electrode may be composed of biocompatible conductive materials such as platinum, iridium oxide, or titanium nitride, selected for their high charge-injection capacity and stability in neural environments. Surface texturing of the electrode may be achieved through various methods including microfabrication, plasma etching, electrochemical deposition, or abrasive treatments to create roughened surfaces that enhance electrochemical surface area and improve ionic conduction. Enhanced charge injection efficiency may allow for reduced voltage levels while maintaining therapeutic current delivery, thereby minimizing tissue heating and preventing thermal damage to adjacent anatomical structures.

In yet another embodiment, a wireless power transfer system may provide energy to the implanted components without the need for percutaneous connections or frequent battery replacements. The power system may utilize either a single large inductive coil or an array of smaller overlapping coils that can be selectively energized to optimize power transfer efficiency. In configurations using multiple coils, the system may perform handshaking protocols to identify which coil provides the most efficient energy coupling to the implanted stimulator, thereby reducing power consumption and minimizing tissue heating effects.

In another embodiment, artificial intelligence (AI) and machine learning (ML) capabilities may be integrated at multiple levels within the system architecture to provide personalized treatment optimization and closed-loop control. AI functionality may be implemented at the implant level using technologies such as tinyML on application-specific integrated circuits, enabling ultra-low latency real-time adjustments and closed-loop control of stimulation parameters. Machine learning algorithms may analyze physiological inputs including heart rate variability, blood pressure, electroencephalography signals, or other biometric feedback to dynamically adjust stimulation parameters based on individual patient responses. The AI system may also classify bioresponses such as blinking, tearing, or other reflexive actions to confirm sphenopalatine ganglion activation and optimize electrode configuration in multi-electrode systems. Personalized treatment parameters may be achieved through AI-driven optimization that adapts stimulation protocols based on individual patient physiology and treatment response patterns.

In another embodiment, a body of the electrode assembly may be constructed from biocompatible ceramic materials that provide hermetic sealing while allowing transmission of inductive power and radio frequency signals. Various ceramic materials may be employed including alumina, sapphire, yttria-stabilized zirconia, silicon nitride, glass-ceramics, aluminum nitride, barium titanate, fused silica, or hydroxyapatite, selected for their biocompatibility, non-conductive properties, and radio-frequency transparency. Feedthrough pins connecting internal electronics to external electrodes may be brazed or formed in place during ceramic body creation to maintain hermetic integrity. An overmold of biocompatible polymer material may encapsulate the ceramic body, with suitable materials including silicone, polyether block amide, thermoplastic polyurethane, polyether urethane, silicone-polyurethane copolymers, or other elastomeric materials.

In yet another embodiment, stimulation waveforms may be optimized for BBB modulation using charge-balanced biphasic pulses in frequency ranges of approximately 10-100 Hz to prevent irreversible electrochemical reactions while achieving desired permeability changes. The system may accommodate various electrode configurations including cylindrical, oval, or single-sided geometries to conform to anatomical variations of the sphenopalatine ganglion region. Manufacturing techniques such as injection molding, reaction injection molding, or liquid injection molding may be employed to create electrode leads with integrated polymer insulation and embedded conductor wires.

In another embodiment, the system may also incorporate minimally invasive surgical approaches that reduce infection risk and improve cosmetic outcomes compared to traditional oral cavity access methods.

In yet another embodiment, systems and methods described herein may be used to open (and then close) the BBB to enable larger molecules to exit the brain for diagnostic purposes. For example, the BBB may be opened, such as using a method described herein, whereby larger molecules that are typically tested for using a spinal tap may enter the blood stream and can be detected by withdrawing blood from blood stream rather than the spinal tap. Opening (and subsequent closing) of the BBB or other membrane may also be used for drainage purposes (e.g. drainage of cerebrospinal fluid (CSF)).

In one exemplary method, the active agent may be delivered adjacent or to the BBB via a catheter or other means. The suitable stimulation is applied (before, after or simultaneously with delivery of the active agent) to increase and/or later the porosity of the BBB to enable the active agent to pass through the BBB into brain tissue (i.e., increase permeability). In one example, an indwelling catheter or other delivery device can controllably release the active agent. This device may be controlled by a controller (microprocessor and memory) and operated in conjunction with an indwelling stimulation device suitable to deliver stimulation for affecting the BBB to enable delivery of the active agent into brain tissue. Such agent-delivery and stimulation devices are described in more detail below. The method may be used with oxygen therapy (such as, hyperbaric oxygen therapy—in a chamber) or used as adjunct to chamber or medication, or thermal therapy to open BBB or to relieve vasospasm or transcutaneous delivery of medication or treatment.

In one or more embodiments, the active agent described herein crosses the BBB and is delivered to the cerebrospinal fluid. In certain embodiments, the active agent concentration in the cerebrospinal fluid is a higher concentration when delivered in combination with BBB stimulation, as described herein, compared to the same active agent delivered without BBB stimulation. For example, animal models show Temozolomide, a cancer drug for glioblastoma, achieves a five times higher concentration in the cerebrospinal fluid when delivered according to the methods and systems described herein (e.g., in conjunction with BBB stimulation), compared to previous Temozolomide delivery methods (e.g., without BBB stimulation).

The previous forms of delivering of an active agent to the BBB included opening an approximately 1 cm area of the BBB. This method was not portable or capable of repeated use. The previous method generally damaged the BBB and required between about 24 to 72 hours to close the opening. In contrast, active agent delivery with BBB stimulation by any of the methods disclosed herein is scalable and portable such that the active agent may be delivered to the patient anywhere.

In certain embodiments, the BBB stimulation allows for both permeability in and out of the brain. The drainage out of the brain allows large molecules and/or the active agent byproducts to exit the brain, which decreases side effects and/or permanent concentration of the byproducts in the brain compared to alternative forms of delivering active agents to the brain. Failure for the BBB or lymphatic system to properly drain fluid (normal pressure hydrocephalus) may cause an excess buildup of proteins, or amyloid which may cause death of tissue or myelin build up that can also cause further damage. Such buildup is known to cause Alzheimer's disease, stroke, Cerebral Palsy, or even multiple sclerosis (MS). This drainage using stimulation may be used in combination an implantable cerebrospinal fluid (CSF) pump. The CSF pump comprises of a pump, a reservoir, and a catheter that are implanted under the skin, usually in the abdomen, with the catheter placed in the intrathecal space (around the spinal cord) or the ventricles of the brain. The CSF pump may be used in combination with the drainage through stimulation (e.g., neurostimulation of the SPG) to enhance drainage of toxic degradation products, for example, from brain tissue. Moreover, the CSF pump, or a similarly designed pump, may be placed outside the BBB to collect the drained byproducts exiting from the opened BBB.

In certain embodiments, the delivery methods described herein uses the body's own autonomic system SPG to control BBB permeability and vasodilation as well as closing down permeability of the BBB on demand. The control of SPG and autonomic system may be further used to create liquid biopsy of the brain. In certain embodiment, the control of SPG and autonomic system may, also, modulate the permeability in peripheral vascular system.

One aspect of the present disclosure improves delivery of an active agent by lowering the concentration of the drug required to be delivered. This improved delivery may result in more cost effective treatments, less side effects experienced by the patent, and/or a less frequent dosage schedule. The systems and methods described herein may also be scalable and portable such that controlled opening and closing of the BBB and delivery of an active agent to the BBB may even be accomplished at home (i.e. outside of the clinical context).

In one or more embodiments, which may be applied to any other embodiments described herein, the active agent selected for passing through the BBB may include, but is not limited to, one or more of: drugs for Alzheimer's, chemotherapy agents, amyloid deposit removal agents, agents to enhance biologic byproduct reduction, stimulants or depressors, proteins, enzymes, hormones, other agents to enhance drainage of toxic or harmful compounds. Among other functions, active agent(s) may be used for stroke, cancer, Alzheimer's, depression, stress, sleep, psychosis, infection, vision, memory, delivery of DNA or RNA fragments with or without virus or other carrier for genetic disease, condition treatment, enhancement of brain function, atypical facial pain, cranial nerve or other pain or disease.

In one embodiment, the active agent may be selected for treatment of glioblastomas. For example, active agents selected from the group consisting of Temozolomide, Carmustine, Bevacizumab, Lomustine, and combinations thereof. Carmustine has been found to cross the BBB and achieve cerebrospinal fluid levels of >50 of blood plasma %. Bevacizumab has a high molecular weight that may limit BBB penetration, but has been found to be successful in treating some brain tumors when BBB penetration is achieved. Lomustine generally crosses the BBB well and its efficiency may be improved by the described methods (e.g., stimulation).

In some embodiments, the active agent delivered through the BBB is a medication used to treat Central Nervous System (CNS) diseases/disorders. CNS disease typically impact the brain and spinal cord. For example, CNS disease may be selected from the group consisting of Alzheimer's disease, Parkinson's disease, multiple sclerosis, Amyotrophic Lateral Sclerosis (ALS), epilepsy, stroke, meningitis, encephalitis, Huntington's disease, Cerebral Palsy, brain tumors, spinal cord injury, autism spectrum disorders, traumatic brain injury (TBI), neurodegenerative diseases, dementia, nerve injuries, peripheral neuropathy, vasospasm, hypertension, asthma, arrhythmia, anxiety, memory loss, CTE, or combinations thereof. Vasospasms are of particular scientific interest as approximately 30-70% of stroke patients experience vasospasms. In other embodiments, the CNS disease may be dysautonomia or other conditions which cause the autonomic nervous system to function improperly. The autonomic nervous system is a component of the peripheral nervous system that regulates involuntary physiologic processes including heart rate, blood pressure, respiration, digestion, and sexual arousal.

In other embodiments, the active agent may be used to treat a number of conditions affecting the CNS and may be selected from classifications selected from the group consisting of antidepressants, antipsychotics, anxiolytics, mood stabilizers, stimulants, antiepileptic drugs (AEDs), Parkinson's disease medications, migraine medications, narcotics/opioids, muscle relaxants, or combinations thereof.

In some embodiments, the active agent delivered through the BBB is a medication that is used to treat genetic diseases that, among other things, affect the CNS. For example, the genetic diseases may be selected from the group consisting of Huntington's disease, spinocerebellar ataxia, Duchenne muscular dystrophy, fragile X syndrome, neurofibromatosis Type 1, neurofibromatosis Type 2, tuberous sclerosis, Wilson's disease, ataxia-telangiectasia, spinal muscular atrophy, Charcot-Marie-Tooth disease, phenylketonuria (PKU), retinitis pigmentosa, batten disease, cystic fibrosis (with CNS implications), metachromatic leukodystrophy, or combinations thereof. Any of the above genetic disease may comprise various genetic mutations. These genetic mutations may be further treated using stem cells, viral therapy with Gene Editing, mitochondria or lysosome infusions, protein insertions, or combinations thereof (as discussed in further detail herein). There treatments may be localized or repeated over the lifetime of treatment.

In some embodiments, the active agent may be used to treat Alzheimer's disease by, among other things, managing plaque. For example, with an enhanced BBB opening it may be possible to remove plaque to achieve a lower concentration, with less frequent applications, while also allowing draining of plaque byproducts. Active agents that may be used to treat Alzheimer's disease may include, for example, active agents selected from the group consisting of Donepezil, Rivastigmine, Galantamine, Memantine, Aducanumab, Lecanemab, gantenerumab, sodium oxybate or combinations thereof. In still further embodiments, active agents that may be used to treat Alzheimer's disease may include any cognitive enhancer which improves memory and/or cognitive functions.

Donepezil may be used in certain embodiments to treat all stages of Alzheimer's disease, to improve cognitive function, and/or to slow decline. Donepezil is a cholinesterase inhibitor which shows promise for long-term effects on memory. Donepezil may be sold under the tradename Aricept, manufactured by Pfizer. Rivastigmine may be used in certain embodiments to treat mild to moderate Alzheimer's and may be sold under the tradename Exelon, manufactured by PECO Energy Company. Galantamine may be used in certain embodiments to treat mild to moderate Alzheimer's disease and may be sold under the tradename Razadyne, manufactured by Janssen Pharm. Memantine may be used in certain embodiments to treat moderate to severe Alzheimer's disease. Memantine is an NMDA receptor antagonis, which shows promise in memory and cognitive function. Memantine may be sold under the tradename Namenda. Aducanumab may be used in certain embodiments to treat early Alzheimer's disease by, among other things, targeting amyloid-beta plaques in the brain and may be sold under the tradename Aduhelm, manufactured by Biogen. Lecanemab may be used in certain embodiments to treat early Alzheimer's disease by, among other things, targeting amyloid pathology and may be sold under the tradename Leqembi, manufactured by Eisai. Gantenerumab is a monoclonal antibody targets amyloid beta. Sodium oxybate may improve cognitive functioning and memory.

In some embodiments, the active agent may be an antidepressant selected from the group consisting of selective serotonin reuptake inhibitors (SSRIs), serotonin-norephinephrine reuptake inhibitors (SNRIs), tricyclic antidepressants (TCAs), and combinations thereof. In certain embodiments, SSRIs may be selected from the group consisting of fluoxetine, sertraline, or combinations thereof. Floxetine may be sold under the tradename Prozac, manufactured by Eli Lily and Co. Sertraline may be sold under the tradename Zoloft, manufactured by Pfizer Inc. In some embodiments, SNRIs may be selected from the group consisting of venlafaxine, duloxetine, or combinations thereof. Venlafaxine may be sold under the tradename Effexor, manufactured by Wyeth Pharmaceuticals Inc. Duloxetine may be sold under the tradename Cymbalta, manufactured by Eli Lily and Company. In other embodiments, TCAs may be selected from the group consisting of amitriptyline, nortriptyline, or combinations thereof. Nortriptyline may be sold under the tradename Pamelor, manufactured by Mallinckrodt Pharmaceuticals.

In one embodiment, the active agent may be an antipsychotic selected from the group consisting of atypical antipsychotics, typical antipsychotics, or combinations thereof. Atypical antipsychotics may be selected, for example, from the group consisting of risperidone, quetiapine, or combinations thereof. Risperidone may be sold under the tradename Risperdal, manufactured by Janssen Pharmaceuticals, Inc. Quetiapine may be sold under the tradename Seroquel, manufactured by AstraZeneca. One exemplary typical antipsychoticis haloperidol, which may be sold under the tradename Haldol, manufactured by Janssen Pharmaceuticals, Inc.

In another embodiment, the active agent may be an anxiolytic. For example, benzodiazepines. Benzodiazepines may be selected, for example, from the group consisting of lorazepam, diazepam, clonazepam, or combinations thereof. Lorazepam may be sold under the tradename Ativan, manufactured by Pfizer. Diazepam may be sold under the tradename Valium, manufactured by Roche Pharmaceuticals. Clonazepam is sold under the tradename Klonopin, manufactured by Roche Laboratories.

In further embodiments, the active agent may be a mood stabilizer selected from the group consisting of lithium, valproate, or combinations thereof. Valproate may be sold under the tradename Depakote, manufactured by Abb Vic.

In additional embodiments, the active agent may be a stimulant selected from the group consisting of methylphenidate, amphetamine, dextroamphetamine, or combinations thereof. For example, methylphenidate may be sold under the tradename Ritalin, manufactured by Novartis, or the tradename Concerta, manufactured by Janssen Pharmaceutical, Inc. In certain embodiments, the stimulant may comprise a combination of amphetamine and dextroamphetamine. For example, the combination of amphetamine and dextroamphetamine may be sold under the tradename Adderall, manufactured by Teva Pharmaceuticals.

In some embodiments, the active agent may be antiepileptic drugs (AEDs) selected from the group consisting of levetiracetam, carbamazepine, lamotrigine, or combinations thereof. For example, levetiracetam may be sold under the tradename Keppra, manufactured by UCB Pharmaceuticals S.A. Carbamazepine may be sold under the tradename Tegretol, manufactured by Novartis. Lamotrigine may be sold under the tradename Lamictal, manufactured by GlaxoSmithKline (GSK).

In various embodiments, the active agent may be Parkinson's disease medications selected from the group consisting of levodopa, carbidopa, dopamine agonists, or combinations thereof. For example, a combination of levodopa and carbidopa may be sold under the tradename Sinemet, manufactured by Merck Sharp and Dohme Limited (MSD). Dopamine agonists may be selected, for example, from the group consisting of pramipexole, ropinirole, or combinations thereof. Pramipexole may be sold under the tradename Mirapex, manufactured by Boehringer Ingelheim Pharmaceuticals, Inc. Ropinirole may be sold under the tradename Requip, manufactured by GlaxoSmithKline (GSK).

In one embodiment, the active agent may be migraine medication selected from the group consisting of triptans, preventive medications, or combinations thereof. In certain embodiments, triptan may be sumatriptan. Sumatriptan may be sold under the tradename Imitrex, manufactured by GlaxoSmithKline. In certain embodiments, the preventative medication may be topiramate. Topiramate may be sold under the tradename Topamax, manufactured by Janssen Pharmaceuticals, Inc.

In certain embodiment, the active agent may be narcotics/opioids selected from the group consisting of morphine, oxycodone, or combinations thereof. Oxycodone may be sold under the tradename OxyContin, manufactured by Purdue Pharma LP.

In one embodiment, the active agent may be a muscle relaxant that is baclofen.

In some embodiments, the active agent delivered through the BBB is a monoclonal antibody. Monoclonal antibodies may be useful in treating conditions related to the CNS, including those discussed previously. In certain embodiments, monoclonal antibodies are particularly suited for treatment of CNS conditions selected from a group consisting of neurodegenerative diseases, multiple sclerosis, neuropathic pain, autoimmune encephalitis, or combinations thereof.

Monoclonal antibodies useful in treating neurodegenerative diseases may be selected from, for example, the group consisting of Aducanumab, Lecanemab, or combinations thereof. In some embodiments, Aducanumab may be those listed above. Lecanemab may be, in various embodiments, those listed above.

In certain embodiments, monoclonal antibodies useful for treating multiple sclerosis may be selected from the group consisting of natalizumab, ocrelizumab, rituximab, or combinations thereof. Natalizumab may, in certain embodiments, target the alpha-4 integrin and prevent immune cells from entering the brain. Natalizumab may be sold under the tradename Tysabri, manufactured by Biogen Idec. Ocrelizumab may, in some embodiments, target CD20 on B cells and treat relapsing and primary progressive forms of multiple sclerosis. Ocrelizumab may be sold under the tradename Ocrevus, manufactured by Genentech. Rituximab may, in various embodiments, be an anti-CD20 monoclonal antibody used off-label for treatment of certain types of multiple sclerosis. Rituximab may be sold under the tradename Rituxan, manufactured by Biogen Idec and Genentech.

In some embodiments, monoclonal antibodies useful for treating neuropathic pain may be selected from the group consisting of erenumab, fremanezumab, or combinations thereof. Erenumab may, in certain embodiments, prevent migraines by targeting the calcitonin gene-related peptide (CGRP). Erenumabmay be sold under the tradename Aimovig, manufactured by Amgen and Novartis. Fremanezumab may, in some embodiments, prevent migraines by targeting the CGRP. Fremanezumab may be sold under the tradename Ajovy, manufactured by Teva Pharmaceutical Industries Ltd.

In various embodiments, monoclonal antibodies useful for treating autoimmune encephalitis may include rituximab. Rituximab, as detailed above, may be, in some embodiments, treat autoimmune encephalitis by targeting specific antibodies.

Still further, the monoclonal antibodies discussed herein may include inotuzumab ozogamicin. Inotuzumab ozogamicin may be useful in treating various CNS related diseases and may be sold under the tradename Besponsa, manufactured by Pfizer Inc.

Additionally, anti-tau and anti-amyloid monoclonal antibodies may be utilized as the active agent. Anti-tau antibodies target tau protein aggregates in Alzheimer's disease and other tauopathies. Anti-amyloid antibodies provide an additional source of amyloid-targeting therapies.

In some embodiments, the active agent delivered through the BBB is an immune therapy agent useful for treating CNS conditions. For example, the immune therapy agent may be selected from the group consisting of monoclonal antibodies, immune checkpoint inhibitors, cancer vaccines, or combinations thereof.

In certain embodiments, the monoclonal antibodies may include any of the monoclonal antibodies discussed above. For example, those selected from the group consisting of rituximab, ocrelizumab, aducanumab, lecanemab, or combinations thereof.

In various embodiments, immune checkpoint inhibitors may be selected from the group consisting of nivolumab, pembrolizumab, or combinations thereof. Nivolumab and pembrolizumab are PD-1 inhibitors that may be useful in treating CNS tumors like glioblastoma. Nivolumab may be sold under the tradename Opdivo, manufactured by Bristol Myers Squibb. Pembrolizumab may be sold under the tradename Keytruda, manufactured by Merck Sharp & Dohme Corp.

In some embodiments, cancer vaccines may be selected from the group consisting of DCVax-L, EDFRvIII-targeted vaccines, or combinations thereof. DCVax-L is a dendritic cell vaccine designed to treat glioblastoma and, in certain embodiments, stimulate the immune system against tumor antigens. EGFRvIII is may, in some embodiments, target specific mutations form of the epidermal growth factor receptor commonly found in glioblastoma.

In other embodiments, the immune therapy agent may an agent used in a therapy selected from the group consisting of T-cell therapy, cytokine therapy, oncolytic virus therapy, adjuvant therapy, or neuroinflammatory disease therapy, or combinations thereof.

T-cell therapies may be selected, for example, from the group consisting of Chimeric Antigen Receptor (CAR) therapy, Tumor-Infiltrating Lymphocyte (TIL) therapy, or combinations thereof. CAR therapy may be useful in treating CNS tumors, specifically those expressing specific tumor antigens. TIL therapy leverages T cells that have infiltrated tumors to attack glioblastoma cells.

Cytokine therapies may be selected, for example, from the group consisting of interleukins (IL)-2, IL-12, or combinations thereof. IL-2 and IL-12 use interleukins to enhance immune responses in brain tumors and other CNS conditions.

Oncolytic virus therapy may include, for example, active agents that are viruses selected from the group consisting of Toca 511, Herpes Simplex Virus (HSV)-1, or combinations thereof. Toca 511 is an oncolytic virus designed to, among other things, selectively replicate in and kill cancer cells, such as glioblastoma. HSV-1 may be useful in targeting and destroying tumor cells in the brain.

Adjuvant therapies are known to, among other things, enhance efficacy in treating CNS tumors. Adjuvant therapies may include the use of active agents that are immune checkpoint inhibitors (for example as discussed above). In certain embodiments, the immune checkpoint inhibitors may be used in combinations with additional therapies such as chemotherapy and/or radiation.

Neuroinflammatory disease treatments may include therapies for targeting neuroinflammation. For example, neuroinflammatory disease treatments may comprise of use of active agents that are immunomodulatory agents. Immunomodulatory agents may be useful in treating multiple sclerosis and other neuroinflammatory conditions.

In some embodiments, the active agent may be a medication used to treat anxiety disorders. For example, anxiety disorders may be selected from the group consisting of generalized anxiety disorder, social anxiety disorder, panic disorder, or combinations thereof.

In certain embodiments, an active agent used to treat anxiety disorders may be selected from the group consisting of selective serotonin reuptake inhibitors (SSRIs), serotonin-norepinephrine reuptake inhibitors (SNRIs), benzodiazepines, buspirone, antipsychotics, or combinations thereof.

In certain embodiments, SSRIs may be selected from the group consisting of escitalopram, paroxetine, sertraline, or combinations thereof. In other embodiments, SSRIs may be selected from the groups discussed elsewhere herein. Escitalopram is sold under the tradename Lexapro, manufactured by Forest Laboratories, Inc. Paroxetine is sold under the tradename Paxil, manufactured by GlaxoSmithKline. Sertraline is sold under the tradename Zoloft, manufactured by Pfizer Inc.

In other embodiments, SNRIs may be selected from the groups discussed elsewhere herein.

In various embodiments, benzodiazepines may be selected from the groups discussed elsewhere herein. In certain embodiments, the selected benzodiazepines may be designed for short-term use.

In some embodiments, the buspirone may be an anxiolytic, which may be effective in treating generalized anxiety disorders.

In one embodiment, an antipsychotic active agent for the treatment of anxiety disorders may include quetiapine.

In certain embodiments, other active agents for the treatment of anxiety disorders may be selected from the group consisting of pregabalin, hydroxyzine, or combinations thereof. Pregabalin may be sold under the tradename Lyrica, manufactured by Pfizer Inc. Hydroxyzine may be sold under the tradename Vistaril, manufactured by Pfizer Inc.

In some embodiments, the active agent delivered through the BBB is a medication used to treat multiple sclerosis that is selected from the group consisting of disease-modifying therapies (DMTs), symptomatic treatments, or combinations thereof. In certain embodiments, DMTs may be selected from the group consisting of injectable therapies, oral therapies, infused therapies, or combinations thereof.

For example, DMT injectable therapies may be selected from the group consisting of interferon beta-la, interferon beta-1b, glatiramer acetate, or combinations thereof. Interferon beta-la may be sold under the tradenames Avonex, manufactured by Biogen Inc., or Rebif, manufactured by Merck KGaA. Interferon beta-1b may be sold under the tradename Betaseron, manufactured by Bayer HealthCare Pharmaceuticals Inc. Glatiramer acetate may be sold under the tradename Copaxone, manufactured by Teva Pharmaceuticals Industries Ltd.

In certain embodiments, DMT the oral therapies may be selected from the group consisting of fingolimod, dimethyl fumarate, teriflunomide, or combinations thereof. Fingolimod may be sold under the tradename Gilenya, manufactured by Novartis Pharmaceuticals. Dimethyl fumarate may be sold under the tradename Tecfidera, manufactured by Biogen Inc. Teriflunomide may be sold under the tradename Aubagio, manufactured by Sanofi Genzyme.

In other embodiments, DMT infused therapies may be selected from the group consisting of natalizumab, ocrelizumab, alemtuzumab, or combinations thereof. Natalizumab and Ocrelizumab are discussed in further detail herein. Alemtuzumab may be sold under the tradename Lemtrada, manufactured by Sanofi US.

Symptomatic treatments may include, for example, any investigational medication that targets specific symptoms an individual with multiple sclerosis may experience. For example, the symptoms of fatigue and/or spasticity.

In certain other embodiments, new treatments and therapies addressing underlying disease mechanisms such as monoclonal antibodies and other innovative treatments may be employed as active agents.

In various embodiments, the active agent delivered through the BBB is a medication that is used to treat schizophrenia. For example, the medications that are used to treat schizophrenia may be selected from the group consisting of antipsychotics, adjunctive treatments, investigative medications, or combinations thereof. Antipsychotics may be selected from the group consisting of atypical antipsychotics, typical antipsychotics, or combinations thereof.

In certain embodiments, atypical antipsychotics may be selected from the group consisting of lurasidone, cariprazine, brexpiprazole, olanzapine, quetiapine, or combinations thereof. In other embodiments, typical antipsychotics may be selected from the group consisting of haloperidol, chlorpromazine, or combinations thereof.

Adjunctive treatments are discussed above and include medications that may be administered in combination with antipsychotics. For example, antidepressants, mood stabilizers, or combinations thereof. In some embodiments, the antidepressant may be selected from the groups discussed elsewhere herein. In certain embodiments, the antidepressant is selected from the group sertraline, fluoxetine, or combinations thereof. An example of a mood stabilizer is lithium.

In various embodiments, investigative medications that target alternative pathways for treatment may be utilized. For example, the investigative medications may be selected from the group consisting glycine modulators, cannabinoid receptor modulators, or combinations thereof.

In certain specific embodiments, the active agent delivered through the BBB is a medication used to treat schizophrenia that is selected from the group consisting of dopaminergic agonists, levodopa formulations, neuroprotective agents, glutamate modulators, gene therapy, biologics, or combinations thereof.

Dopaminergic agonist may be selected, for example, from the group consisting of rasagiline, pramipexole, or combinations thereof. Rasagiline is an MAO-B inhibitor that may help to increase dopamine levels. Pramipexole may mimic the effects of dopamine in the brain.

In certain embodiments, levodopa formulations are selected from the group consisting of IPX203, acorda therapeutics' inbrija, or combinations thereof. IPX203 is an extended-release formulation of levodopa and carbidopa. The combination of levodopa and carbidopa is described elsewhere herein. Acorda therapeutics' inbrija may aid in treatment of off episodes of schizophrenia.

Neuroprotective agents may include, for example, NXY-059. NXY-059 may improve neuroprotective effects in Parkinson's patients and may have added benefits in treating schizophrenia. In further embodiments, neuroprotective agents may include nerve growth factor therapies, antioxidants, or combinations thereof.

In one embodiment, the glutamate modulator may be riluzole. Riluzole may slow down the progression of Parkinson's disease and may have added benefits in treating schizophrenia.

In certain embodiments, gene therapies may include AAV2-GAD. AAV2-GAD is a gene therapy that may increase GABA levels in the brain.

Biologics may include, for example, neurotrophic factors, which promote neuron survival and function.

Still further active agents may include Cortexyme's COR388, which reduce neuroinflammation.

In some embodiments, the active agent delivered through the BBB is a medication used to treat traumatic brain injury. For example, the active agent may be selected from the group consisting of neuroprotective agents, anti-inflammatory drugs, cognitive enhancers, antidepressants, hormonal treatments, or combinations thereof.

Neuroprotective agents may be useful in protecting brain cells from damage. In certain embodiments, the neuroprotective agent is selected from the group consisting of minocycline, N-acetylcysteine (NAC), or combinations thereof. In certain embodiments, Neuroprotective agents may include any of the neuroprotective agents discussed above.

Anti-inflammatory drug may reduce inflammation in the brain post-injury. In some embodiments, the anti-inflammatory drug is selected from the group consisting of corticosteroid, nonsteroidal anti-inflammatory drug (NSAIDs), or combinations thereof. Corticosteroids are known to, among other things, be potent anti-inflammatory agents and useful in reducing inflammation in conditions like multiple sclerosis (MS) and other auto immune disorders. In certain embodiments, the corticosteroid may be prednisone, dexamethasone, or combinations thereof.

Cognitive enhancers may assist in improving cognitive function with individuals having traumatic brain injury. In certain embodiments, the cognitive enhancer is selected from the group consisting of donepezil, rivastigmine, or combinations thereof.

Antidepressant may help mood stabilization and cognitive recovery. In some embodiments, the antidepressant is selected from the group listed above.

Hormonal treatment may also exhibit neuroprotective effects. In one embodiment, the hormonal treatment may be progesterone.

In some embodiments, the active agent delivered through the BBB is a medication used to treat meningitis. In certain embodiments, the active agent used to treat meningitis is selected from the group consisting of ciprofloxacin, ceftriaxone, meropenem, vancomycin, pneumococcal vaccines, meningococcal vaccines, rifampicin, adjunctive therapies, or combinations thereof.

Ciprofloxacin is effective against bacterial meningitis caused by resistant strains. Ceftriaxone is a broad-spectrum cephalosporin used to, among other things, treat various types of bacterial meningitis. Meropenem is a carbapenem antibiotic efficient in treating meningitis caused by Gram-negative bacteria. Vancomycin is particularly suited for treatment of resistant strains of bacteria. Pneumococcal vaccines prevent meningitis caused by *Streptococcus pneumonia*. In certain embodiments, pneumococcal vaccines may be selected from the group consisting of PCV13, PPSV23, or combinations thereof. Meningococcal vaccines prevent meningococcal meningitis. Rifampicin may be used as a prophylactic treatment in individuals who are or have been in close contact individuals having meningococcal meningitis. Adjunctive therapies may include anti-inflammatory agents, which are known to improve the effects of bacterial meningitis.

In some embodiments, the active agent delivered through the BBB is a medication that is used to treat epilepsy. For example, the active agent that is used to treat epilepsy may be selected from the group consisting of lacosamide, perampanel, eslicarbazepine acetate, brivaracetam, cannabidiol, fenfluramine, vigabatrin, soticlestat, aptiom, or combinations thereof.

Lacosamide is an anticonvulsant drug used for partial-onset seizures, that has shown efficacy in reducing seizure frequency. Perampanel is an AMPA receptor antagonist that may control seizures in patients with epilepsy. Eslicarbazepine acetate may reduce seizures in adults and children. Brivaracetam may treat patients with partial onset seizures and may be sold under the tradename Aptiom, manufactured by Sunovion Pharmaceuticals. Cannabidiol may reduce seizures in individual with Dravet and Lennox-Gastaut syndromes and may be sold under tradename Epidiolex, manufactured by GW Pharmaceuticals Group PLC. Fenfluramine may be used to treat individuals with Dravet syndrome. Vigabatrin may reduce infantile spasms and refractory epilepsy. Soticlestat may, in certain embodiments, target the enzyme cholesterol 24-hydroxylase and reduce seizures in children with Dravet and Lennox-Gastaut syndromes.

In some embodiments, the active agent delivered through the BBB is a medication that is useful in treating Cerebral Palsy. The active agent that is useful in treating Cerebral Palsy may be selected from the group consisting of botulinum toxin A, intrathecal baclofen, dantrolene sodium, result from stem cell therapy, resveratrol, n-acetylcysteine (NAC), sodium valproate, cerebrolysin, or combinations thereof.

Botulinum toxin A may reduce spasticity in children with Cerebral Palsy and may be sold under the tradename Botox. Intrathecal baclofen may reduce severe spasticity in Cerebral Palsy patients. Dantrolene sodium is a muscle relaxant that may effective in treating spasticity in patients with Cerebral Palsy.

In certain embodiments, active agents resulting from stem cell therapy may be selected from therapy groups consisting of neural stem cell transplantation, induced pluripotent stem cells (iPSCs), or combinations thereof. For example, neural stem cell transplantation may regenerate damaged tissue in conditions like stroke and spinal cord injury. Induced pluripotent stem cells (iPSCs) may be useful in treating neurodegenerative diseases. In certain specific embodiments, stem cell therapy may comprise umbilical cord blood-derived stem cells.

Resveratrol is an antioxidant that may improve neuroprotective effects in Cerebral Palsy patients. N-acetylcysteine is an antioxidant that may improve motor functions in Cerebral Palsy patients. Sodium valproate may improve spasticity and seizures associated with Cerebral Palsy. Cerebrolysin is a neuropeptide mixture that has shown promising neuroprotective properties in children with Cerebral Palsy.

In some embodiments, the active agent delivered through the BBB is a medication that is useful in treating Amyotrophic Lateral Sclerosis (ALS). The active agent that is useful in treating ALS may be selected from the group consisting of riluzole, edaravone, tofersen, masitinib, sodium phenylbutyrate, taurursodiol, tirasemtiv, mesenchymal stem cells, L-serine, or combinations thereof.

Riluzole improves survival and functions in patients with ALS. Edaravone is an antioxidant therapy that has shown efficacy in slowing the decline in physical functions in ALS patients and may be sold under the tradename Radicava, manufactured by Mitsubishi Tanabe Pharma America (MTPA). Tofersen is an antisense oligonucleotide that targets the SODI gene and is designed for the treatment of familial ALS caused by SODI mutations. Masitinib is a tyrosine kinase inhibitor that may slow ALS progression. Tirasemtiv is a skeletal muscle troponin activator that improves muscle function. Mesenchymal stem cells promote neuronal survival and may be sold under the tradename NurOwn, manufactured by BrainStorm Cell Therapeutics. L-serine is an amino acid that provides neuroprotective effects in ALS patients.

In certain embodiments sodium phenylbutyrate may be combined with taurursodiol. The combination of sodium phenylbutyrate and taurursodiol may be sold under the tradename AMX0035, manufactured by Amylyx Pharmaceuticals.

Certain specific active agents that may be delivered through the BBB may be selected from the group consisting of lecanemab, donanemab, budesonide, formoterol, ponesimod, ozanimod, rivastigmine, tafamidis, ABP-938, or combinations thereof.

Budesonide is a corticosteroid that reduces inflammation in airways. Formoterol is a long-acting beta-agonist that relaxes the muscles in the airways. In certain embodiments, budesonide and formoterol are combined to treat asthma and chronic obstructive pulmonary disease (COPD). For example, the combination budesonide and formoterol may be sold under the tradename Breztri Acrosphere, manufactured by AstraZeneca.

Ponesimod is a selective SIP receptor modulator used in the treatment of multiple sclerosis. Ozanimod is an SIP receptor modulator and be useful in treating ulcerative colitis and multiple sclerosis. Rivastigmine may be useful in treating dementia. Tafamidis is useful in treating transthyretin amyloid polyneuropathy. ABP-938 may treat anxiety disorders.

In some embodiments, the active agent delivered through the BBB is a molecule used in recombinant DNA technology and therapies related to the central nervous system (CNS). For example, the molecule used in recombinant DNA technology and therapies related to the CNS may be selected from the group consisting of vectors, proteins, nucleic acids, peptides, small molecules, cytokines, growth factors, gene therapy products, sustained release systems, or combinations thereof.

In certain embodiments, the vectors may be selected from the adeno-associated virus (AAV), lentivirus, baculovirus, or combinations thereof. Adeno-associated virus facilitates gene delivery in gene therapy. Lentivirus is a retroviral vector that stabilizes gene expression in dividing and non-dividing cells. Baculovirus is a virus commonly used in insect cells for producing recombinant proteins.

In various embodiments, the proteins may be selected from the group consisting of neurotrophic factors, monoclonal antibodies, enzymes, glucocerebrosidase, aromatic L-amino decarboxylase, or combinations thereof. In further embodiments, proteins may be selected from the group consisting of recombinant human erythropoietin (EPO), brain-derived neurotrophic factor (BDNF), nerve growth factor (NGF), glial cell line-derived neurotrophic factor (GDNF), insulin, fibroblast growth factors (FGFs), transforming growth factor-beta (TGF-$\beta$), interferons, monoclonal antibodies, antibody fragment, cytokine, humanized antibody, protein kinase inhibitor, neurotrophin, caspase inhibitor, or combinations thereof.

Monoclonal antibodies are known to, among other things, target specific proteins like amyloid-beta or tau and are discussed in further detail herein.

In certain embodiments, the enzymes may be selected from the group consisting of asparaginase, L-asparaginase, cholinesterase inhibitors, glucocerebrosidase, arylsulfatase A, Iduronate-2-sulfatase, N-acetylgalactosamine-6-sulfatase, sphingomyelinase, caspases, matrix metalloproteinases (MMPs), dipeptidyl peptidase-4 (DPP-4) inhibitors, cathepsins, superoxide dismutase (SOD), adenosine deaminase, histone deacetylases (HDACs), or combinations thereof.

Asparaginase may be useful in the treating of acute lymphoblastic leukemia by depleting asparagine level. L-asparaginase is a form of asparaginase known to, among other things, be used in treating pediatric leukemia. Cholinesterase inhibitors are enzymes that are known to, among other things, inhibit acetylcholinesterase (such as donepezil, rivastigmine, or similar) and treat Alzheimer's disease by increasing acetylcholine levels. Glucocerebrosidase is an enzyme replacement therapy using modified glucocerebrosidase and may be utilized for Gaucher's disease which may affect the CNS. Arylsulfatase A may be used in enzyme replacement therapy for metachromatic leukodystrophy, a genetic disorder affecting the CNS.

Iduronate-2-sulfatase is an enzyme used in enzyme replacement therapy for Hunter syndrome, which affects neurological function.

N-acetylgalactosamine-6-sulfatase may be used in enzyme replacement therapy for Morquio A syndrome, which can have neurological implications.

Sphingomyelinase is an enzyme known to, among other things, be used in therapies for Niemann-Pick disease, which effects the CNS.

Caspases are known to, among other things, be involved in apoptosis and have therapeutic potential in neurodegenerative diseases by modulating cell death pathways.

MMPs are known to be, among other things, enzymes involved in extracellular matrix remodeling and effective in treating in CNS injuries and diseases.

DPP-4 inhibitors are known to, among other things, be useful in treating diabetes and CNS disorders.

Cathepsins are known to be, among other things, proteolytic enzymes involved in various neurodegenerative diseases and useful as therapeutic targets.

SOD is an antioxidant enzyme that reduce oxidative stress in neurodegenerative diseases.

Adenosine deaminase may have a role in purine metabolism and have implications in neuroinflammatory conditions.

HDACs are known to, among other things, have benefits in neurodegenerative diseases by modifying gene expression.

In certain embodiments, enzymes employed in the present disclosure may be employed in the context of enzyme modification of the CNS. This is an emerging area of research aimed at addressing various neurological disorders and enhancing therapeutic strategies. Enzyme modification may include one or more of targeted enzyme delivery, enzyme stabilization, enzyme replacement therapy, gene therapy, the use of biodegradable hydrogels, the use of enzyme inhibitors, enzyme engineering for neuroprotection, and bioorthogonal chemistry. Targeted enzyme delivery may comprise modifying enzymes to improve their ability to cross the blood-brain barrier (BBB). Techniques like pegylation (adding polyethylene glycol) can enhance the solubility and stability of enzymes, making them more effective in CNS applications. Enzyme stabilization may comprise chemical modifications to enhance the stability and activity of enzymes under physiological conditions. For example, site-directed mutagenesis can create enzyme variants with improved catalytic efficiency or resistance to proteolysis. In conditions like lysosomal storage disorders, modified enzymes can be used to replace deficient or malfunctioning enzymes in the CNS. These enzymes can be engineered for better uptake by neuronal cells. Enzymes can also be delivered through gene therapy, where modified viral vectors carry the genes encoding therapeutic enzymes into CNS cells. This approach can provide a continuous supply of the enzyme and may be more effective than traditional enzyme replacement. Enzymes can be encapsulated in biodegradable hydrogels that release the enzyme in a controlled manner. This method can be used for localized treatment of CNS injuries or diseases, ensuring prolonged activity at the site of action. In some embodiments, inhibiting specific enzymes can be beneficial for treating CNS disorders. For example, inhibitors of Cholinesterase can be used to treat Alzheimer's disease by increasing levels of acetylcholine. Bioorthogonal chemistry allows for the precise modification of enzymes in living organisms without interfering with native biological processes, offering a way to enhance enzyme function in the CNS selectively.

Glucocerebrosidase is useful in treating lysosomal storage disorders. Aromatic L-amino acid decarboxylase is effective in Parkinson's therapy.

EPO may be used to treat anemia and have neuroprotective effects in conditions like stroke and traumatic brain injury.

BDNF may promote neuronal survival and growth in neurodegenerative disease.

NGF is a protein that supports that survival and growth of neurons and treat Alzheimer's disease and peripheral neuropathy.

GDNF may improve neuroprotective effects in Parkinson's disease and other neurodegenerative conditions. In particular, GDNF may support neuron survival and growth.

Insulin may have neuroprotective properties and effect cognitive function and neurodegeneration.

FGFs may assist in neuroprotection and regeneration and treat various CNS disorders.

TGF-$\beta$ may have roles in inflammation and neuroprotection, with potential therapeutic applications in CNS diseases.

Interferons may be useful in treating of multiple sclerosis to modulate immune responses and reduce inflammation in the CNS.

Monoclonal antibodies are discussed in further detail herein and may be useful in treating multiple sclerosis by depleting specific immune cells that attack myelin. In certain embodiments, monoclonal antibody is ocrelizumab.

Antibody fragment may be useful in treating in Alzheimer's disease that targets amyloid-beta plaques associated with the disease. In certain embodiments, antibody fragment is aducanumab.

Cytokine are proteins known to, among other things, be involved in inflammatory responses and treat neuroinflammatory conditions. In certain embodiments, cytokine may be tumor necrosis factor-alpha (TNF-$\alpha$) inhibitors. Other cytokines are discussed elsewhere herein.

Humanized antibodies may be useful in treating multiple sclerosis by inhibiting the migration of immune cells across the blood-brain barrier. Humanized antibodies may be between 90% and 95% derived from human immunoglobulin and small portions from a mouse. Humanized antibodies are known to, among other things, preserve the antibody's specificity for its target while reducing the likelihood of an immune response against the antibody itself and are useful in treating various conditions, such as cancer or autoimmune diseases. While humanized antibodies are less immunogenic than mouse antibody, there is still a potential risk of immune response due to the presence of mouse-derived sequences. This can lead to the development of anti-drug antibodies (ADAs), which may reduce the efficacy of treatment. In certain embodiments, humanized antibody may be selected from the group consisting of trastuzumab, omalizumab, natalizumab, rastuzumab, or combinations thereof. For example, trastuzumab may be sold under the tradename Herceptin manufactured by F. Hoffmann-La Roche Lt., and omalizumab may be sold under the tradename Xolair manufactured by Genentech and Novartis Pharmaceuticals Corporation. Natalizumab may be used as detailed above.

If immunogenicity is a concern, researchers may prefer fully human antibodies which minimizes immunogenicity even further compared to humanized antibodies, as there are no residual mouse components. Fully human antibodies may be produced using human immunoglobulin genes and are known to, among other things, minimize the risk of immune reactions in patients and be useful in treating various diseases, including cancer, infectious diseases, and chronic conditions. A benefit of the full human antibody is the absence of non-human components which virtually eliminates the risk of immune reactions directed against the antibody itself, making these therapies more suitable for long-term use in patients. In certain embodiments, fully human antibodies may be selected from the group consisting of adalimumab, pembrolizumab, or combinations thereof. For example, adalimumab may be sold under the tradename Humira manufactured by Abb Vie, and pembrolizumab may be sold under the tradename Keytruda manufactured by Merck.

Protein kinase inhibitors target specific kinases involved in neurodegenerative pathways and have therapeutic potential.

Neurotrophin may support neuron growth and survival and have a role in neurodegeneration and injury diseases.

Caspase inhibitor may include a protein known to inhibit the activity of caspases involved in apoptosis and prevent neuronal cell death in neurodegenerative diseases.

In some embodiments, the nucleic acids may be selected from the group consisting of plasmid DNA, antisense oligonucleotides, CRISPR/Cas9 components, guide RNA (gRNA), Cas9 proteins, or combinations thereof.

Plasmid DNA is known, among other things, to be a vector for gene delivery. Antisense oligonucleotides may be useful in gene silencing or modulation of gene expression. Guide RNA may direct Cas9 to specific genomic locations for editing. Cas9 protein is an enzyme useful for cutting DNA.

Peptides may be selected, for example, from the group consisting of neuropeptides, cell-penetrating peptides, or combinations thereof. Neuropeptides are known to, among other things, modulate neuronal activity. Neuropeptides may include, for example, substance P, beta-endorphin, or combinations thereof. Cell-penetrating peptides facilitate the delivery of larger molecules across cell membranes.

In certain embodiments, small molecules may be selected from the group consisting of inhibitors, neuroprotective agents, or combinations thereof. Inhibitors are known to, among other things, assist in studying pathways involved in CNS disorders. Neuroprotective agents are discussed in further detail herein and may protect neurons from damage.

Cytokines are known to, among other things, modulate immune responses in the CNS. In certain embodiments, cytokines may be selected from the group consisting of interleukins, tumor necrosis factor-alpha (TNF-alpha), or combinations thereof. Interleukins, such as IL-1 or IL-6, may be helpful in modulating immune responses in the CNS. TNF-alpha may assist in inflammatory responses. Cytokines may include cytokines therapies disclosed above.

Growth factors may be selected, for example, from the group consisting of fibroblast growth factor, insulin-like growth factor, or combinations thereof. Fibroblast growth factors are useful in neuroprotection and regeneration.

In certain embodiments, neurotrophic factors may be selected from the group consisting of brain-derived neurotrophic factor, glial cell line-derived neurotrophic factor, or combinations thereof.

In certain embodiments, the active agent may comprise therapeutics selected from the group consisting of hormones, peptides, antisense oligonucleotides, gene therapy vectors, sustained release systems, or combinations. In certain embodiments, the active agent may comprise a therapeutic that is albumin.

Hormones are known to, among other things, have effects on brain metabolism and neuroprotection. In certain embodiments, hormones may be selected from the group consisting of insulin, growth hormones, or combinations thereof.

Peptides are discussed in further detail herein and are known to, among other things, have roles in pain modulation and other CNS functions. In certain embodiments, peptides may be selected from the group consisting of substance P, beta-endorphin, or combinations.

Antisense oligonucleotides are known to, among other things, be used for gene silencing in conditions like Huntington's disease.

Gene therapy vectors are known to, among other things, deliver genes to neurons. In certain embodiments, gene therapy products (e.g., vectors) may be recombinant viral vectors. Recombinant viral vectors may assist in delivery of therapeutic genes directly to the CNS. For example, AAV-based gene therapy uses adeno-associated viruses to deliver therapeutic genes for conditions like spinal muscular atrophy (SMA) and Huntington's disease. CRISPR and Cas9 may also be used in treating various genetic CNS disorders via gene therapy.

Sustained release systems are known to, among other things, release therapeutic proteins over time for chronic conditions.

In some embodiments, the active agent delivered through the BBB may be a pharmaceutical antibody. For example, the pharmaceutical antibody may be selected from the group consisting of humanized antibody, fully human antibody, chimeric antibody, bispecific antibody, or combination thereof.

Humanized antibodies are discussed in further detail above and are predominately human antibodies with only a small portion of mouse antibody sequences and known to, among other things, provoke less immune response.

Fully human antibodies are discussed in further detail above and may be produced using human immunoglobulin genes and may minimize the risk of immune reactions in patients and be useful in treating various diseases, including cancer, infectious diseases, and chronic conditions.

Chimeric antibodies may comprise both human and mouse components and are known to, among other things, retain the specificity of mouse antibodies with reducing immunogenicity. In certain embodiments, chimeric antibody may be rituximab which may be sold under the tradename Rituxan, manufactured by Genentech, Biogen, and Roche.

Bispecific antibodies are known to, among other things, bind two different antigens simultaneously and redirect immune cells to target cancer cells more effectively. In certain embodiments, bispecific antibodies may be blinatumomab which may be sold under the tradename Blincyto manufactured by Amgen Inc.

In some embodiments, pharmaceutical antibodies may also include next-generation antibody-drug conjugate (ADCs), combination therapies, and/or personalized medicine. Next-generation ADCs are known to, among other things, enhance the delivery and potency of cytotoxic drugs. Combination therapies may use antibodies in conjunction with other treatment modalities like immune checkpoint inhibitors (for example as discussed above) or small molecules drugs. Personalized medicine may be used to tailor antibody therapies based on individual patient profiles tumor characteristics for more effective treatments.

In some embodiments, the active agent delivered through the BBB may be a targeted antibody therapy. In certain embodiments, the targeted antibody therapy may treat cancers that express specific antigens that can be effectively targeted. For example, the types of cancers that may be treated by a targeted antibody therapy may be selected from the group consisting of breast cancer, non-Hodgkin lymphoma, Hodgkin lymphoma, colorectal cancer, lung cancer, melanoma, kidney cancer, head and neck cancers, gastric cancer, multiple myeloma, prostate cancer, or combinations thereof.

In certain embodiments, the targeted antibody therapy useful in treating breast cancer may be selected from the group consisting of trastuzumab, pertuzumab, ado-trastuzumab emtansine, or combinations thereof. Trastuzumab may target the HER2 protein which is over-expressed in some breast cancers. For example, trastuzumab may be sold under the tradename Herceptin manufactured by F. Hoffmann-La Roche Ltd. For example, ado-trastuzumab emtansine may be sold under the tradename Kadcyla manufactured by Genentech.

In some embodiments, the targeted antibody therapy useful in treating non-Hodgkin lymphoma may be rituximab which targets the CD20 antigen on B-cells and treat various forms of non-Hodgkin lymphoma. For example, rituximab may be sold under the tradename Rituxan manufactured by Genentech and Biogen.

In various embodiments, the targeted antibody therapy useful in treating Hodgkin lymphoma may be brentuximab vedotin which targets CD30. Brentuximab vedotin may be sold under the tradename Adcetris manufactured by Pfizer.

In other embodiments, the targeted antibody therapy useful in treating colorectal cancer may be cetuximab which targets the epidermal growth factor receptor. Cetuximab may be sold under the tradename Erbitux manufactured by Eli Lilly.

In still further embodiments, the targeted antibody therapy useful in treating lung cancer may be selected from the group consisting of monoclonal antibodies, PD-1 inhibitor, PD-L1 inhibitor, or combinations thereof. Monoclonal antibodies are known to, among other things, target EGFR. For example, monoclonal antibodies may be cetuximab. For example, PD-1 inhibitor may be pembrolizumab. For example, PD-L1 inhibitors may be nivolumab.

In certain embodiments, the targeted antibody therapy useful in treating melanoma may be selected from the group consisting of pembrolizumab, nivolumab, ipilimumab, or combinations thereof. For example, pembrolizumab may be sold under the tradename Keytruda manufactured by Merck & Co. For example, nivolumab may be sold under the tradename Opdivo manufactured by Bristol-Myers Squibb. For example, ipilimumab targets CTLA-4 and may be sold under the tradename Yervoy manufactured by Bristol-Myers Squibb.

In various embodiments, the targeted antibody therapy useful in treating kidney cancer may be nivolumab which may be effective in treating advanced renal cell carcinoma by targeting the PD-1 pathway. For example, nivolumab may be sold under the tradename Opdivo manufactured by Bristol-Myers Squibb.

In some embodiments, the targeted antibody therapy useful in treating head and neck cancers may be cetuximab which targets the EGFR.

In one embodiment, the targeted antibody therapy useful in treating gastric cancer may be trastuzumab which may be useful in treat HER2-positive gastric or gastroesophageal junction cancers.

In certain embodiments, the targeted antibody therapy useful in treating multiple myeloma may be daratumumab which targets CD38 and treat multiple forms of myeloma. Daratumumab may be sold under the tradename Darzalex manufactured by Genmab.

In other embodiments, the targeted antibody therapies useful in treating prostate cancer may be selected from the group consisting of abiraterone, enzalutamide, or combinations thereof.

In some embodiments, the active agent delivered through the BBB is a medication that is useful in treating neuroinflammation in the CNS. The active agent useful in treating neuroinflammation in the CNS may target various pathways and mechanisms involved in inflammation. For example, the active agent may be selected from the group consisting of nonsteroidal anti-inflammatory drug (NSAID), corticosteroid, disease-modifying antirheumatic drug (DMARD), biologics, immunosuppressants, cytokine inhibitors, nutraceutical and supplements, antidepressants, anticonvulsants, or combinations thereof.

Nonsteroidal anti-inflammatory drugs (NSAID) are known to, among other things, help reduce inflammation and relieve pain. However, NSAID may have limited effects on chronic neuroinflammation. NSAIDs may be selected from the group consisting of Ibuprofen, Aspirin, Naproxen, or combinations thereof. In certain embodiments, the NSAIDs may include any of the NSAIDs discussed above.

Corticosteroids are described in detail herein. In certain embodiments, the corticosteroid may be corticosteroids may be selected from the group listed above.

Disease-modifying antirheumatic drugs (DMARD) are known to, among other things, be useful in managing autoimmune diseases that causes neuroinflammation, such as MS. In certain embodiments DMARDs are selected from the group consisting of methotrexate, azathioprine, or combinations thereof.

Biologics are known to, among other things, target components of the immune response and be useful in treating conditions like MS and are discussed in further detail above.

Immunosuppressants are known to, among other things, suppress the immune system to reduce neuroinflammation in autoimmune diseases. In certain embodiments, immunosuppressant may be selected from the group consisting of cyclophosphamide, rituximab, or combinations thereof.

Cytokine inhibitors are known to, among other things, block specific cytokines involved in the inflammatory process. For example, cytokine inhibitors may be tocilizumab which may be sold under the tradename Actemra manufactured by Genentech.

Nutraceuticals and supplements are known to, among other things, have anti-inflammatory properties and may support brain health. In certain embodiments, nutraceuticals and supplements are selected from the group consisting of omega-3 fatty acids, curcumin, or combinations thereof.

Omega-3 fatty acids are known to, among other things, promote and maintain brain health and cardiovascular health and reduce the risk of stroke. For example, omega-3 fatty acids, such as docosahexaenoic acid (DHA), are known to be a component of neuronal membrane and contribute to membrane fluidity and functionality. This promotes communication between neurons. Omega-3 fatty acids are also known to have anti-inflammatory properties which may protect the brain from neuroinflammation and influence the expression of genes involved in inflammation and neuro-protection. The regular consumption of omega-3 fatty acids may improve cognitive functions, such a memory, attention, and learning, as well as reducing the risk of cognitive decline, dementia, or Alzheimer's disease by reducing amyloid plaque formation and inflammation in the brain. Further, omega-3 fatty acids are known to promote mental health by influencing neurotransmitter activity and modulating mood, as well as help alleviate symptoms of anxiety and depression. Omega-3 fatty acids are also known to generate new neurons in the brain, such as hippocampus, and enhance synaptic plasticity which are vital for learning and memory. Consuming Omega-3 fatty acids during pregnancy and early childhood are known to promote brain development which improves cognitive and visual development in infants.

Antidepressants are known to, among other things, have anti-inflammatory effects and may be beneficial in treating neuroinflammation. Antidepressants are discussed in further detail above.

Anticonvulsants are known to, among other things, assist in managing pain and have some anti-inflammatory properties. In certain embodiments, anticonvulsants are selected from the group consisting of gabapentin, pregabalin, or combinations thereof.

In some embodiments, the active agent delivered through the BBB is an antiviral that is used treating CNS infections. In certain embodiments, the antiviral may be selected from the group consisting of acyclovir, valacyclovir, ganciclovir, foscarnet, zidovudine, lamivudine, ribavirin, sofosbuvir, or combinations thereof.

Acyclovir may help treat herpes simplex virus (HSV) and a varicella-zoster virus (VZV) infections. For example, acyclovir may be sold under the tradename Zovirax manufactured by Bausch Health Companies Inc.

Valacyclovir may be useful in treating HSV and VZV. For example, valacyclovir may be sold under the tradename Valtrex manufactured by GlaxoSmithKline.

Ganciclovir may be useful in treating cytomegalovirus (CMV) infections and may be sold under the tradename Cytovene manufactured by Roche Palo, Xediton Pharmaceuticals.

Foscarnet may treat CMV infections and resist strains of herpes viruses and may be sold under the tradename Foscavir manufactured by Pfizer Medical.

Zidovudine may be useful in treating HIV/AIDS that can affect the CNS and may be sold under the tradename AZT manufactured by GlaxoSmithKline.

Lamivudine may be effective in treating HIV and Hepatitis B virus. Lamivudine may be sold under the tradename 3TC manufactured by ViiV Healthcare.

Ribavirin may be used in combination with other drugs for viral infections affecting the CNS, such as certain cases of viral encephalitis.

Sofosbuvir may be effective in treating Hepatitis C and impact the CNS in viral infections.

In certain embodiments, the active agent may be selected from the group consisting of antibodies, immunoglobulin, proteins virus, L-dopa, specialized mesenchymal stem cells, anxiolytic, cortisone, steroid, testosterone, estrogen, sleeping medication, antipsychotic medication, pain medication, anti-inflammatory, antibiotics, antiviral, antifungal, immunotherapy, enzymes, proteases, cell fragments, lysozymes, anti-hypertensives, or combinations thereof. For example, cell fragments may be mitochondria.

In some embodiments, the active agent delivered through the BBB promotes and maintains mitochondria which may affect the CNS. Mitochondria are known to, among other things, to provide energy and participate in various cellular processes. Also, mitochondria generate adenosine triphosphate (ATP) through oxidative phosphorylation, which affects brain function, and regulate intracellular calcium levels. This is known to affect neurotransmitter release and synaptic plasticity. Mitochondria are also known to produce reactive oxygen species as a byproduct of respiration and mechanisms to mitigate oxidative stress, which can impact neurons. Mitochondria are known to be involved in the intrinsic pathway of apoptosis, releasing factors that can lead to programmed cell death, which may affect development and disease. The metabolism of fatty acids and amino acids, which is important in maintaining neuronal health, is affected by the mitochondria. The dysfunction of the mitochondria may contribute to the neuroinflammatory process and diseases, such an Alzheimer's, Parkinson's, and Huntington's disease.

Still further embodiments are directed to active agents that are psychedelic. For example, active agents selected from the group consisting of psilocybin, MDMA, or combinations thereof. Psilocybin may be useful in addressing treatment-resistant depression and anxiety disorders. MDMA may be useful for post-traumatic stress disorder (PTSD) therapy.

In on specific embodiment, the active agent delivered through the BBB is the enzyme Klotho. Klotho is, among other things, a multifunctional enzyme expressed in the brain, liver, and kidneys and play a critical role in the regulation of aging, renal function, and the progression of neurodegenerative diseases. Dysregulation of Klotho expression has been known to implicate CNS conditions such as Alzheimer's disease, Huntington's disease, Parkinson's disease, Amyotrophic Lateral Sclerosis (ALS), and traumatic brain injuries.

Klotho has potential applications, among other things, related to treating numerous neurodegenerative and systemic diseases selected from the group consisting of Alzheimer's disease, Parkinson's disease, ALS, traumatic brain injury, or combinations thereof. For example, treating Alzheimer's disease by enhancing Klotho expression may mitigate amyloid-beta accumulation and improve cognitive function. Treating Parkinson's disease by targeted Klotho delivery could protect dopaminergic neurons and reduce oxidative stress. Treating ALS with neurostimulation to increase Klotho levels may provide, among other things. neuroprotection and slow disease progression. Treating traumatic brain injury by modulation the BBB (as discussed herein) and enhancing Klotho's effects could improve neuronal repair and recovery. In addition to treating these diseases, Klotho production and increase may slow down the effects of aging.

Klotho has a molecular weight of approximately 130 kDalton, which renders it unable to cross the BBB effectively. This means that traditional forms of delivery to the brain (e.g., oral or injection) are not feasible therapeutic strategy for delivering Klotho for CNS conditions. In certain embodiments of the present disclosure, Klotho may be delivered to the brain using one or more of the methods disclosed herein. For example, neurostimulation of the SPG may influence the choroid plexus. Neurostimulation of the SPG may comprise using an implantable neurostimulation device strategically placed near the SPG. This device may be able to generate a large electrical field capable of modulating the activity of the choroid plexus. This region of the brain plays an important role in cerebrospinal fluid (CSF) production and potentially in the regulation of Klotho delivery and expression within the CNS.

Methods to promote delivery of Klotho may, for example, be selected from the group consisting neurostimulation of the sphenopalatine ganglion (SPG), stimulation of superior cervical ganglia, or combinations thereof. For example, Klotho introduction and BBB modulation through SPG stimulation may be performed. Any of these methods may further comprise optimizing the stimulation parameters to improve Klotho delivery.

Klotho introduction and BBB modulation through SPG stimulation involves, for example, introducing Klotho directly into the systemic circulation, either through infusion or by targeted electrical stimulation of organs such as the kidneys, where Klotho is naturally expressed. In this approach, the integrity of the BBB could be transiently modulated by stimulating the SPG using a biphasic waveform. For example, employing a biphasic electrical signal, ranging from 5 Hz to 200 Hz, Klotho expression could be improved within the brain. In another example, the biphasic electrical signal is approximately 20 Hz, which has been shown to optimize Klotho activity and enhance its biological effects. In still a further example, the biphasic electrical signal is approximately 10 Hz. Temporary relaxation of the BBB by such a frequency could facilitate the passage of Klotho or its analogs into the CNS, ensuring therapeutic levels of the enzyme reach the target sites within the brain.

Optimizing stimulation parameters may include adjusting the electrical stimulation parameters (frequency, pulse width, and amplitude) to the individual patient needs guided by clinical monitoring, feedback systems, and similar. In certain embodiments, the frequency range is between about 5 and about 200 Hz. For example, the frequency is 10 Hz for BBB relaxation. For example, the frequency is 20 Hz for Klotho expression. Pulse width may be adjusted to improve safety and efficiency in neural activation without causing tissue damage. Amplitude may be calibrated to activate the target ganglia or organs while minimizing off-target effects.

Stimulation of superior cervical ganglia is may also be useful in activating sympathetic nerves. For example, an implant and electrodes may be placed near the superior cervical ganglia to selectively excite sympathetic nerves. Activation of these pathways has the potential to induce systemic or localized Klotho expression through targeted neural stimulation. This approach could provide a mechanism for enhancing Klotho's effects on both peripheral and central systems, potentially bypassing the limitations imposed by the BBB.

The method of delivering or enhancing Klotho through stimulation may be conducted through any method disclosed herein. Although certain examples have been provided herein related to the delivery and introduction of Klotho to the BBB, it will be understood that the described methods and systems are equally applicable to the other active agents discussed herein.

In certain embodiments, sustained release system may be achieved by utilizing hydrogels in combination with one or more of the described active agents. Hydrogels are known to, among other things, be useful for localized and controlled release of therapeutic proteins or genes in the CNS.

While various active agents have been discussed above, it is understood that the skilled artisan will consider many factors when determining the most suitable active agent, such as an antibody, to administer to a patient when treating a disease/disorder. Selecting an antibody, for example, may include a comprehensive evaluation process that may comprise understanding the diseases and/or disorder, selecting an antigen, choosing an antibody type, evaluating efficacy and safety, understanding pharmacokinetics and pharmacodynamics, evaluating clinical considerations, and/or understanding iterative development.

In some or all embodiments, understanding the target disease and/or disorder may comprise pathophysiology, analyzing tumor antigens, or combinations thereof. For example, pathophysiology may include analyzing the underlying mechanisms of the disease including biological pathways involved and the role of specific antigens (such as, proteins, receptors) in disease progression. Analyzing tumor antigens is known in oncology for identifying tumor-associated antigen (TAAs) or tumor-specific antigens (TSAs) is crucial for developing targeted therapies.

Selecting the antigen may comprise antigen identification and/or evaluation of binding affinity. For example, antigen identification includes, among other things, identifying suitable antigens that are overexpressed or uniquely present in the target cells (cancer cells, pathogens, etc.). Evaluation of binding affinity may include understanding the strength of the antibody's binding to the target antigen, as higher affinity can lead to more effective therapies.

Choosing the antibody type may comprise selecting from the group consisting of humanized or fully human antibodies, monoclonal antibodies, bispecific antibodies, antibody-drug conjugates (ADCs), or combinations thereof. For example, selecting humanized vs. fully human antibodies may include determining whether immunogenicity is a concern (as discussed in further detail above). If so, fully human antibodies may be preferred. On the other hand, if specific binding characteristics are necessary, humanized antibodies with targeted CDRs may be more appropriate.

Evaluating efficacy and safety may include reviewing preclinical studies and/or toxicity studies. In preclinical studies, researchers may, among other things, conduct in vitro (cell culture) and in vivo (animal) studies to assess the efficacy of the antibody against the target antigen and to evaluate any potential side effects. For example, toxicity studies may include assessing, among other things, the safety profile and potential adverse reactions in crucial.

Understanding pharmacokinetics and pharmacodynamics may include inspecting the half-life and/or the mechanism of action of the antibody. The half-life is the duration the antibody remains active in the body is important for determining dosing regimens. pegylation may extend the half-life of an antibody. Evaluating the mechanism of action may include evaluating how the antibody exerts its effects such as through ADCC, CDC, or direct neutralization.

Evaluating clinical considerations may include studying and understanding the patient population and/or regulatory factors. For example, patient population includes considering the specific patient demographic, including genetic variations, previous treatments, and underlying health conditions that might affect therapy. Evaluation of regulatory factors may include complying with regulatory guidelines and considerations for clinical trial design to evaluate safety and efficacy in human population.

Understanding iterative development may include utilizing feedback loops and/or adaptive trials. Feedback loops may include modifying or developing new antibodies by reviewing data from clinical trials to improve efficacy, safety, or targeting capabilities. Adaptive trials may be designed to adapt based on interim results, allowing researchers to switch to different antibody types if initial candidates do no perform as expected.

The selection of the most suitable type of antibody for a specific therapy is a multi-faceted process involving a blend of scientific research, clinical insights, and regulatory considerations. It will be understood that the goal is to maximize therapeutic efficacy while minimizing potential side effects, leading to more effective and personalized treatment options for patients.

In other embodiments, the active agent delivered through the BBB may be chemically modified. Chemical modification may be effective, in certain embodiments, in developing stem cell therapies for various diseases such as degenerative conditions, injuries, and generic disorders.

In certain embodiments, chemical modifications may be selected from the group consisting of glycosylation, pegylation, site-specific conjugation, FC engineering, stabilization techniques, or combinations thereof.

Glycosylation may influence an antibody's pharmacokinetics and pharmacodynamics. For example, some glycoforms may enhance an antibody's ability to activate complement pathways, leading to improved tumor cell lysis.

Pegylation may comprise adding PEG to an antibody to create a larger molecular weight, which helps to shield the antibody from the immune system and prolong its circulation time. Pegylation improves solubility and reduces clearance by the kidneys and enhance the therapeutic window.

Site-specific conjugation allows for the precise attachment of cytotoxic drugs to an antibody at specific locations which ensuring that the active agent is delivered directly to the target cells. An advantage of site-specific conjugation is the minimizing of off-target effects and enhancement of the therapeutic index of the active agent.

FC Engineering comprises altering an amino acid sequence in the FC region to enhance its binding affinity to FC receptors or complement proteins. Such FC engineering may result in improved FC interactions. This leads to enhanced immune responses, such as increased ADCC or CDC, which can be particularly useful in treating cancers.

Stabilization techniques may include introducing disulfide bonds or using stabilizing excipients during formulation to enhance the stability of antibodies or active agents during storage and handling. Stabilization may be important for maintaining the efficacy of antibodies, particularly those that are sensitive to temperature and pH changes.

Certain other chemical modification techniques may be selected from the group consisting of epigenetic modifications, small molecule compound addition, biomaterial and extracellular matrix (ECM) modifications, gene editing, cytokine and growth factor modification, chemical induction of reprogramming, or combinations thereof.

Epigenetic modifications may be used to alter the epigenetic landscape of stem cells to improve their differentiation and regenerative capabilities. For example, epigenetic modifications may comprise the use of chemical compounds that modify DNA methylation and histone acetylation in order to influence stem cell behavior.

Small molecule compounds may be used in chemical modification in order to promote stem cell pluripotency or directed differentiation. For example, small molecule compounds such as CHIR99021 or PD0325901 may activate signaling pathways that maintain stemness or guide cells toward specific lineages.

ECM modification may be undertaken by utilizing biomaterials which mimic the stem cells niche and influence stem cell behavior. Chemical modifications to these materials can enhance cell adhesion, proliferation, and differentiation.

Gene editing techniques, such as CRISPR/Cas9 technology can be used to modify genes in stem cells and allow for the correction of genetic disorders or optimization for transplantation.

Cytokine and growth factor modification may comprise the addition of certain cytokines and growth factors. The addition of these cytokines and growth factors can chemically modify the environment of stem cells in order to enhance their proliferation and differentiation into desired cell types.

Chemical induction of reprogramming may include, for example, employing small molecules to reprogram somatic cells into induced pluripotent stem cells (iPSCs), which can then be differentiated into specialized cells for therapy.

The method described herein can be used for therapy for treating concussion or CTS or other brain injuries or other CNS disorder or relieve or reduce symptoms. It may be used to treat agitation or aggressive or other dysfunctional behavior. If identified early, the method can be used in therapies in utero, which can be used to treat cerebral palsy or neonatal hypoxia, or treat neonate in late term pregnancy for genetic diseases or deficiencies. For example, such therapies would involve delivering enzymes, hormones, DNA or RNA into brain tissue of embryo or fetus. In one example, the biologic agent may be used in conjunction with gene editing tools, such as CRISPR-Cas9 technology, to enable in utero gene editing. Diseases such as osteogenesis imperfect to mutations to Huntingtons or infections such as toxoplasmosis or meningitis can be treated using the methods and systems described herein. The methods and systems can be used to enhance neuroplasticity and help CNS tissue or nerve fibers regrow or heal after anoxia or stroke or chemical, pharmaceutical injury, as non-limiting examples. In one or more embodiments, the method described herein may be used to treat memory loss, cognitive impairment, auto immune disease of CNS, neurodegenerative disorders, ALS, CTE, Parkinson's, and/or vasospasms especially after aneurysms. In one or more embodiments, the method described herein may be used for delivery of one or more of the following across the BBB: monoclonal antibodies, chemotherapy agents, stem cells and biologics, and/or nutrients like lipids, fatty acids, starches, longer chain proteins.

In some embodiments, the disclosed delivery methods and systems may be paired with therapies that use CRISPR (Clustered Regularly Interspaced Short Palindromic Repeats) technology. In one embodiment CRISPR may be used to treat CNS disorders. For example, CNS disorders that CRISPR may be useful in treating may be selected from the group consisting of neurodegenerative disease, genetic disorder, brain tumor, epilepsy, mental health disorder, neuroinflammatory condition, or combinations thereof.

Neurodegenerative diseases that may be treated with therapies that use CRISPR include, for example, those selected from the group consisting of Huntington's disease, Alzheimer's disease, Parkinson's disease, or combinations thereof. For example, CRISPR may be used to treat Huntington's disease by targeting and editing the mutated HTT gene responsible of the disease. In other examples, therapies that use CRISPR may be used to treat Alzheimer's disease deleting or modify genes associated with amyloid plaque formation (e.g., APP, PSEN1, etc.). In still further examples, therapies that use CRISPR may be used to treat Parkinson's disease by targeting genes involved in alpha-synuclein aggregation.

Genetic disorders that may be treated with therapies that use CRISPR include, for example, those may be selected from the group consisting of spinal muscular atrophy (SMA), Fragile X Syndrome, or combinations thereof. For example, therapies that use CRISPR may be used to treat SMA by correcting mutations in the SMN1 gene to promote the production of survival motor neuron protein. In another example, therapies that use CRISPR may be used to treat fragile X syndrome by targeting the FMRI gene to reactivate gene expressions in affected individuals.

In certain embodiments, therapies that use CRISPR may be used to treat brain tumors by targeting oncogenes to knock out genes that drive the growth of specific brain tumors, such as glioblastoma.

In other embodiments, therapies that use CRISPR may be used to treat epilepsy using gene editing of ion channel disorders by correcting mutations in ion channel genes that contribute to certain forms of epilepsy.

In various embodiments, therapies that use CRISPR may be used to treat mental health disorders, such as depression and anxiety, by modifying genes associated with neurotransmitter systems (e.g., serotonin receptors).

In one embodiment, therapies that use CRISPR may be used to treat neuroinflammatory conditions by targeting genes involved in immune regulation and inflammation within the CNS.

In certain embodiments, CNS disorders may be treating using therapies that use CRISPR by creating animal models of CNS diseases for research and drug testing.

In still further embodiments, the therapies that use CRISPR technology to treat CNS disorders may be combined with the other therapies, delivery systems, or drugs disclosed herein, to enhance the treatment effectiveness. For example, in combination with stem cell therapy and/or small molecule drugs. In another example, therapies that use CRISPR technology to treat CNS disorders may be combined with AAV (Adeno-Associated Virus) Vectors for targeted delivery of gene-editing components into specific brain cells.

Although certain BBB stimulation devices are discussed herein, it will be understood that alternative devices may be used for neuromodulation alone or in combination with the described BBB stimulation devices, and are within the scope of the present disclosure. In certain embodiments, BBB stimulation devices and other devices useful for used for neuromodulation may be selected such that the device modulates blood flow between the body and brain and/or stimulates the SPG. In other embodiments, the BBB stimulation devices and other devices useful for used for neuromodulation may be used in connection with an implant placed within the body (as discussed in further detail herein).

In certain embodiments, neuromodulation devices may be used in combination with active agent delivery through the BBB. For example, devices which are known to control permeability, autonomic, the SPG, vagus, sympathetic chain, and/or spinal cord. In certain specific embodiments, the alternative devices may be neuromodulation devices which are used to alter nerve activity through targeted delivery of electrical stimulation or pharmacological agents. For example, nueromodulation devices may be selected from the group consisting of deep brain stimulation (DBS) systems, spinal cord stimulators (SCS), transcranial magnetic stimulation (TMS) devices, transcranial direct current stimulation (DCS) devices, vagus nerve stimulation (VNS), peripheral nerve stimulation (PNS), responsive neurostimulation (RNS), bioelectronics medicine devices, visual prosthesis devices, brain-computer interface devices, or combinations thereof. In other embodiments, additionally devices selected from the group consisting of intrathecal drug delivery systems, cochlear implants, retinal implants, sacral nerve stimulators, and combinations thereof may be used in combination with any of the described methods or systems. In still additional embodiments, devices selected from the group consisting of Braingate devices, Neurolink systems, and combinations thereof may be used in combination with any of the described methods or systems.

DBS devices are known to be, among other things, implanted devices that deliver electrical impulses to specific brain regions and useful in treating conditions like Parkinson's disease, essential tremor, and/or dystonia. In certain embodiments, DBS systems are selected from the group consisting of Medtronic Activia, Boston Scientific Vercise, Abbott Infinity, or combinations thereof.

SCS devices are known to be, among other things, devices implanted in the spine that deliver electrical impulses and useful in chronic pain management. In certain embodiments, SCS devices may be selected from the group consisting of Medtronic Intellis, Medtronic RestoreSensor, Boston Scientific Spectra WaveWriter, Boston Scientific Precision, Abbott Proclaim, or combinations thereof.

TMS devices are known to be, among other things, non-invasive devices that use magnetic fields to stimulate nerve cells in the brain and useful in treating depression or other mood disorders. In certain embodiments, TMS devices are selected from the group consisting of Neuronetics NeuroStar, BrainsWay Deep TMS, eNeura SpringTMS, or combinations thereof.

tDCS devices are non-invasive devices that deliver low electrical currents to the scalp, often used in research settings, and known to, among other things, modulate neuronal activity.

VNS devices are known to be, among other things, implantable devices that stimulate the vagus nerve and useful in treating epilepsy and depression. In certain embodiments, the VNS device is a LivaNova VNS Therapy System.

PNS devices are known to be, among other things, implantable devices that stimulate peripheral nerves and useful in various pain conditions and prevent seizures. In certain embodiments, PNS devices may be selected from the group consisting of Stimwave Freedom, Bioness L300, Nuvectra ALPHA Systems, or combinations thereof.

RNS devices are known to, among other things, be useful in epilepsy management. In certain embodiments, the RNS devices is a NeuroPace RNS System.

Bioelectronics medicine devices are known to, among other things, interface with the nervous system to modulate organ function and modulating nerve activity useful in various conditions and diseases.

Visual prosthesis devices are known to, among other things, restore vision by stimulating the retina or visual cortex.

Brain-computer interface devices are known to, among other things, control devices using brain activity. In certain embodiments, brain-computer interface devices may be selected from the group consisting of Synchron Stentrode, Blackrock Neurotech Neuroprosthetics, Neurable Brain-Computer Interface Technology, or combinations thereof.

Cochlear implants are devices that are known to, among other things, provide a sense of sound to individuals with severe hearing loss by stimulating the auditory nerve. In certain embodiments, the Cochlear implant is a Cochlear Limited cochlear implant.

The Brainsgate device is known to, among other things, modulate the vagus nerve to promote neurovascular recovery and brain function after an ischemic stroke. The Brainsgate device may include specific parameters and mechanisms that are known to effect vasodilation. These specific parameters and mechanisms may be selected from the group consisting of simulation protocol, pulse width, current amplitude, duration of stimulation vasodilation mechanism, clinical studies, safety and efficacy, and combinations thereof. Stimulation protocol is known to, among other things, involve a frequency, for example, between about 20 from about 30 Hz which has been shown to activate the vagus nerve effectively. Pulse width is known to, among other things, be a part of determining the type and extent of neuronal activation. For example, pulse width may be between about 100 and 500 microseconds. Current amplitude is known to, among other things, stimulates the vagus nerve without causing discomfort. For example, the current amplitude may be between about 0.5 to about 3 mA. Duration of stimulation, for example, may last from about 3 minutes to about 75 minutes. Vasodilation mechanism is known to, among other things, induce vasodilation through the release of neurotransmitters and neuropeptides that modulate vascular tone which is known to increase blood flow and improve oxygenation in the brain tissue. The neuropeptide may be, for example, acetylcholine. Clinical studies involving the Brainsgate device is known to, among other things, measure outcomes such as cerebral blood flow, neurological function, and recover metrics after ischemic events.

Figure 2:
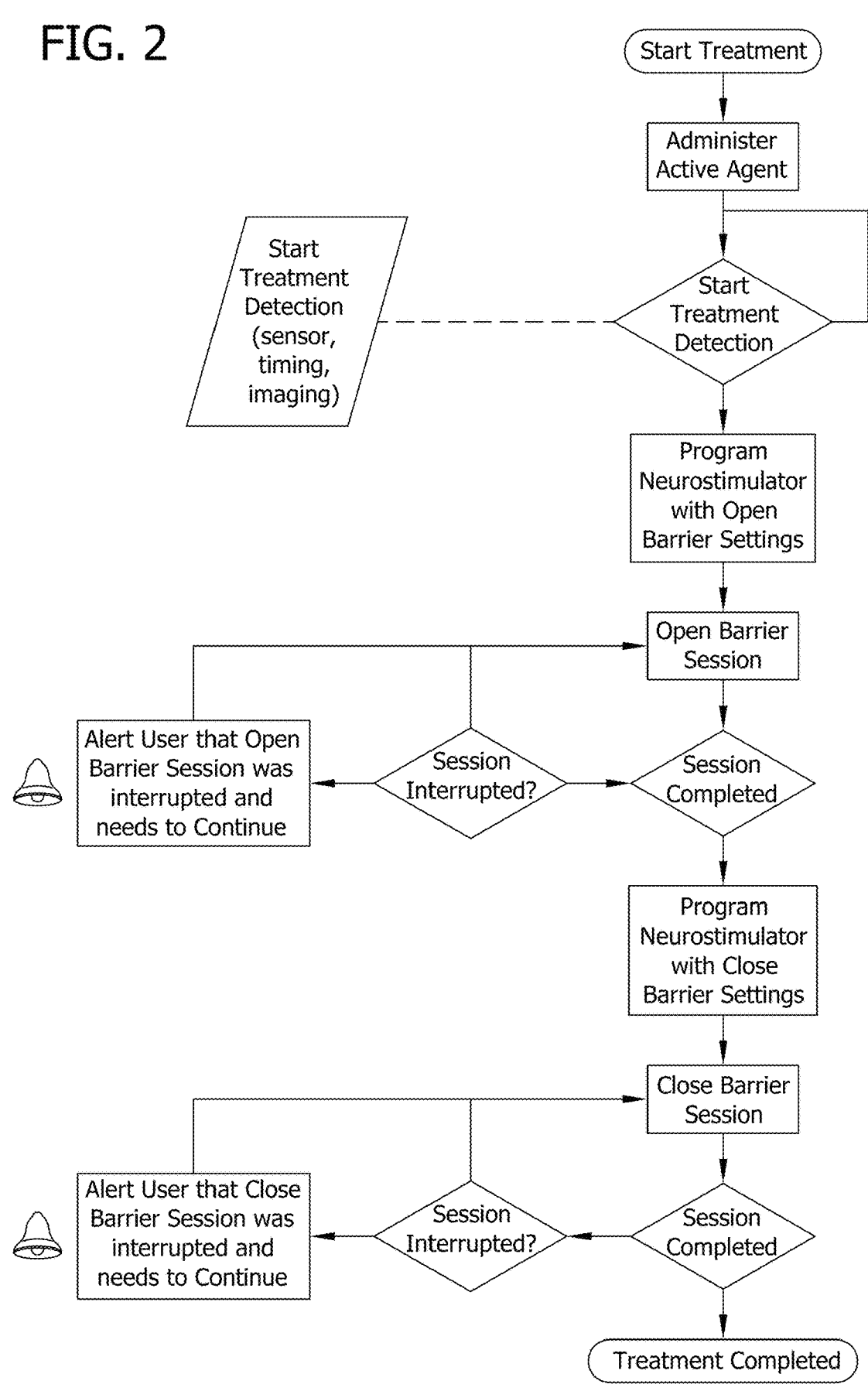
FIG. 2 is a schematic representation of one embodiment of a method of treating tissue by opening and closing a tissue barrier.

In one example, a stimulation device for affecting the BBB may be designed and constructed to deliver electrical stimulation to the sphenopalatine ganglion (SPG) or other nerve or ganglion, for example. Suitable devices and methods for electrically stimulating the SPG are described in U.S. Ser. No. 17/183,293, filed Feb. 23, 2021; U.S. Ser. No. 17/327,442, filed May 21, 2022; U.S. Ser. No. 12/434,457, filed May 1, 2009; U.S. Ser. No. 13/784,452, filed Mar. 4, 2013; and U.S. Ser. No. 15/362,124, filed Nov. 28, 2016; U.S. Pat. No. 8,055,347, filed Aug. 17, 2006; each of which are incorporated by reference herein in its entirety. FIGS. 1 and 2 is a reproduced figure of a suitable stimulator, also called an electrode assembly herein, disclosed in U.S. Ser. No. 12/765,712, filed Apr. 22, 2010, the entirety of which is incorporated by reference. The electrode assembly 200 of this embodiment comprises of an electrode body 200*a*, an integral electrode lead 200*b* including electrodes 201 spaced apart by insulation portions 202 (e.g., polymer material of the electrode lead), and an integral fixation apparatus 200*c*. The electrode assembly 200 can be implanted such that the electrode body 200*b* is positioned medial to the zygoma 205 on the posterior maxilla 206 within the buccal fat pad of the cheek, and the integral fixation apparatus 200*c* is anchored to the zygomaticomaxillary buttress 203, such as by using standard craniomaxillofacial bone screws, for example. The integral electrode lead 200*b* can be placed within the ptery-gopalatine fossa, or more specifically, in very close proximity to the sphenopalatine ganglion 204. The electrode assembly 200 of this embodiment can be an inductively powered device by a hand-held device having the necessary micro-electronics to store programmable stimulation parameters, deliver electrical stimulation per the programmed parameters and to allow bi-directional telemetry to enable communication with an external controller.

The micro-electronics of the electrode assembly 200 can be housed in the electrode body 200*a*, a hermetic enclosure that protects the micro-electronics from fluid ingress when implanted within the body. The electrode body 200*a* can further include an electronics enclosure, a micro-electronics assembly, a monolithic feed-through assembly, and a lead interconnect assembly, and the electrode body 200*a* can be molded with a protective outer layer. Electrical stimulation can be carried from the micro-electronics to one or more of the stimulating electrodes 201 through the electrode lead 200*b*. The electrode lead 200*b* can be connected to the electrode body 200*a* through a series of feed-through assemblies. In certain embodiments, the electrode assembly 200 may be modified according to the teachings set forth below herein.

In one embodiment, the electrode assembly 200 is powered inductively by an external hand-held device or hand-held controller 250 (FIGS. 5 and 15-18). In one example, a suitable hand-held controller 250 is described in U.S. Ser. No. 15/362,124, filed Nov. 28, 2016, the entirety of which is incorporated by reference. This hand-held controller 250 electronics, micro-electronic components, and integrated circuits necessary to store settings, parameters, and other data. During a therapy session, the electrode assembly 200, powered by the hand-held controller 250, in one example, delivers electrical stimulation per the stimulation parameters stored on the electrode assembly. Each of the electrodes 201 may be controllable independently, which allows the user to select which electrodes will serve as anodes and which electrodes will serve as cathodes in any combination. The electrode assembly 200 can apply the stimulation therapy in accordance with the stimulation parameters stored on the electrode assembly. Additionally, the electrode assembly 200 can acquire and transmit to the hand-held controller 250 therapy session data gathered during a therapy session. The electrode assembly 200 includes a non-volatile memory for storing the stimulation parameters and other clinical trial related information.

The hand-held controller 250 provides inductive power to the electrode assembly 200 and communicates (e.g., via radio frequency) with the electrode assembly. Through this communication, the hand-held controller 250 can access settings and parameters stored on the electrode assembly 200 and also record therapy session data (in real-time or at a predetermined time). For example, in an embodiment used in a clinical trial, the hand-held controller 250 may record therapy session data in real time while also accessing clinical trial specific data (e.g., trial type, specific questions to be asked, therapy randomization strings, language settings, etc.) in real-time or at some predetermined time before, during, or after the therapy session. In another example, in an embodiment used in a post-market patient usage, the hand-held controller 250 may record therapy session data in real time while also recording post-market specific data (e.g., specific questions to be asked) in real-time or at some predetermined time before, during, or after the therapy session.

Another suitable device is offered by Brainsgate, for example as illustrated in U.S. Ser. No. 11/465,381 filed Aug.

17, 2006, which is incorporated by reference herein in its entirety. Such devices include electrodes for delivering the electrical stimulation. A suitable frequency for stimulation may be below 60 Hz, such as 10 to 40 Hz or 10 to 30 Hz. The electrodes of the stimulation device can be self-guided or include an ingrowth portion—a roughened or porous or coated surface to remain fixed at a location despite body movement if long term requires or could be partially or completely biodegradable. The stimulation device can include ASICS (which can include a waveform generator, patient safety circuitry, volatile and non-volatile memory, communication modules, sensors and wave form processing circuitry, and cybersecurity functions) or an ingrowth surface or be stabilized with one or more suture anchors or other fasteners couple to tissue or bone for stability.

Other stimulation devices include magnetic stimulation, mechanical stimulation or ultrasound stimulation. Suitable device and methods for ultrasound stimulation is described in U.S. Ser. No. 15/011,156, filed Jan. 29, 2016, the entirety of which is incorporated by reference. In other embodiments, chemical stimulation may be used. For example, acidic or basic fluid, or serotonin, serotonin reuptake inhibitors, or serotonin blockers, or epinephrine or epinephrine blockers, or other chemicals to facilitate stimulation of SPG or otherwise affect BBB porosity (e.g., opening and closing) either at SPG or systemically through an IV or locally with a catheter delivered to the BBB. This chemical stimulation may be used in conjunction with or apart from electrical or other energy-based stimulation.

In one example, direct and indirect modulation of a membrane (e.g., BBB) may be performed concurrently, sequentially, or in an overlapping procedure. For example, direct modulation of a membrane (e.g., BBB) through direct stimulation (e.g., external ultrasound) of the membrane (e.g., BBB) may be used to selectively increase and/or decrease permeability of a membrane (e.g., BBB) at a selected, localized area or region, and electrostimulation at a remote location (e.g., SPG) of the membrane to indirectly modulate a membrane (e.g., neuromodulation of BBB) to increase and/or decrease permeability of the membrane (e.g., BBB) over a larger (broader) area or region. In a non-limiting example, ultrasound may be used to directly modulate the BBB at a selected, localized area or region of the brain, prior to, after, concurrent with, or overlapping with electrostimulation of the SPG to indirectly modulate the BBB over a larger area or region of the brain. This process may be combined with delivery of any active agent described herein or other active agents at selected times during the process of increase and decreasing the BBB or other membrane.

The stimulation device may be operated with wearables or remote patient monitoring systems. Encrypted technology that goes through mobile devices wireless or hard wired to cloud may be used to process information to patient provider or insurance company SPG stimulator or external handpiece that controls frequency, power, wavelength etc. can have Bluetooth for data in or out Electronics can be part biodegradable or upgradeable.

The stimulation device may be used with AI systems or other software to add functionality or build up implant to decide optimal function and what to add to implant either internally or to external device. AI can be used to optimize frequency, wavelength, power, and timing with or without other treatment like medical treatment or oxygen or if multiple frequencies or wavelength or power used for an individuals' treatment. Training data for AI software may be gathered from multiple patients' data or a synthetic data set could be created. Additional data may be patient anatomy, biologic functions like food, pulse, oxygen levels, temperature, implant design, electrode design and location and feedback sensor (such as EEG, MEG, MRI, imaging or other invasive and non-invasive sensors) or patients' response notes by wearable or iPhone or video. Teachings described in U.S. Ser. No. 15/299,981, filed Oct. 21, 2016, and U.S. Ser. No. 16/118,025, filed Aug. 30, 2018 (the entirety of each of which is hereby incorporated by reference), are pertinent to these features.

In one or more examples, the agent delivery device (e.g., catheter) can be inserted or implanted and operated using suitable techniques. For example, the agent delivery device may be inserted or implanted using MIS approaches, or an expanding access device, or magnetic or RF guided catheter or guide wire, or a deposition (aerosol) drug delivery system. The agent delivery device can guide or be used with biplanar fluoroscopy or MRI or PET or EM, or with a dye or radiologic marker or technetium 99 or other radioisotope to follow, guide, monitor, direct treatment. One example of a suitable agent delivery device and method is described in U.S. Ser. No. 17/170,710, filed Feb. 8, 2021, the entirety of which is hereby incorporated by reference.

As described in the '710 application, and shown in FIGS. 19-22, a tissue distraction system may be used with the agent delivery device. The distraction system 260 includes a multi-channel catheter/cannula 262, an expandable balloon 264, a balloon inflation tube 266, and a drug delivery tube 268. In use, the system 260 is inserted in tissue adjacent a body region 272 which requires the administration of one or more medicaments. During insertion, the balloon 264 is deflated to minimize tissue displacement. Once positioned, the balloon 264 is inflated to distract tissue. The distal end of the drug delivery tube 268 is positioned proximal from the balloon 264 such that medicament may be administered to tissue located proximal to the balloon 264.

A distraction drug delivery system 270 is similar to the system 260 and includes similar structural features. In use, the system 270 is inserted in tissue adjacent a body region 272 which requires the administration of one or more medicaments. During insertion, the balloon 264 is deflated to minimize tissue displacement. Once positioned, the balloon 264 is inflated to distract tissue. The distal end of the drug delivery tube 268 is positioned distal from the balloon 264 such that medicament may be administered to tissue located distal to the balloon 264. The systems 260/270 allow therapeutic and pharmaceutical agents to be delivered to a greater tissue surface area since the tissue is spaced apart by the inflated balloon.

A drug dispersion member 280 may be used for administering one or more medicaments to the surface of tissue. The dispersion member 280 includes porous material 284 for allowing medicaments to flow therethrough. The member 280 may be made of foam, fabric, polymer, metal, ceramic, composite, or combinations thereof. It may be biodegradable or biostable. The dispersion member 280 may include a channel 286 dimensioned for receiving a delivery tube 288 of a drug delivery system previously described. The member 280 is implanted in tissue 282 such that the outer surface of the member contacts the tissue surface. The delivery tube 288 is inserted in the channel 286 of the member 280. The tube 288 may include microenvironment-controlling devices, such as sensors 14, magnets 102, heating/cooling units 18, drug ports 16, and pressure ports 19. With the tube positioned, one or more medicaments may be expelled from the tube 288 and captured by the porous material 284 of the disbursement member 280. The member and its pores function as a wick to carry the agent(s) to the adjacent tissue. The microenvironment of the adjacent tissue may be measured, changed, and monitored by the dispersion member.

A remote monitoring system may be used. A suitable patient monitoring system is described in U.S. Pat. No. 9,763,581, the entirety of which is incorporated by reference herein. As described in the '581 patent, one can externally monitor these drug deliveries systems or internally monitor them. The delivery systems could be used with an implantable pump or implantable blood chemistry sensor. A wireless readout from the pump or sensor could attach, for example, to a wrist watch which would monitor the compliance through a digital readout. A patient could monitor their own blood chemistries or response to particular medications and then these results would be broadcast to physician, extended care, nurse practitioner, nurse, insurance carrier, etc. This would then monitor the changes to a specific drug and then monitor the serum chemistries, for example, blood sugar, etc. These are monitored and then the patient can be monitored through a wireless format to see how they respond to certain medications and have an instant readout through this chemistry monitor without actually having the patient in the office or in the hospital. If the response is not as desired, the delivery protocol can be remotely changed based on the measurements.

The system may be used with video documentation systems, as described in U.S. Ser. No. 17/401,898, filed Aug. 13, 2021, the entirety of which is incorporated by reference.

The neuromodulation system may implement specialized stimulation waveforms and parameter configurations that enable precise control over BBB permeability through targeted SPG activation. These optimized stimulation protocols may facilitate controlled opening and closing of the blood-brain barrier to enable therapeutic delivery of pharmaceuticals, biologics, stem cells, or other therapeutic agents while possibly also providing mechanisms for drainage of toxic degradation products from brain tissue. The stimulation parameters may be calibrated to achieve desired permeability changes while maintaining tissue safety and preventing adverse electrochemical reactions at the electrode-tissue interface.

Therapeutic agent delivery protocols may coordinate stimulation parameters with drug infusion or delivery timing to optimize therapeutic effectiveness while minimizing systemic exposure. For small molecule pharmaceuticals with molecular weights below 500 daltons, moderate barrier opening achieved through lower stimulation intensities may provide adequate permeability for effective delivery. Larger therapeutic agents such as antibodies with molecular weights approaching 150 kilodaltons may require more extensive barrier opening achieved through higher stimulation intensities or longer stimulation durations. Cellular therapies such as mesenchymal stem cells may require maximal barrier opening protocols that provide sufficient permeability for cellular migration while maintaining cell viability during the delivery process.

The stimulation parameters may be personalized for individual patients through systematic evaluation of physiological responses and therapeutic outcomes during initial treatment sessions. Baseline impedance measurements may guide initial parameter selection by providing information about tissue characteristics and electrode positioning quality. Patient-specific optimization protocols may systematically vary stimulation parameters while monitoring physiological responses such as neural activation patterns, cardiovascular changes, or other biomarkers that indicate barrier modulation effectiveness. Machine learning algorithms, as explained below, may analyze historical treatment data to identify parameter combinations that provide optimal therapeutic outcomes for specific patient populations or clinical indications. The personalized parameter optimization process may continue throughout the course of treatment to accommodate changes in tissue properties, disease progression, or therapeutic objectives that influence optimal stimulation characteristics.

Figure 3:
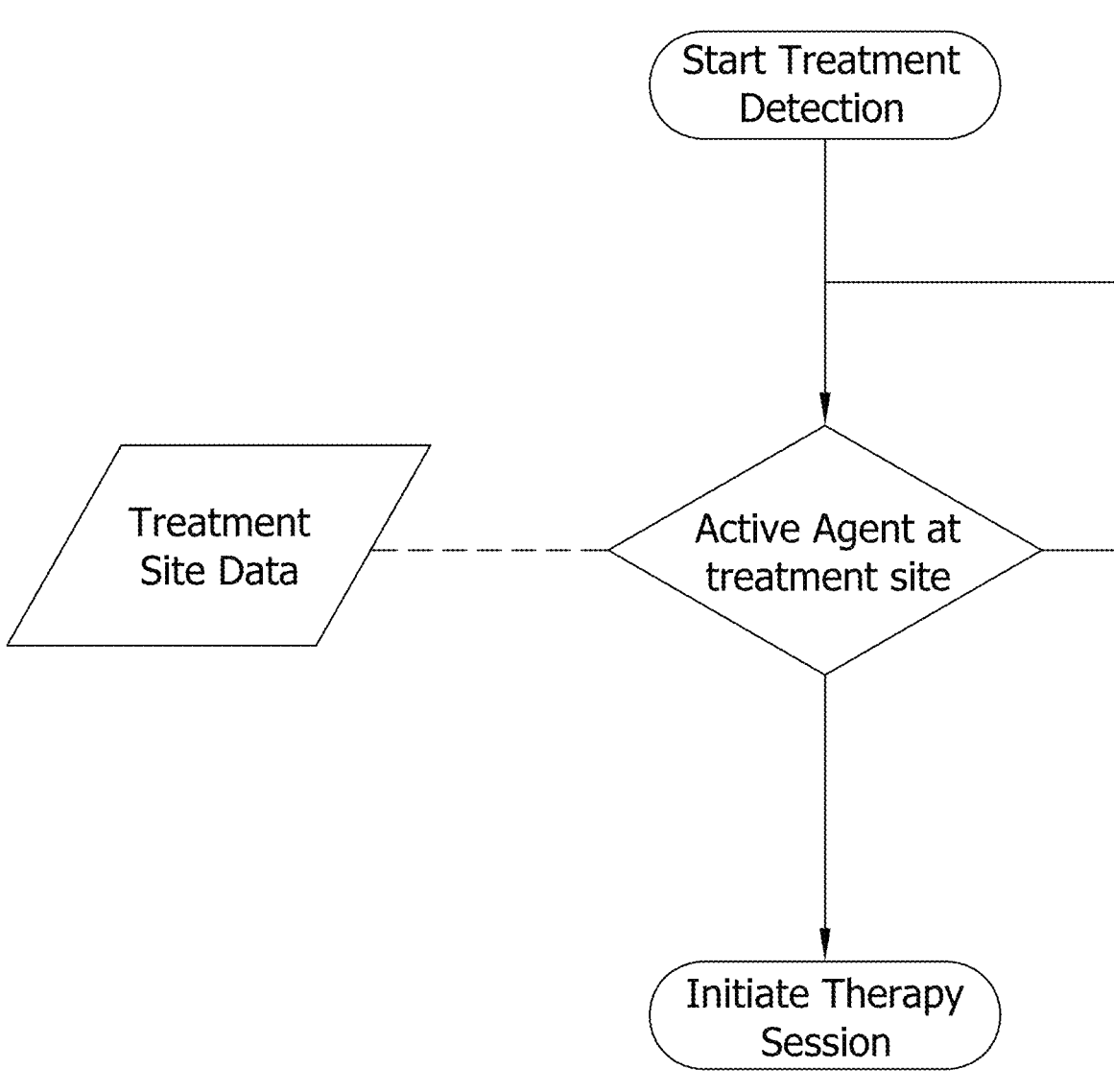
FIG. 3 is a schematic representation of method of detecting when active agents are ready to be passed through the barrier.

An exemplary method of treating a patient by affecting porosity of a barrier of the patient is shown in FIG. 2. An active agent may be administered to the patient (such as by any method described above or other method) before applying the stimulation signal (e.g., electrical signal) to a body portion (e.g., neuron cell bodies-ganglia-such as SPG) to affect porosity of the barrier (e.g., BBB). Referring to FIG. 3, after administrating the agent, a predetermined parameter may be measured and analyzed to determine initiation of stimulation at a subsequent step to "open" the barrier. As non-limiting examples, the predetermined parameter may be time elapsed, delivered active agent dosage, active agent concentration in the body (e.g., around or at the barrier), change in active agent concentration, change of concentration of a substance (e.g., a brain substance) in blood of the subject indicating that the substance has passed through the BBB and into the blood stream, or other parameters. For example, an internal sensor, blood analysis, and/or or imaging may be used to determine concentration of the active agent. In one embodiment, the timing could come directly from integration of an infusion pump to the system. By monitoring the flow rate of the active agent, the delivery time of the therapeutics to the brain can be predicted. As explained below, in one example, a sensor may be integrated with the stimulator or other implant. In another example, a dye or other tag could be used with the active agent and imaging can be used to determine concentration or presence of active agent at the barrier. An imager may be independent or integrated into the system or be independent from the system.

Figure 4:
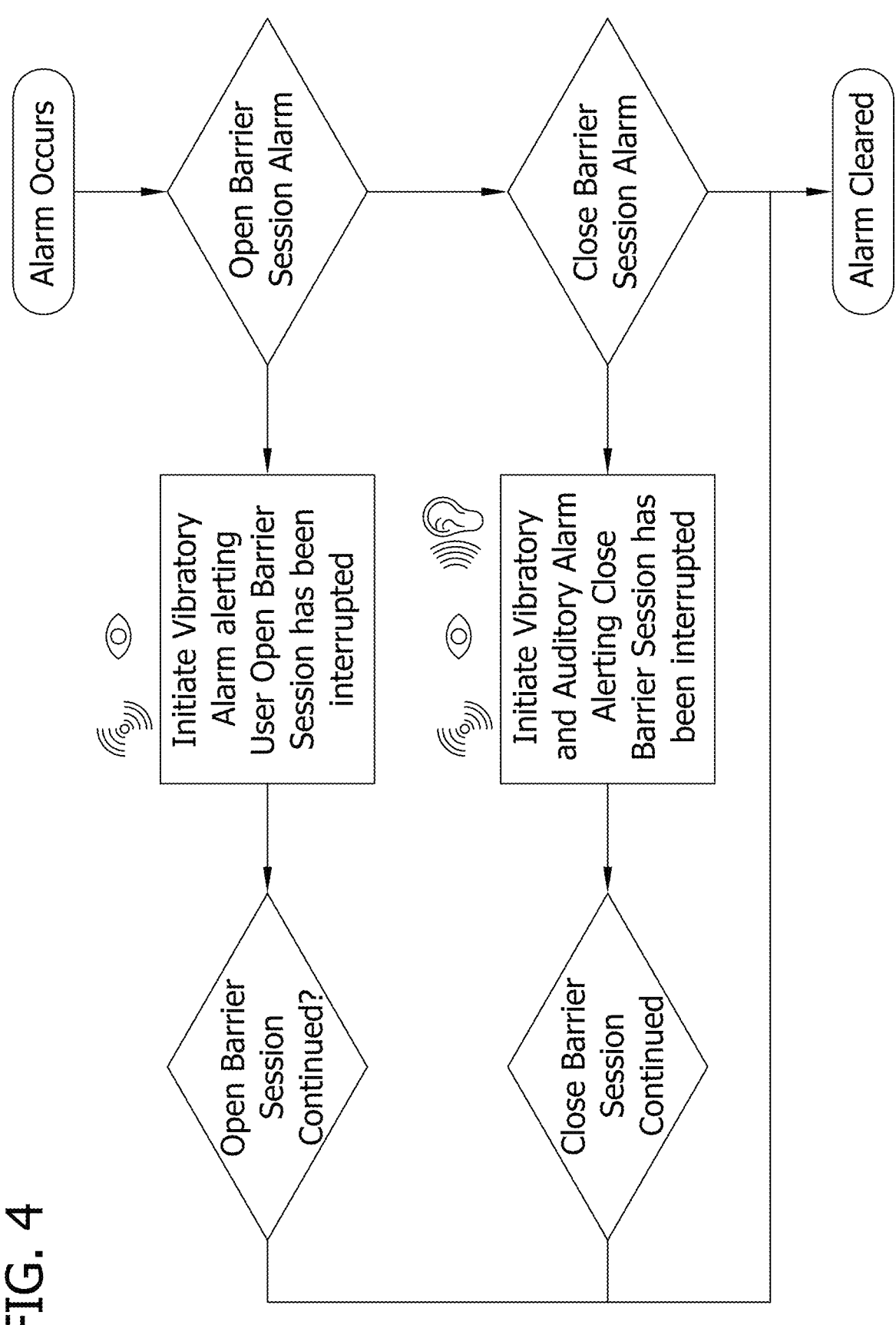
FIG. 4 is a schematic representation of a method of opening and closing the tissue barrier.
Figure 5:
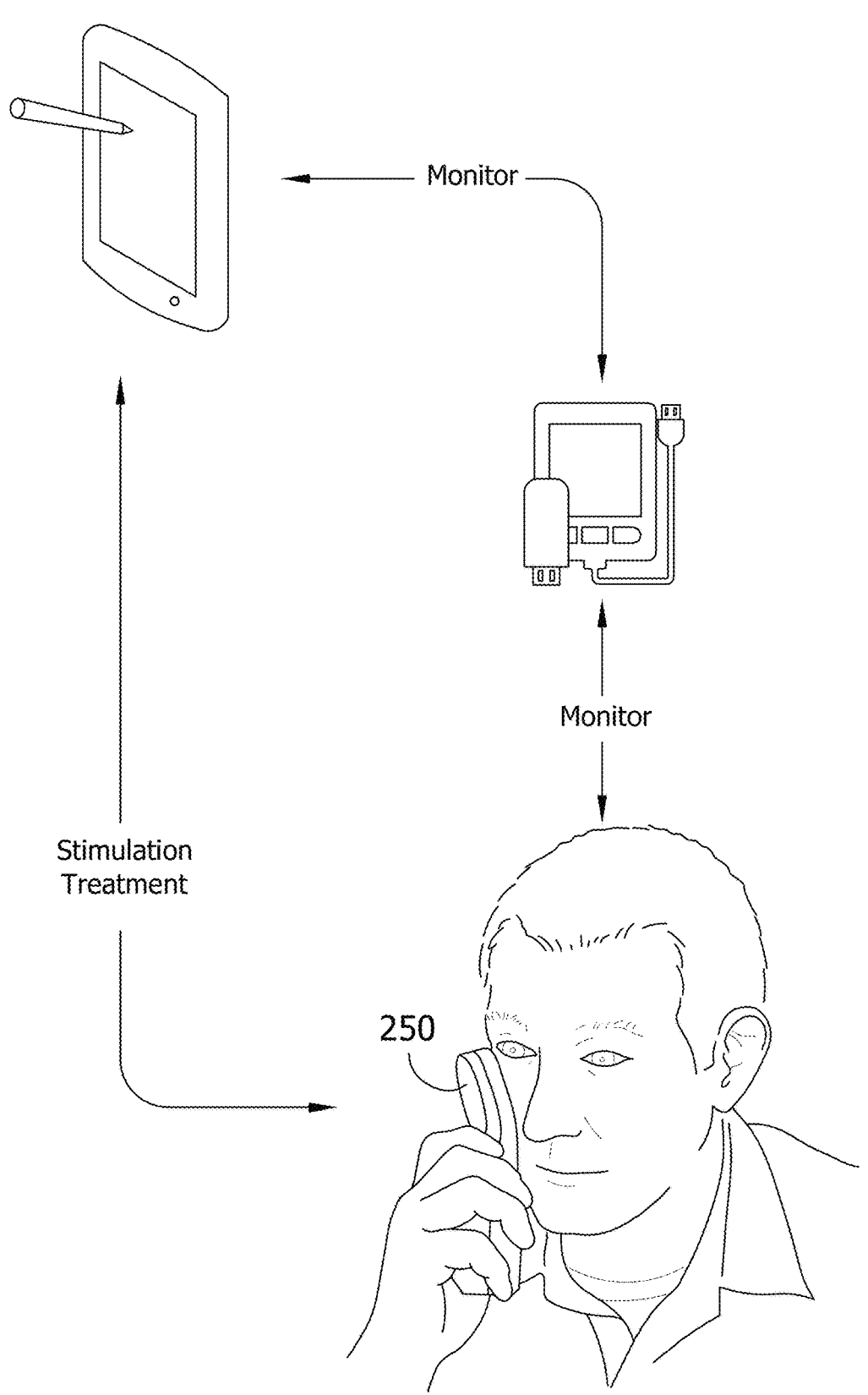
FIG. 5 is an embodiment of a system for opening and closing the BBB by stimulating the SPG.
Figure 6:
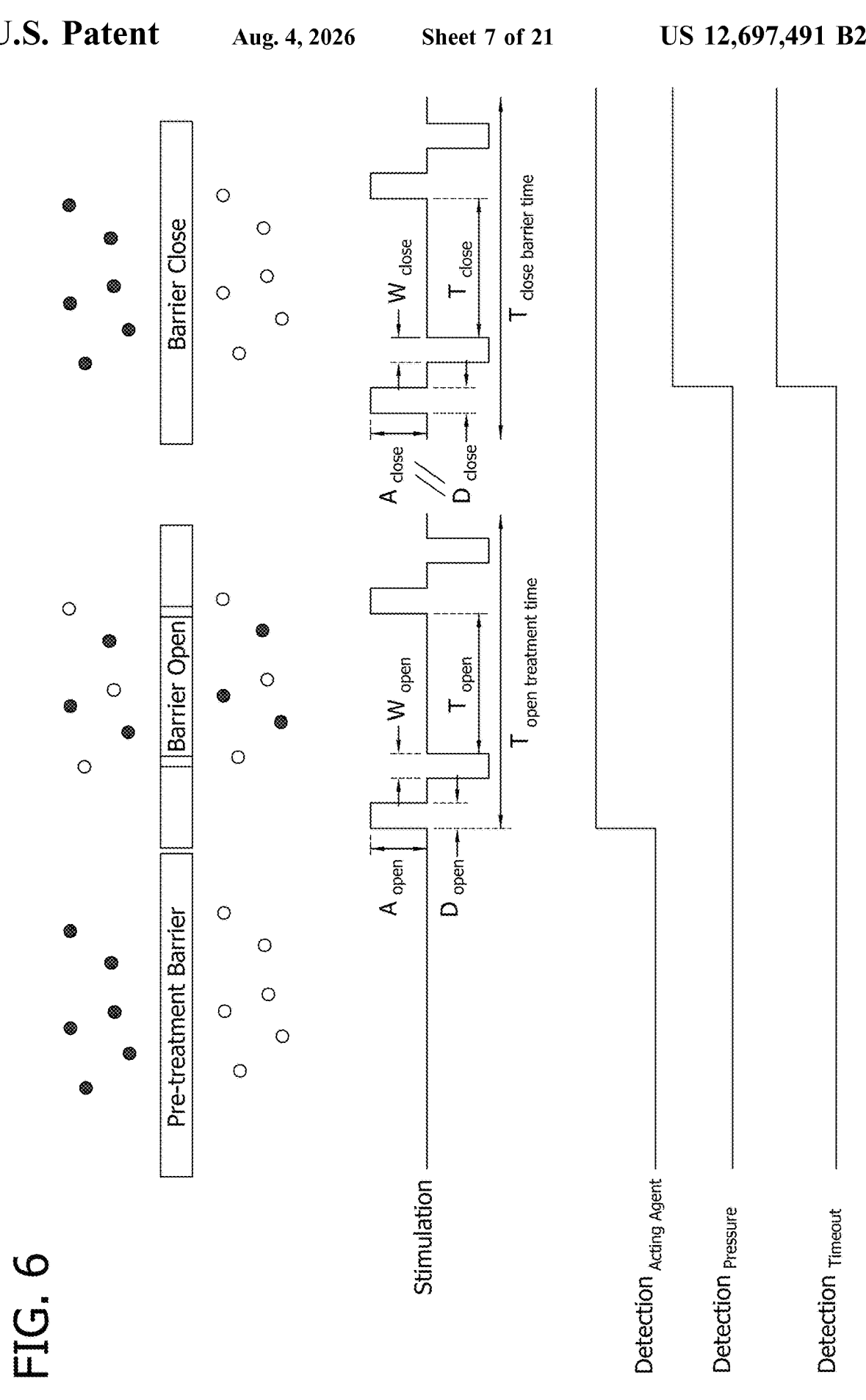
FIG. 6 is a schematic timeline of the method of treating tissue by opening and closing a tissue barrier.

Referring to FIG. 4, upon determining the detected parameter indicates the active agent is available for passing through the barrier (e.g., meets the predetermined parameter threshold), the system is operated to selectively open the barrier. The system may automatically initiate the stimulation or may indicate to the user that stimulation can begin and the user manually initiates the stimulation. The system may include any of the stimulators set forth above, including implanted electrode for stimulating ganglia (e.g., SPG). In one particular example shown in FIGS. 1 and 5, an electrode may be implanted in the subject and powered by an external power unit. As a non-limiting example, electrical stimulation applied to the SPG to open the BBB may have a frequency of 10-60 Hz (e.g., 10-40 Hz or about 10-30 Hz), current of 0.1 to 3 mA, and a bi-phasic waveform. (Further discussion of examples of the applied stimulation is described below.) The stimulation continues until a predetermined parameter is reached indicating that a suitable amount of active agent has passed through the barrier. This parameter may be, for example, elapsed time, active agent concentration in tissue or space interior of barrier, or other parameters. If the continued stimulation is interrupted (e.g., connection between a hand-held device at the stimulator is lost), the system may be programmed to initiate an alarm (e.g., auditory, visual, tactile alarm), which indicates to the user that stimulation was not completed. The user may then reinitiate stimulation to continue treatment.

Referring still to FIG. 4, upon determining suitable delivery of the active agent through the barrier has occurred based on the measured parameter, the system is operated to stimulate the barrier to selectively close the barrier. The system may automatically initiate the stimulation or may indicated to the user that stimulation can begin and the user manually initiates the stimulation. The same device may be used to apply stimulation for closing the barrier, whereby the signal (e.g., electrical signal) is adjusted to a closing signal. As a non-limiting example, electrical stimulation applied to the SPG to close the BBB may have a frequency of 60-200 Hz (e.g., about 100 Hz), current of 0.1 to 3 mA, and a bi-phasic waveform. Further discussion of examples of the applied stimulation is described below. In another embodiment, the stimulation for closing the barrier may be a different type of stimulation as compared to the stimulation for opening the barrier. The stimulation continues until a predetermined parameter is reached indicating the barrier is suitably closed. This parameter may be, for example, elapsed time, change in active agent concentration in tissue or space interior of barrier, or other parameters. If the continued stimulation is interrupted, the system may be programmed to initiate an alarm (e.g., auditory, visual, tactile alarm), which indicates to the user that stimulation was not completed. The user may then reinitiate stimulation to continue treatment.

Upon determining the barrier is suitably closed, the treatment is complete and the stimulation is ceased. One, more, or all of the steps performed by the system may be initiated and performed using a processor and computer-executed instructions saved in memory, each of which is part of the system. In this way, the treatment may be performed autonomously with no or minimal user input.

As set forth above, this exemplary method may be used to treat and deliver active agents to the brain (i.e., affect porosity of the BBB), joints (i.e., affect porosity of synovial membrane), bursa sacs (i.e., affect porosity of bursae wall). Other treatments involving other types of barriers are contemplated.

Figure 14:
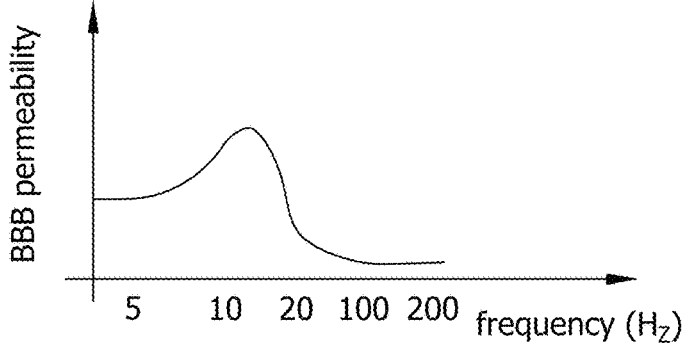
FIG. 14 is an illustrative graph showing BBB permeability as a function of frequency of the electrical stimulation.
Figure 19:
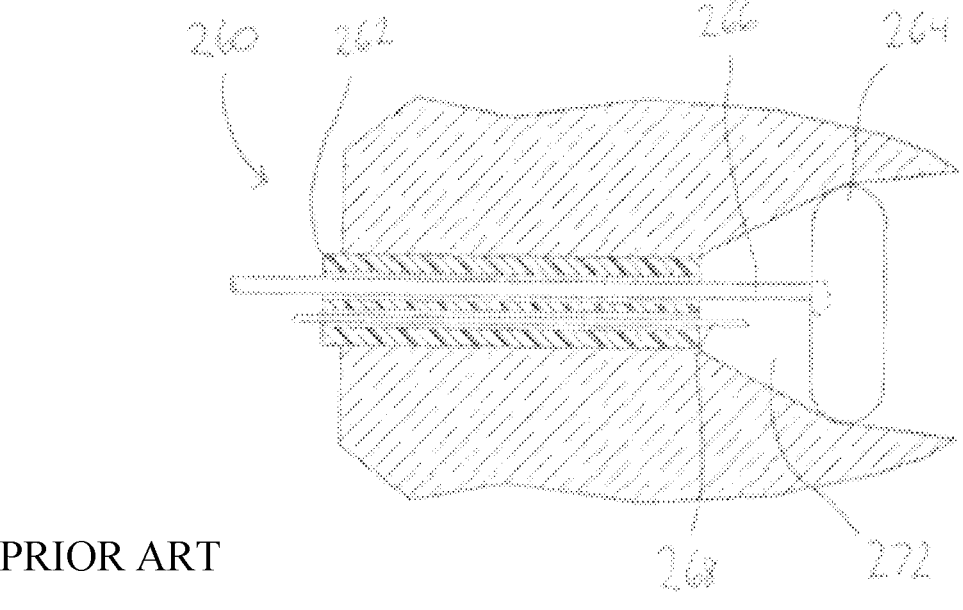
FIG. 19 is a cross-sectional view of a distraction drug delivery system reproduced from U.S. Ser. No. 17/170,710.
Figure 20:
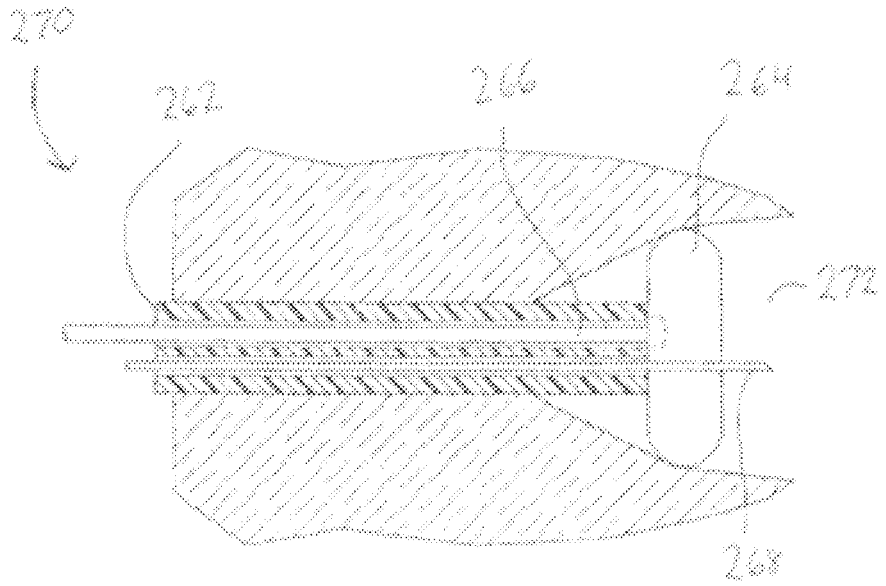
FIG. 20 is a cross-sectional view of another distracting drug delivery system reproduced from the '710 application.

Referring to FIG. 14, the permeability of the BBB modulated by SPG electrical stimulation is frequency dependent. As shown generally in FIG. 14, when the frequency is low (e.g., approximately 5 Hz), the BBB permeability is similar to no SPG stimulation (baseline permeability). When the frequency is increased to about 10 Hz, the permeability of the BBB is greater than baseline permeability. When the frequency is increased to about 100 Hz or greater, the permeability of the BBB decreases and is less than baseline permeability.

It has been found, in certain embodiments, that SPG stimulation using a frequency of from about 10 Hz to about 40 Hz effectively opens the BBB creating mechanical dilation and increasing intracranial blood flow by 40%. This may further cause nitric oxide mediators to release, causing tight junction proteins to coil and relax. Decreasing Transendothelial Electrical Resistance (TEER) may be used to measure the integrity of the tight junction dynamics. In contrast, a frequency of about 100 Hz may act to close the BBB and a frequency of from about 120 Hz to about 150 Hz may be useful in controlling cluster headaches. In either of these high frequency embodiments (e.g., 100 Hz or 120-150 Hz), there is a reduction in intracranial blood flow, reduction in nitric oxide mediator release, and increase in TEER.

In one example, the electrical waveform stimulation to the SPG is a biphasic, charge-balanced waveform where the pulse width is matched to maintain a charge-balanced system. A suitable waveform is shown in FIG. 10. Other suitable waveforms may be used.

Figure 11:
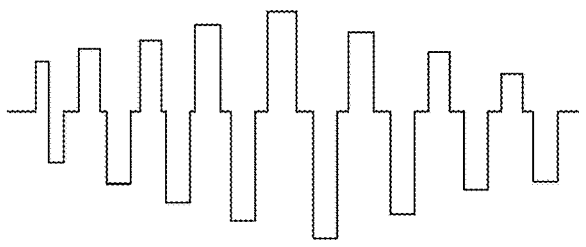
FIG. 11 is an amplitude bi-phasic waveform amplitude modulated with a sinusoidal frequency.
Figure 12:
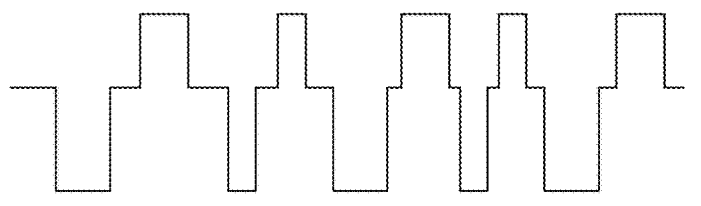
FIG. 12 is a frequency modulation waveform created by modulating the pulse width.
Figure 13:
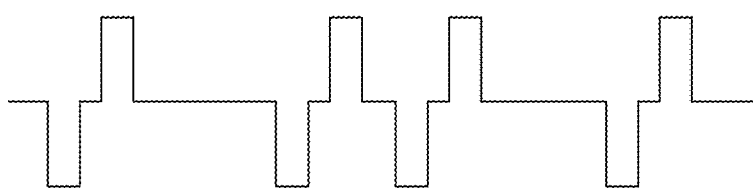
FIG. 13 is a frequency modulation waveform created by modulating the inter pulse frequency.

The waveform can be amplitude or frequency modulated. In one example, the amplitude bi-phasic waveform is amplitude modulated with a sinusoidal frequency, such as shown in FIG. 11. In other examples, amplitude modulated with charge-balanced biphasic waveform may be ramp, sawtooth, or triangle. As examples, frequency modulation waveforms can be created by either modulating the pulse width, such as shown in FIG. 12, or the inter pulse frequency, such as shown in FIG. 13. In another example, the configuration of the electrodes of the device can be modulated to change the treatment field. In particular, the anode and cathode configuration can be reversed to create changes in the magnetic field. This may be used in combination with amplitude/frequency modulation or independently. Additionally, it is considered that monopolar waveforms which are not charged balanced can be used.

Research has suggested that one mechanism of BBB opening and closing (i.e., increasing and decreasing porosity/permeability) is regulated by nitric oxide and/or other nitrogen-based molecules or compounds. In particular, it is believed that suitable stimulation of the SPG (such as at 10 Hz) releases nitric oxide (NO) from vascular endothelia. Nitric oxide (NO) is a key signaling molecule involved in vasodilation. When released, NO relaxes the smooth muscle cells in the walls of blood vessels, causing them to dilate (such as 40% or more dilated), thereby increasing permeability of BBB. In addition, nitric oxide causes proteins at the BBB to shorten or coil up, leading to increase permeability at the BBB. For example, it is believed that nitric oxide causes tight junction (TJ) proteins (e.g., actin, claudin, occluin) to shorten to increase permeability of the BBB at the TJ proteins. Further, it is believed that stimulation affects the transendothelial electrical resistance contributed by claudin and occluding proteins (e.g., zonula occludens). That is, transendothelial electrical resistance is reduced at lower frequencies, such as 10 Hz. Stimuli at 20 hertz and above (up to 100 hz or greater) cause SPG to mediate reduction in porosity or closing of BBB. This higher frequency (and other waveforms) create nitric oxide mediated response (stops release of nitric oxide) to affect endothelial proteins to uncoil and close BBB and induces vasoconstriction. This coil/uncoil protein response is reversible via electrical stimuli at SPG or other autonomic nerve fibers. At this higher frequency, the transendothelial electrical resistance is also increased.

This response can also occur outside the CNS and affect vasculature and permeability of molecules including antibodies and stem cells to the rest of the human body (including pharmaceuticals and chemotherapy agents, hormones, nutrients) to specific peripheral locations in the body to target specific tissue locations for therapy. Thus, electrical stimulation can be used on other parts of the nervous system at locations other than SPG. Stimulation of autonomic system can control throughout body similar responses-sympathetic nerves can close membranes by contraction of vasculature-parasympathetic cause expansion/dilation of vessels and or opening of vascular membranes-proteins responses similar to above.

In one or more embodiments, stimulation-induced regulation of the BBB, such as described above, may be combined with modification of the active agent to target transporters of the BBB and/or enhance penetration into brain tissue once across the BBB. Transporter proteins are present on the surface of endothelial cells lining the blood vessels in the brain. These transporters play a crucial role in regulating the entry and exit of various substances into and out of the brain through the junction (e.g., tight junctions) of the BBB. Some substances, including essential nutrients, glucose, and certain ions, are transported actively across the BBB by specific transporter proteins. Researchers design drugs or modify existing drugs to interact with these specific transporters. This involves incorporating chemical structures or functional groups that can be recognized by the transporters responsible for shuttling essential substances across the BBB. The goal is to create drug molecules that are carried on these transporters, facilitating their transport across the BBB. These transporters can be exploited for drug delivery by designing drug molecules that mimic the structure of substances that are actively transported into the brain. Amino acid transporters are another target. Certain drugs can be designed to resemble amino acids, taking advantage of the transport systems that actively move amino acids across the BBB. Some drugs can be designed to bind to specific receptors on the surface of BBB endothelial cells. This binding can trigger receptor-mediated endocytosis, allowing the drug to be transported into the brain. Nanoparticles and carrier systems can be engineered to encapsulate drugs and exploit specific transporters for BBB penetration. These carriers may include liposomes, micelles, or other nanoscale delivery vehicles. Examples of carriers are lipids (lipophylicity), transferrin receptor/ligands, hyaluronic acid, insulin receptors, lipoproteins, membrane coatings, liposomes, polymers (e.g., PGA, PLA), nanogels, gold, iron, or graphene. The attachment of a carrier to the active agent may facilitate receptor mediated transcytosis, carrier mediated transport, or transporter mediated nanocarrier.

Figure 7:
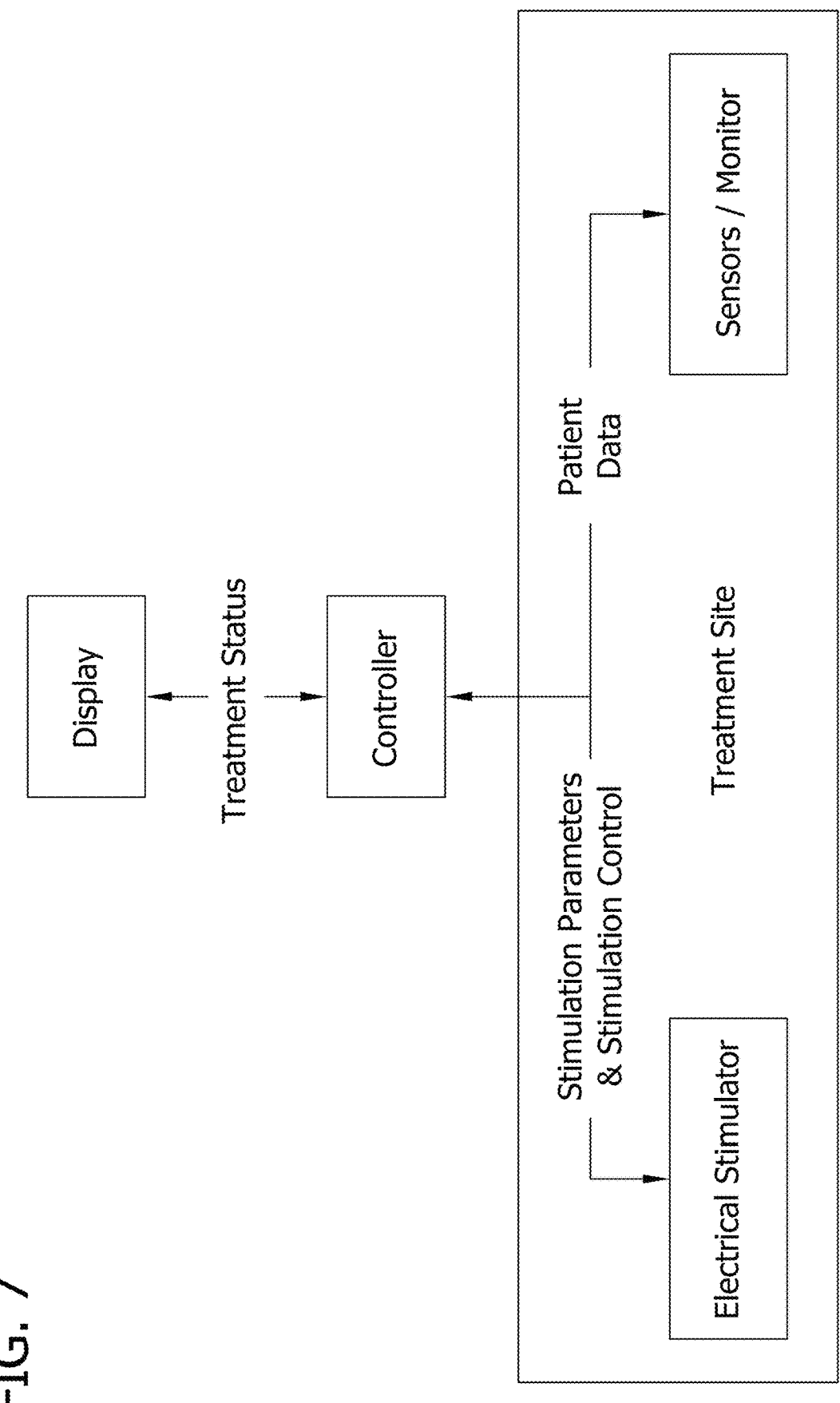
FIG. 7 is a schematic representation of one embodiment of the system for treating tissue by opening and closing a tissue barrier.
Figure 8:
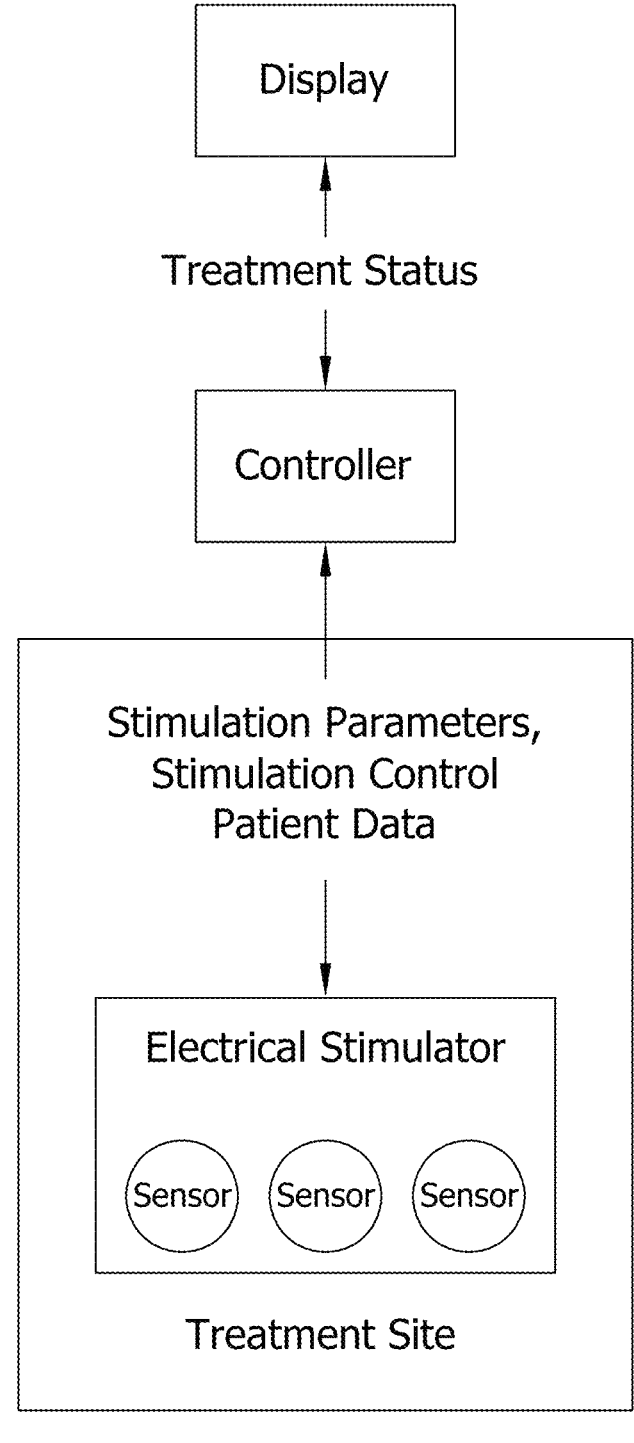
FIG. 8 is a schematic representation of another embodiment of the system.

Referring to FIG. 7, a schematic of a suitable system for performing the described method is shown. In this embodiment, the system includes a display, a controller having a processor and memory with computer-readable instructions, an electrode assembly or stimulator (e.g., an electrical stimulator) 200, 300, and sensor(s) for monitoring parameters of the patient to determine when stimuli from the stimulator 200, 300 should be operated. In this embodiment, the sensor(s) are separate from the electrical stimulator. In this embodiment, each of the stimulator and sensor(s) are implantable or deliverable to or adjacent the barrier. Referring to FIG. 8, a schematic of a similar system is shown. The difference being the sensor(s) are incorporated with the stimulator 200, 300.

In one or more embodiments, a system and method described herein is used as treatment when the BBB has been disrupted due to ischemic or hemorrhagic strokes, or other conditions. In such a method, the disrupted BBB is brought back to normal function by controlling the opening and closing of the BBB, depending on how the function of the BBB was affected by the stroke. Proper diagnosis of the irregular function of the BBB will determine the treatment using the system and method of the present disclosure.

It is believed that one potential adverse effect of opening the BBB is edema in or around the brain. This can result from oncotic forces generated by influx of fluids and particles into the brain. In one embodiment, the intracranial pressure and brain edema of the patient could be monitored while the BBB is disrupted. This could be done by with MRI, a pressure sensor, transcranial ultrasound with Doppler, blood pressure, or any combination of these methods. Other methods known in the art can be used as a stand monitor or combined. In one example, correlation between intracranial pressure and blood pressure (absolute or relative) may be used to determine intracranial pressure. Whenever the brain edema is detected, and alert could be shown to the operator, who can adjust the treatment protocol. In another embodiment, the monitoring could be integrated into the device or two-way communication could be established between the stimulator and the monitoring equipment.

Thus, these sensors can be integrated into the device similar to the integration of the active agent sensors shown in FIG. 8. When any swelling of the brain is detected, the system can adjust the stimulation produced by the stimulator (i.e., automatically change from an open signal to a closed signal) to close the BBB. By using artificial intelligence or machine learning, a predictive algorithm could be developed that would recognize the potential for swelling prior to the event and the signal could be adjusted. The biological response time to the changing signals could be calculated to optimize the opening and closing of the BBB. Additionally, it is considered that external inputs could be used to power machine learning methods such a convolutional neural network including but not limited to MRI, EEG, MEG. Additionally, drug uptake could be monitored, nitric oxide levels, or the transepithelial/endothelial electrical resistance (TEER) could be used.

It is also believed that using frequency that is optimal for opening the BBB may increase potential for edema or the size of particle targeted for delivery across the BBB. To optimize the therapy and maintain patient safety, a lower frequency such as 5 Hz could be selected to partially open the BBB. In another example, modulation techniques are used to create a signal for creating variable permeability of the BBB. In one embodiment the neuromodulation signal applied to the SPG could frequency shift between the "open" and "close" signals. It is also considered that pulse width modulation, frequency modulation, amplitude modulation, or other known techniques could be used to optimize the signal for the desired porosity while minimizing adverse effects. In selecting the opening and closing signals, it is important to consider that lymphatic and venous drainage may require different frequency, waveform, or time. For example, 1 to 20 hz to drain and higher than 20 hz (e.g., 150 hz) to quickly close the BBB.

Rather than stimulating neuron cells (e.g., SPG) to affect porosity of barrier (e.g., BBB), the system may locally stimulate the barrier (e.g., BBB, or other blood vessels at or near the brain) to open and close the barrier. Moreover, arteries may be stimulated to affect inflow or veins/lymphatics may be stimulated to affect outflow.

In some embodiments, devices are used to control venous/lymphatic permeability. These devices may be selected from the group consisting of microfluidic devices, electroporation devices, drug delivery systems, or combinations thereof.

Microfluidic devices are known to, among other things, effect various substances on endothelial cell permeability in vitro.

Electroporation devices are known to, among other things, temporarily the permeability of cell membranes which may useful in drug delivery.

Drug delivery systems, for example implantable devices, are known to, among other things, release substances that modulate vascular permeability for therapeutic purposes.

In some embodiments, systems may be put in place to measure permeability which may be selected from the group consisting of transwell system, Optical Coherence Tomography (OCT), or combinations thereof.

Transwell system are known to, among other things, measure the permeability of endothelial cell layers with the administration of different treatments.

OCT is an imaging technique known to, among other things, be useful in assessing changes in vascular permeability in real-time.

In certain embodiments, bioreactors are known to be, among other things, useful in understanding the effects of drugs or other factors on vascular permeability by mimicking physiological conditions.

In one example, a catheter is delivered or "floated" to specific location in the brain to stimulate local blood vessel/autonomic system to open or close electrically. This could be controlled to time opening or dilation with delivery of a medication, therapy, or cellular treatment by longing drug release to opening then closing to limit risk of intracranial swelling or complications due to pressure or osmotic differentials. This is considered local and direct stimulation of the barrier (e.g., SPG) rather than stimulating neurons (e.g., ganglia) to affect the barrier. Frequency and/or amplitude of the electrical signal may be adjustable to adjust porosity of the blood vessel and/or dilation of the blood vessel. Stimulation may also be imparted on a cellular basis to enhance medication or therapeutic treatment across a cell membrane or a micro level.

In one or more embodiments, described in more detail below, a coating of the implantable electrode assembly 200 could be partially biodegradable to act as an insulator then when it degrades, even partially, electrode(s) 201 or electronic device loses functional ability.

Non-electrical stimulation could be used as well, which could include direct manipulation of the SPG, or external stimulation with transcranial magnet stimulation, high intensity focused ultrasound (HiFu), or low intensity pulsed ultrasound (LIPUS).

When opening the BBB via SPG stimulation, LIPUS, HiFu or other methods it will be critical to protect the CNS from unintended exposure to medicines that might already be in the patients' bloodstream during therapy. In one embodiment of this invention, this can be done through software by creating a database of all prescription and over the counter medicines and supplements that a patient is currently taking and the dosing schedule. By using the known absorption rates of these drugs, half-life, and size of the drug molecule a treatment schedule can be created for each patient, which could show the optimal time to perform a therapy to relax the BBB. It is also considered that this therapy schedule could be block therapy from being delivered to a patient during times that levels of pharmaceutical are present that could be dangerous to the CNS.

The system can also be configured to integrate into a hospital network to pull the patient information and medication lists through defined protocols such as Health Level 7 (HL7). Information could also be imported from cell phone applications. This software can also be used to calculate the optimal time to deliver a drug to a patient intended to cross the BBB, as well as the optimal time to perform therapy.

In one or more embodiments, a medical device, such as the neurostimulator or other medical device used by a patient, has capability for billing by use of the device. To allow for billing the therapy, multiple hardware and software solution can be implemented depending on design constraints. In FIG. 15 a stand along configuration is shown. This configuration is the simplest and does not require an internet connection to the handheld or programming tablet. If this configuration, a total amount of uses, a valid date range, or a combination of the two could be loaded on the device. When the user has excited the amount of total uses, or the valid usage dates have expired, the user could be required to bring the device back to the healthcare professionals office where additional time can be added and required maintenance performed (if required) on the handheld.

Alternatively, it is considered that the handheld device can be connected to the internet via a tethered connection (FIG. 16). This could be a smart phone, a dedicated device, a laptop, tablet or personal computer. An application running on the tethered device would communicate with remote servers, which could update the total number of uses and upload usage information for review by the company or healthcare professionals. In FIG. 17, a configuration is shown which the cable tether between the phone, tablet, or computer could be removed by using a known wireless protocol such as BlueTooth or WiFi.

Alternatively, a system could be made there the remote connected directly to the internet. This could be done via WiFi, cellular connection, or other known connection methods. In this configuration, the handheld device would communicate directly with the company servers. Allowing the ability for real time usage, billing, and usage information to be reported to the company.

In one or more embodiments, parameters of stimulation may be varied to control autonomic nervous system. For example, time, frequency, power and/or location may be varied to control autonomic nervous system. More than one autonomic system location may be stimulated simultaneously or one after another. For example, one or more of the following may be stimulated: vagus nerve, SPG, sympathetic chain at spine, specific autonomic fibers, stellate ganglion, petrosal nerve, or a specific fiber off of these ganglia, or even stimulation at a cellular level.

In further embodiments, configuration of the implanted device and/or handheld device may be conducted as shown in FIGS. 15-17 by a physician. The physician may be able to adjust the parameters of the stimulation, including frequency, intensity, session duration, etc.

The ease of the device use by the patient also provides a number of benefits. As illustrate in FIG. 5, the patient (or physician) selects the desired stimulation program and holds the device against the check for convenient pain relief. This allows, for example, for rapid pain reduction in as little as 50 minutes for a majority of patients (e.g., 67% or more).

Other treatments for modulation may be used, including cryotherapy, RAF therapy to prolong the stimulation or override or sympathetic over parasympathetic tone to control many disease or behavioral disorders, such as stress, dental or mouth disorders like TMJ or oral swelling pain, hypertension, anxiety, schizophrenia, anger disorders, mood disorders, sweating, swelling, chronic pain, GI disorders, memory loss and dementia. Many disorders are mediated by the autonomic nervous system and stress hormones like glucocorticoids, epinephrine, argentine, vasopressin, and other "stressor" molecules in brain, spinal cord and peripheral nervous system.

In one example, SPG can be stimulated, then another location, such as vagus nerve or other stumping, can be stimulated or overrode to get response to treat more complex disorders, such as adrenal gland overstimulation of endorphins or stressor molecules, hormones that increase or decrease stress systemically or to a specific location like cerebral hemisphere (SPG) or asrenal gland or vagus nerve to heart, lungs, GI system, pancreas liver, intestines, etc.

Part or all of stimulation system and electronics may be biodegradable. Parts may be bond or join in manufacturing even while implanted in the body or elsewhere to reimplant battery or electrical components then reseal welding with biogegradeable or non-biodegradable components so do not have to remove device to change battery or electrode or any component and repair "in situ" like a pacemaker or an active implant. The stimulation device may be internally powered by energy coming from heat, motion, fluid movement, magnets, blood, fluid pressure, or energy storage internal like a battery or capacitor in a completely coated housing.

Benefits of the described stimulation system and electronics include convenient patient control, minimal maintenance/upkeep, and a long device life. The device may be rechargeable via standard connection port (e.g., USB plug) and provide up to 18 months of continuous use. The system may be designed to require minimal maintenance and have a device life of up to about 5 years or more to enable long-term device use.

Although discussion herein may be directed to BBB stimulation, it will be understood that other methods and systems may be employed. For example, four of the twelve cranial nerves are known to have autonomic fibers-optic, hypoglossal, glosdopharyngeal, and vagus. It may be possible to stimulate these nerves transcutaneously (e.g., electrically or using edible stimuli) to activate or initiate a desired autonomic response. This stimulation may be combined with one or more of the previously discussed methods or systems.

In one embodiment, optical stimulation and SPG stimulation can be used in combination. For example, optical stimulation, delivery of an active agent (e.g., noradrenaline), SPG stimulation, and further delivery of an active agent across the now open BBB.

In another embodiment, edible stimulation, nerve stimulation, and SPG stimulation may be used in combination to close the BBB. For example, providing a bitter tasting component, stimulating the parasympathetic nervous system at the glossopharyngeal nerve, release of an active agent (e.g., acetylcholine), and altering the SPG stimulation frequency to close the BBB.

Still further, any of the above methods or systems may be employed in combination with specific infusions (arterial, venous, oral, etc.).

In certain embodiments, any of the above methods or systems may further comprise artificial intelligence (AI) in the optimization of delivery of the active ingredient. For example, by controlling the device (e.g., stimulation device and resulting power, application time, location, etc.) and the concentration of the active ingredient in order to optimize delivery across the BBB.

As described above, in one or more examples the stimulation system is configured to vary parameters to control various autonomic or neural disorders, or adjust to person, drug or disease with the multiple variables and learning algorithms to optimize individual therapy with time frequency power drug location(s). These parameters are adjusted to optimize for each use or to constantly improve, such as by using AI software. Parameters may also vary based on time of day, nutrition, sleep or activity and intensity, heart rate, blood pressure, diurnal cycle, or sugar or other chemical level, which may be sensed by mobile devices or sensors (e.g. wearable sensors or implantable sensors). This data for adjusting stimulation parameters may be analyzed via cloud or a local processing device in communication with the stimulation system.

Figure 23:
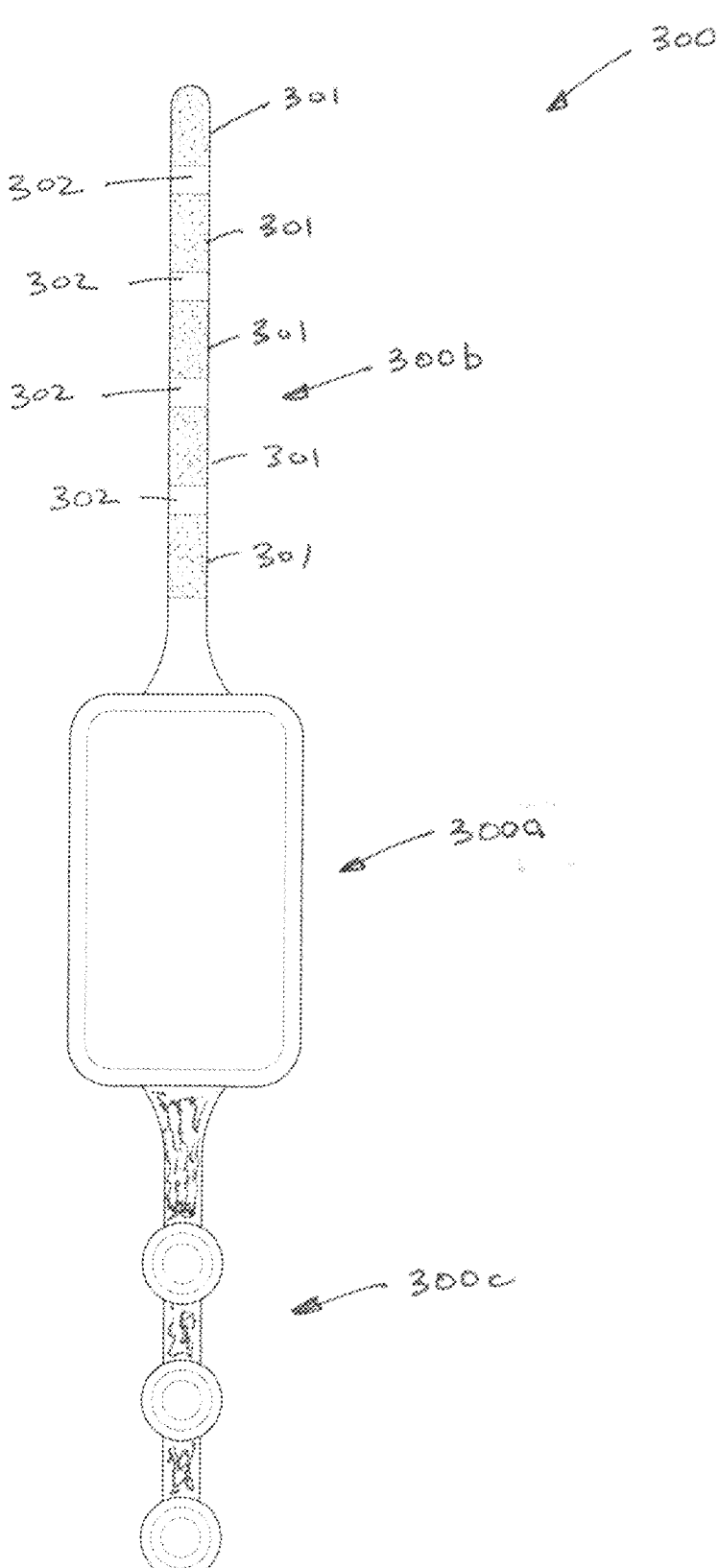
FIG. 23 is a plan view of another embodiment of an electrode assembly.
Figure 24:
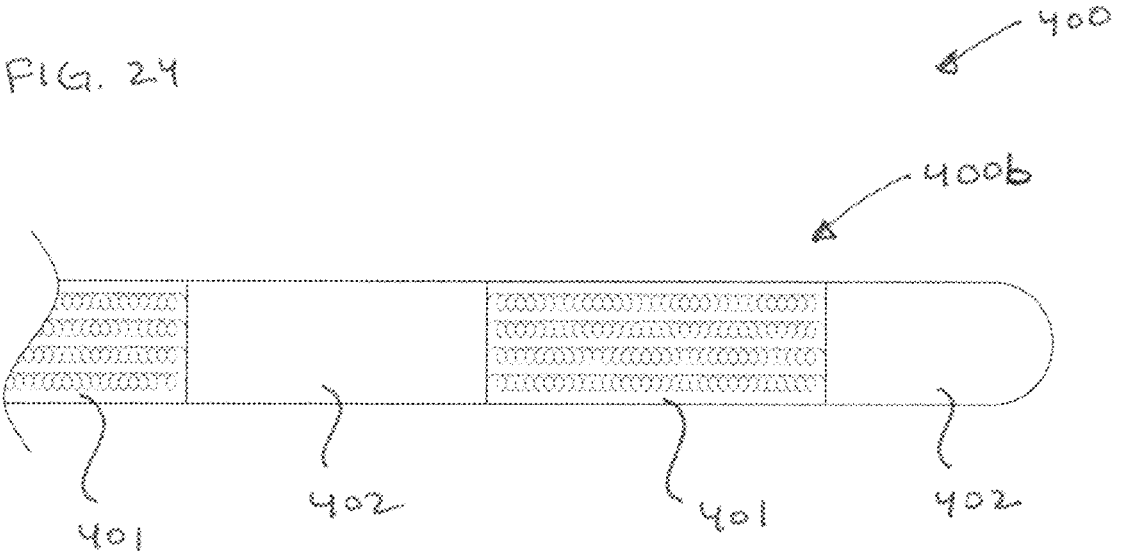

Referring to FIGS. 23, an electrode assembly, generally indicated at 300, is similar to the electrode assembly 200, and therefore, the same named features will be indicated by corresponding reference numerals plus 100. The electrode assembly 300 may incorporate structural characteristics designed to enhance electrochemical performance and optimize charge transfer characteristics for sphenopalatine ganglion (SPG) stimulation or other neurostimulation. The electrodes 301 on the electrode lead 300b may be fabricated from biocompatible conductive materials selected for their superior charge-injection capacity and long-term stability in neural environments. Platinum as an electrode material has excellent biocompatibility, corrosion resistance, and established performance in neural stimulation applications. Titanium nitride may also be employed as an electrode material, offering favorable electrochemical properties and biocompatibility while providing cost advantages over precious metal alternatives.

The surfaces of the electrodes 301 may be modified to create roughened topographies that substantially increase the effective electrochemical surface area available for charge injection. In particular, roughened surfaces of the electrodes 301 facilitate improved ionic conduction and energy coupling, improving stimulation efficacy and reducing tissue heating and undesired electrochemical reaction. Microfabrication techniques may be employed to create controlled surface features with dimensions ranging from nanometer to micrometer scales. These microfabrication processes may include photolithography, electron beam lithography, or focused ion beam milling to create the roughened surface. Plasma etching may be utilized to create the roughened surface through controlled removal of electrode material using reactive ion etching or other plasma-based processes. Electrochemical deposition techniques may be used to modify surfaces of the electrodes 301 through the controlled deposition of conductive materials or coatings. These electrochemical processes may include electroplating, electroless plating, or anodization procedures that create porous or textured surface layers. Abrasive treatments may also be employed to create roughened electrode surfaces through mechanical modification processes such as sandblasting, grinding, or chemical etching with acids or other reactive solutions.

The electrode (and electrode lead) geometry may be configured in various shapes to accommodate anatomical variations and optimize positioning relative to the sphenopalatine ganglion. Cylindrical electrodes 301 may provide uniform current distribution around the electrode circumference, allowing for omnidirectional stimulation patterns that may be beneficial when precise electrode orientation cannot be controlled during implantation. The cylindrical geometry may feature various diameter and length dimensions to match the anatomical constraints of the implantation site while providing adequate surface area for charge injection. Oval electrodes 301 may offer advantages in certain anatomical orientations, providing an elongated contact surface that may better conform to nerve bundle geometries or tissue interfaces. The oval cross-section may be oriented to maximize contact area with target neural structures while minimizing contact with surrounding tissues that should not be stimulated.

Single-sided electrodes 301 may be employed when directional stimulation is desired or when anatomical constraints limit the available space for electrode placement. These single-sided electrodes may feature active stimulation surfaces on one side while incorporating insulating materials on the opposite side to prevent unwanted current flow. The single-sided design may allow for more precise targeting of neural structures and may reduce the overall electrode volume compared to circumferential designs.

Manufacturing of the electrode lead 300b may utilize various molding techniques to integrate the electrodes 301 with polymer insulation 306, which are positioned between adjacent electrodes. Injection molding processes may be employed to create the electrode lead 300b by positioning pre-fabricated electrodes 301 within molds and injecting molten polymer materials around the electrodes to form the lead.

Liquid injection molding techniques may be applied when working with low-viscosity polymer systems or when precise control over material flow and curing is required. These liquid injection processes may enable the creation of complex electrode lead geometries with embedded conductor wires and multiple electrode contacts positioned at specific locations along the lead length. The molding processes may incorporate techniques for maintaining electrical continuity between internal conductor wires and external electrode contacts while ensuring complete encapsulation of all conductive elements except for the intended stimulation surfaces. Post-molding operations may include surface treatments, sterilization procedures, and quality control testing to verify electrical performance and mechanical integrity of the completed electrode leads.

The electrode body 300a may provide hermetic encapsulation of internal electronic components while maintaining biocompatibility and enabling wireless communication capabilities through radio-frequency transparent materials. The electrode body 300a may be constructed using ceramic materials selected for their combination of biocompatibility, electrical insulation properties, and electromagnetic transparency characteristics that allow efficient transmission of inductive power and radio frequency signals between external controllers (e.g., the hand-held controller) and implanted electronics. Suitable materials may include alumina ceramic, sapphire (e.g., sapphire comprising single-crystal alumina structures), yttria-stabilized zirconia ceramic, silicon nitride ceramic, glass-ceramic, aluminum nitride, barium titanate, fused silica, hydroxyapatite, or combinations thereof.

Feedthrough pin assemblies (not shown) may provide electrical connections between internal electronic circuits and external electrodes 301 while maintaining hermetic scaling of the interior of the body 300a. The feedthrough pins may comprise biocompatible conductive materials such as platinum, gold, or titanium alloys that resist corrosion in physiological environments and provide reliable electrical conductivity over extended implantation periods.

Brazing processes may be employed to create hermetic seals between feedthrough pins and ceramic body materials through the application of high-temperature brazing alloys that form metallurgical bonds with both pin and housing materials. In another embodiment, in-place formation techniques may create feedthrough connections during ceramic body fabrication processes rather than through subsequent brazing operations. These in-place formation methods may involve positioning conductive pins within ceramic powder compacts prior to sintering operations that consolidate the ceramic structure around the embedded conductors.

Overmold encapsulation may provide additional protection and biocompatibility enhancement through the application of polymer coatings over the ceramic body 300a. The overmold material may serve as a compliant interface between the rigid ceramic body 300a and surrounding biological tissues, reducing mechanical stress concentrations and improving tissue compatibility. Suitable materials include, but are not limited to silicone polymer materials, polyether block amide (PEBA) materials, thermoplastic polyurethane materials, polyether urethane materials, silicone-polyurethane copolymer materials, or combinations thereof.

Various fixation methods may be employed to secure the electrode assembly 300, or other electrode assemblies or implants, at the target anatomical location while accommodating different surgical approaches and patient-specific anatomical considerations. Traditional fixation approaches may utilize the rigid bone plates, such as fixation apparatus 200c, that provide mechanical attachment to surrounding bone structures through threaded fasteners such as screws or pins.

Alternative fixation methodologies may employ suture anchors (not shown) that enable flexible attachment of the electrode assembly to soft tissue structures including fascia, muscle tissue, or periosteal layers. Suture anchor systems may utilize knotless designs that facilitate minimally invasive implantation procedures while providing secure fixation through mechanical expansion or barbed configurations that resist pullout forces. Suture materials may comprise nonabsorbable polymers or biocompatible fibers that maintain tensile strength over extended periods while accommodating tissue movement and physiological loading conditions.

Figure 24:
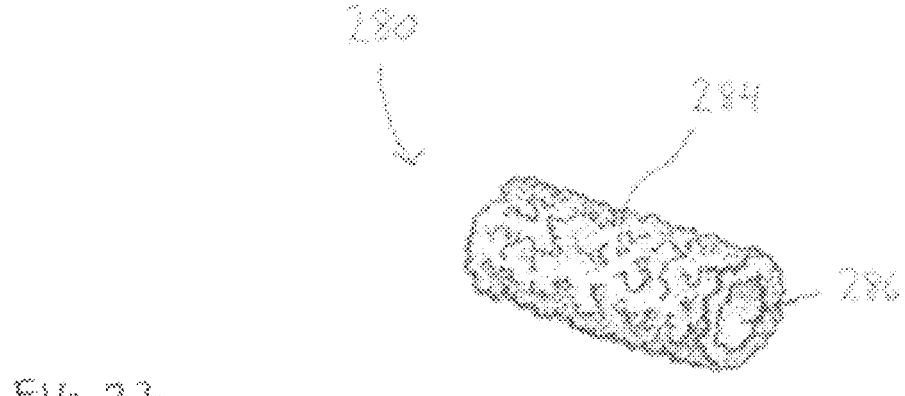
FIG. 24 is an enlarged, partial plan view of an electrode lead.
Figure 22:
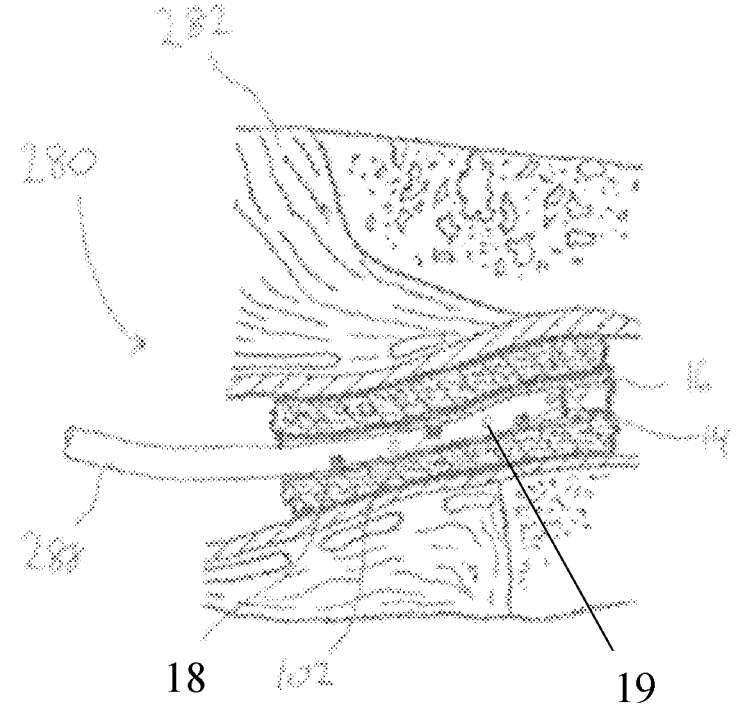
FIG. 22 is a cross-sectional view of the drug dispersion member disposed on a drug delivery tube of an omnidirectional drug dispersal system.
Figure 25:
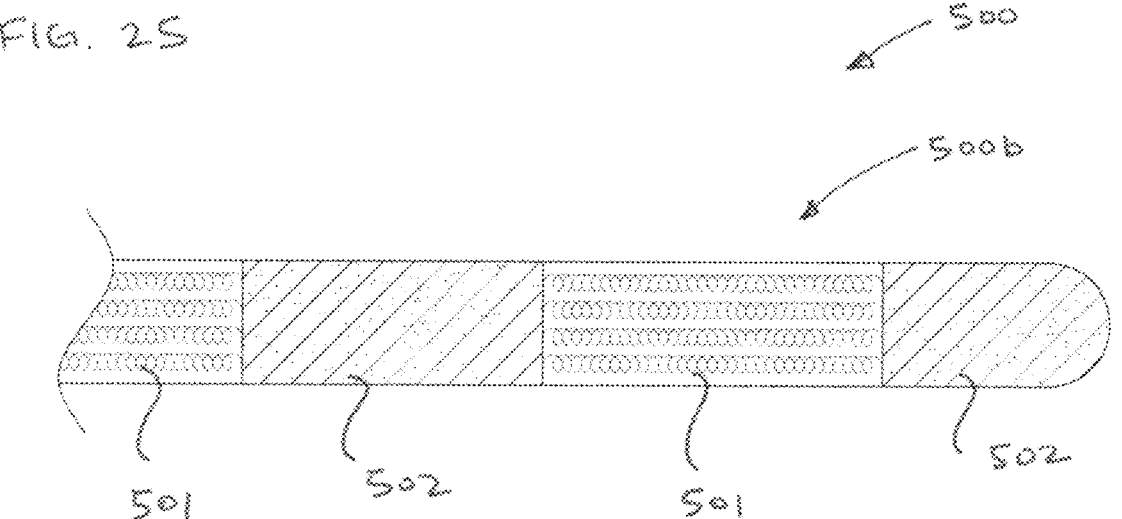
FIG. 25 is an enlarged, partial plan view of another electrode lead.

Referring to FIGS. 23-25, in one or more embodiments, the electrode assembly could be partially ingrowth capable so a cuff or section with tissue ingrowth capability which stabilizes the electrode through motion or activity. The porosity of ingrowth would optimally be less than 400 microns and could be temporary stabilized by suture anchors, e.g., knotless anchors for MIS applications to stabilize to fascia or tissue or bone. In FIG. 23, tissue (e.g., bone) ingrowth surface is on the integral fixation apparatus 300c (e.g., flexible or rigid bone plate with openings for fasteners). In FIG. 24, the ingrowth surface is on one or more of the electrodes 401 of the electrode lead 400c of the electrode assembly 400. In this illustrated example, the insulation sections (e.g., polymer sections) This electrode surface may be configured for both ingrowth of tissue (e.g., bone) and enhanced topography to increase the effective electrochemical surface area available for charge injection compared to smooth electrode surface. Alternatively, the surface of the electrode(s) may be configured for only one of an increased effective electrochemical surface area available for charge injection via a roughened surface or tissue ingrowth. In FIG. 25, the tissue ingrowth surface is on the insulation segments 502, disposed between the electrodes 502 on the electrode lead 500b of the electrode assembly 500. In this embodiment, the ingrowth surface is also on the electrodes 502, although in other embodiments, the ingrowth surface may only be on the insulation segments 502.

Ingrowth surface modifications may promote direct tissue adhesion and biological fixation of the electrode assembly or stimulator through controlled surface texturing or coating applications that encourage cellular attachment and tissue integration. The ingrowth surfaces may feature porous structures, roughened topographies, or bioactive coatings that facilitate bone or soft tissue ingrowth around portions of the electrode assembly. As discussed above, ingrowth surfaces may be strategically positioned on specific regions of the electrode assembly to provide biological fixation while maintaining smooth surfaces in areas where tissue ingrowth could interfere with electrode function or future device removal procedures. The ingrowth process may develop over weeks to months following implantation, gradually providing increased fixation strength as tissue integration progresses.

In one or more embodiments, biodegradable fixation components may be used to temporary anchoring solutions that provide immediate mechanical stability during initial healing phases while gradually transferring load-bearing responsibilities to surrounding tissues as the fixation elements undergo controlled degradation. Biodegradable anchor materials may comprise resorbable polymers such as polylactic acid, polyglycolic acid, or copolymer compositions that degrade through hydrolytic processes over predetermined time periods ranging from weeks to months. As biodegradable components undergo resorption, the electrode assembly may become increasingly reliant on tissue ingrowth and biological fixation mechanisms for long-term stability. As an example, in FIG. 23 where the bone plate 300c includes the tissue ingrowth surface, biodegradable anchors may be inserted through the openings to secure the bone plate to tissue (e.g., bone). The anchors gradually degrade as the tissue grows into the bone plate 300c.

The biodegradable fixation approach may provide advantages for device removal procedures by reducing the mechanical attachment strength over time and minimizing the tissue disruption associated with removing the electrode assembly. Biodegradable fixation systems may also accommodate infection scenarios where accelerated degradation may occur, potentially facilitating natural clearance of fixation materials and reducing the extent of surgical intervention required for device removal. The combination of biodegradable fixation components with ingrowth surfaces may create hybrid fixation systems that transition from mechanical anchoring to biological integration over the course of the healing and tissue remodeling process.

It is also contemplated that the electrode assembly may be temporary implanted in a similar method to an SPG block, although other methods could be used.

The electrode lead of any of the embodiments of the electrode assembly or stimulator may incorporate steering mechanisms that enable positioning during implantation and post-implantation repositioning of the electrodes on the electrode lead to optimize therapeutic positioning relative to the SPG, for example. The following description may be incorporated in other types of implantable stimulators that include electrode leads. The steerable electrode lead may provide clinicians with the ability to fine-tune electrode placement after initial surgical implantation, potentially reducing the need for revision surgeries and improving therapeutic outcomes through enhanced proximity to target neural structures. The steerable functionality may be particularly beneficial in cases where initial electrode positioning does not achieve optimal stimulation parameters or when anatomical variations prevent precise placement during the surgical procedure. Moreover, the steering capabilities may enable the use of less electrodes on the electrode lead because of its ability to be delivered to a more precise location relative to the target (e.g., SPG) location.

Figure 26:
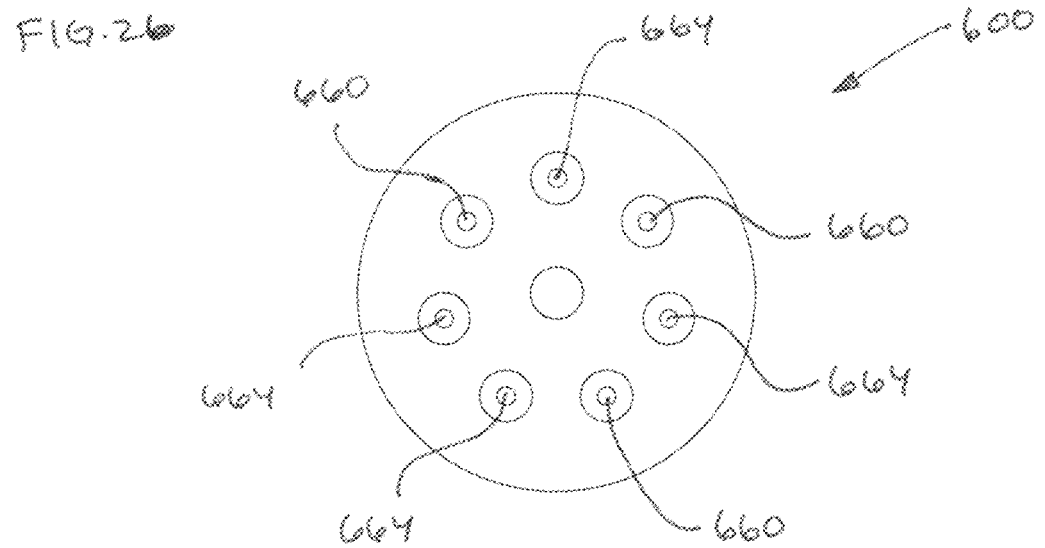
FIG. 26 is a cross section of a steerable electrode lead.

Referring to FIG. 26, in one example, shape memory alloy actuation may provide one approach for creating the steerable electrode lead 600 through the integration of thermally responsive metallic elements 660 within the lead structure. In one example, the elements 660 comprise Nitinol wires or strips embedded along the length of the electrode lead 600, taking advantage of the unique phase transformation properties of this nickel-titanium alloy. The shape memory alloy elements 660 may be pre-programmed during manufacturing to assume specific curved or bent configurations when exposed to predetermined temperature thresholds. In some cases, the shape memory alloy elements 660 may be activated through direct electrical heating, where controlled current application raises the temperature of the elements above their transformation temperature, causing them to contract or change shape according to their programmed memory configuration, thereby bending the distal end of the electrode lead 600, for example. The shape memory alloy actuation system may incorporate multiple nitinol wires 660 positioned at different locations along the electrode lead to enable three-dimensional positioning capabilities. Each nitinol wire 660 may be independently controlled through separate electrical connections, allowing for selective activation of specific lead segments to achieve desired bending patterns. Runing parallel to the shape memory wires 660 are the electrical conductors or wires 664 electrically connected to the electrodes (e.g., electrodes 201) on the electrical lead 600. In this example, there are four wires 664 for four electrodes 201.

Figure 27:
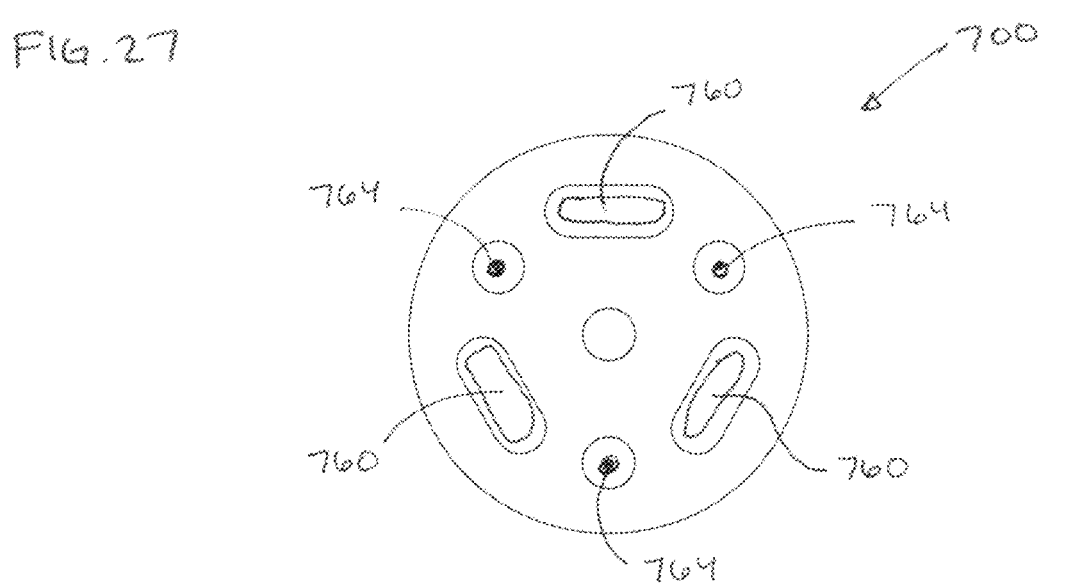
FIG. 27 is a cross section of another steerable electrode lead.

In another example, magnetic steering mechanisms may offer an alternative or additional approach for electrode lead positioning through the integration of magnetic elements within the lead structure and the application of external magnetic fields. Referring to FIG. 27, small permanent magnets or magnetically responsive elements 760 may be embedded within the electrode lead 700 at selected locations, typically near the distal tip where the stimulation electrodes are positioned. External magnetic field generators may be positioned around or at implantation site to create controlled magnetic gradients that exert forces on the embedded magnetic elements 760. The interaction between the external magnetic fields and the embedded magnetic elements 760 may cause the electrode lead to bend or rotate in response to changes in field strength and direction. The magnetic elements 760 may be positioned adjacent to the electrical conductors 764, which are also embedded in the polymeric material of the electrode lead 700, for example. A suitable magnetic system is set forth in U.S. Ser. No. 12/134,083, filed Jun. 5, 2008, the entirety of which is hereby incorporated by reference.

The magnetic steering system may utilize multiple external magnetic field sources positioned at different locations around the implantation site to provide comprehensive directional control over electrode positioning. In some cases, the external magnetic field generators may be integrated into the handheld controller/device 250 that clinicians can position and orient to achieve desired electrode positioning. The magnetic steering approach may allow for real-time adjustment of electrode position during stimulation testing, enabling immediate feedback regarding the effectiveness of different positioning configurations. The embedded magnetic elements may be designed with specific magnetic moment characteristics that provide sufficient responsiveness to external fields while maintaining biocompatibility and long-term stability within the body.

Figure 28:
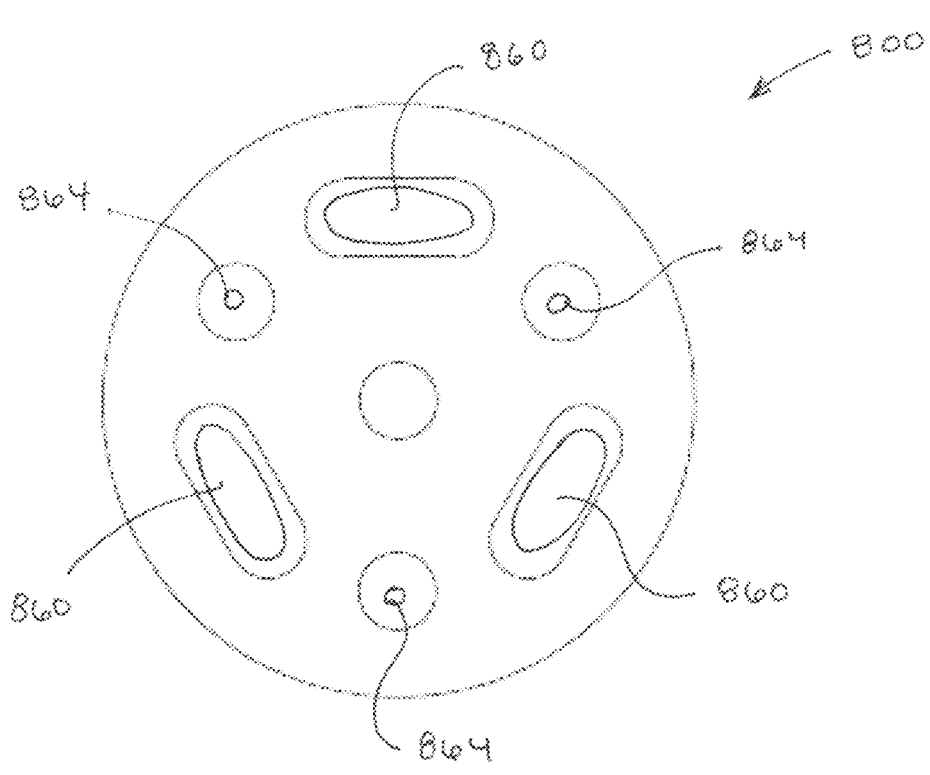
FIG. 28 is a cross section of yet another steerable electrode lead.

In yet another example, a microelectromechanical steering system may provide highly precise and controllable mechanisms for electrode lead steering. In one example shown in FIG. 28, miniaturized mechanical actuators 860 within the electrode lead 800 (e.g., embedded in polymeric material of the electrode lead). The MEMS actuators 860 may include microscale motors, actuators, or flexure mechanisms that can produce controlled mechanical movements when activated by electrical signals. These MEMS actuators 860 may be fabricated using semiconductor manufacturing techniques that enable the creation of complex mechanical structures with dimensions measured in micrometers. The MEMS actuators 860 may operate through various physical principles including electrostatic attraction, electromagnetic forces, or piezoelectric deformation to generate the mechanical forces needed for electrode lead positioning. The microscale nature of MEMS actuators 860 may allow for the integration of multiple actuators within a single electrode lead 800, enabling independent control of different lead segments or multiple degrees of freedom in positioning. In some cases, MEMS-based steering systems may incorporate position feedback sensors that provide real-time information about the current electrode position, enabling closed-loop control of the positioning process. The MEMS actuators 860 may be designed to operate at low power levels to minimize energy consumption and reduce heating effects within the surrounding tissue. The MEMS actuators 860 may be adjacent to the electrical conductors 864 embedded in the electrode lead 800.

Figure 29:
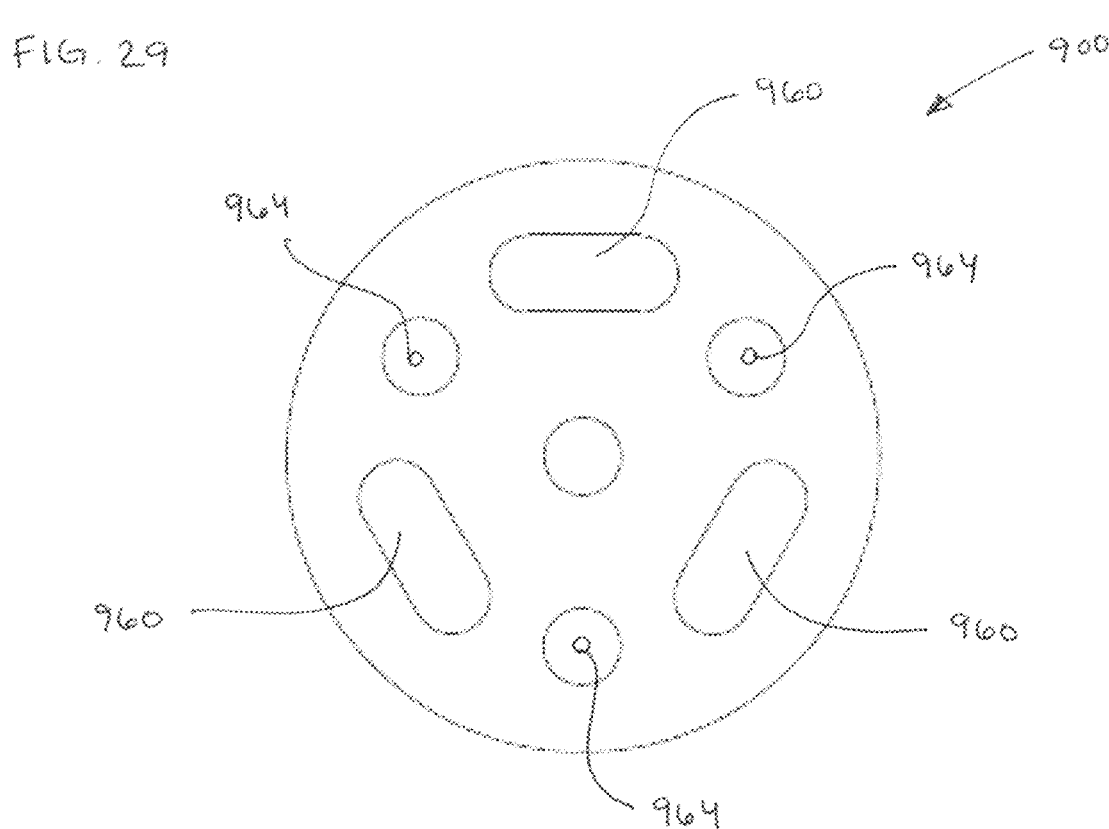
FIG. 29 is a cross section of another steerable electrode lead.

In another example, hydraulic and pneumatic actuation systems may provide additional options for steering the electrode lead. In the example shown in FIG. 29, expandable chambers 960 (broadly, expandable members or balloons) are disposed within or coupled to the electrode lead 900. The expandable members 960 may be spaced circumferentially about the electrode lead 900. Narrow channels or tubes in the electrode lead 900 allow controlled fluid transfer to the expandable members 960. Pressure changes within the hydraulic system may cause expansion or contraction of the expandable members 960 within or coupled to the electrode lead 900, resulting in controlled bending or positioning movements, including apposition forces against body structures. Pneumatic actuation may employ similar principles using compressible gases instead of liquids to create positioning forces. The hydraulic and pneumatic systems may be designed with multiple independent channels to enable complex positioning patterns. A suitable expandable member may be disclosed in U.S. Ser. No. 11/842,648, filed Aug. 21, 2007, the entirety of which is hereby incorporated by reference.

Overall, the steering lead mechanisms may enable optimization of electrode positioning relative to the SPG through systematic evaluation of stimulation effectiveness at different positions. Clinicians may activate the steering mechanisms to move the electrode contacts through a range of positions while monitoring patient responses or physiological feedback to identify the location that provides optimal therapeutic stimulation. The positioning optimization process may be guided by real-time impedance measurements that indicate the proximity of electrode contacts to neural tissue, with lower impedance values typically corresponding to closer electrode-tissue interfaces. In some cases, the optimization process may be automated through integration with artificial intelligence algorithms that can systematically evaluate different positions and identify optimal configurations based on predetermined criteria.

The steering functionality may provide particular benefits in cases where the SPG location varies from expected anatomical positions or when surgical access limitations prevent precise initial electrode placement. The ability to adjust electrode position after implantation may reduce the need for multiple electrode contacts along the lead, potentially allowing for smaller and less invasive implant designs. The steering mechanisms may also accommodate changes in anatomy over time due to tissue healing, scar formation, or other biological processes that might affect the optimal electrode positioning for therapeutic stimulation.

As set forth above, the hand-held controller 250 may provide energy delivery to implanted neuromodulation components through electromagnetic induction without requiring percutaneous connections or frequent surgical interventions for battery replacement. The power transfer mechanism may utilize inductive coupling between external power transmission coils and internal receiving coils integrated within the implanted device body (e.g., 200a, 300a). This wireless approach may eliminate the infection risks associated with transcutaneous leads while providing reliable power delivery for sustained neuromodulation therapy. Conventionally, the external power transmission system is configured with a single large inductive coil.

Figure 30:
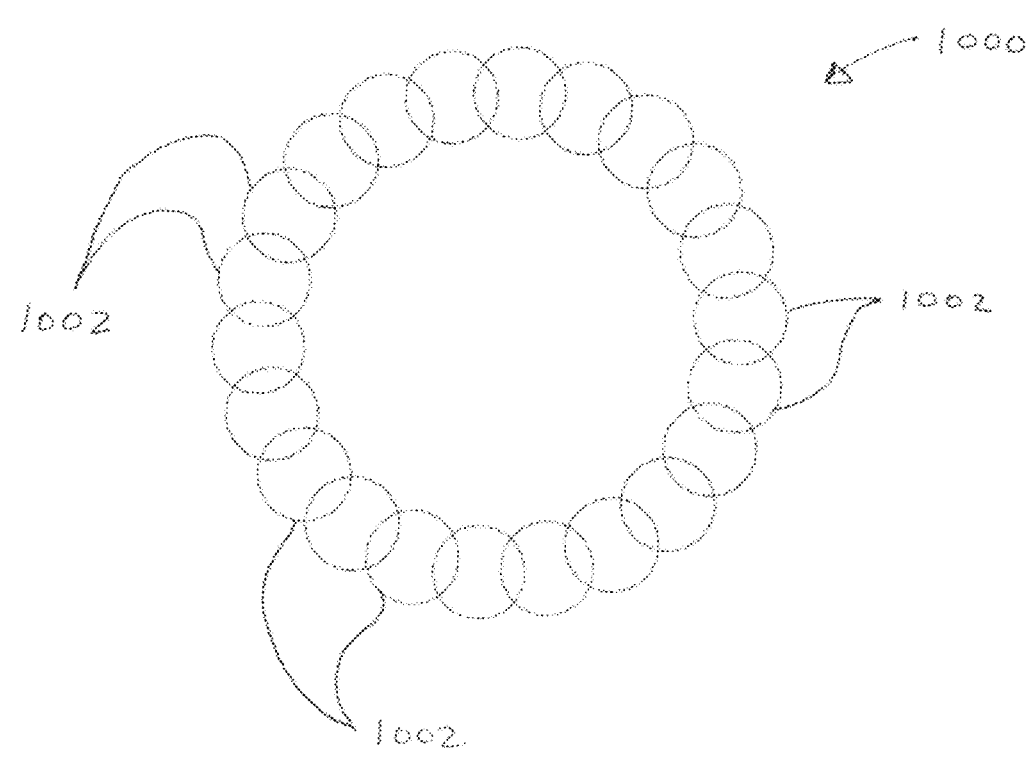
FIG. 30 is a schematic of an array of inductive coils for a hand-held controller or device.

Referring to FIG. 30, in another embodiment, a coil array 1000 utilizing multiple smaller overlapping coils 1002 may offer enhanced flexibility and power transfer optimization through selective coil activation and dynamic power routing compared to the single large inductive coil. The coil array 1000 may comprise a plurality of individual inductive elements 1002 (e.g., ring-shaped coils) arranged in overlapping patterns that provide redundant coverage across the target anatomical region. Each individual coil 1002 within the array 1000 may be independently controlled through dedicated drive electronics that can modulate power output, frequency, and phase relationships to optimize energy coupling with the receiving coil (not shown) in the body 300a of the electrode assembly or stimulator 300, for example. The smaller coil dimensions may allow for more precise spatial control of the electromagnetic field distribution, potentially reducing power dissipation in surrounding tissues while concentrating energy delivery to the implanted device.

The system may implement handshaking protocols to establish communication between the external power transmission system of the hand-held controller 250 and the implanted electrode assembly 200, 300, enabling dynamic optimization of power transfer parameters based on real-time coupling efficiency measurements. During the handshaking process, the external system may sequentially energize individual coils 1002 within the array 1000 while monitoring feedback signals from the electrode assembly 200, 300 to assess power transfer effectiveness. The electrode assembly 200, 300 may transmit telemetry data indicating received power levels, internal voltage measurements, or other performance metrics that allow the hand-held controller 250 to evaluate coupling quality for each coil position. This bidirectional communication may enable the identification of the coil 1002 or combination of coils that provides the most efficient energy transfer for the current implant position and orientation.

Power transfer efficiency optimization may be achieved through continuous monitoring and adjustment of transmission parameters based on the handshaking protocol results. The hand-held controller 250 may maintain a database of coil performance characteristics and automatically select the coil configuration that minimizes power consumption while meeting the energy requirements of the electrode assembly 200, 300. In some cases, multiple coils 1002 may be simultaneously activated with controlled phase relationships to create constructive interference patterns that enhance power coupling at the electrode assembly location. The system may also implement adaptive algorithms that adjust transmission frequency, amplitude, and duty cycle parameters to compensate for changes in tissue properties, implant positioning, or external interference sources.

The coil selection process may involve systematic evaluation of power transfer metrics across all available coil 1002 to identify optimal transmission configurations. The hand-held controller 250 may cycle through individual coils 1002 or coil combinations while measuring parameters such as power transfer efficiency, coil current levels, and thermal characteristics to determine the most effective power delivery approach. Feedback from the implanted device may include measurements of received power, battery charging rates, or internal temperature monitoring that provides additional data for optimizing the power transfer process. The handshaking protocol may be repeated periodically during treatment sessions to account for patient movement, changes in tissue hydration, or other factors that may affect electromagnetic coupling.

This embodiments including an array of coils 1002 may provide additional benefits through spatial diversity and fault tolerance capabilities that enhance system reliability and performance consistency. The overlapping coil arrangement may ensure that power delivery remains stable even if individual coils experience failures or degraded performance over time. The redundant coverage provided by multiple coils may also accommodate variations in patient positioning or movement during treatment sessions without interrupting power delivery to the implanted electrode assembly. In some cases, the array configuration may enable simultaneous power delivery and data communication through different coil elements, allowing for continuous telemetry monitoring while maintaining therapeutic stimulation protocols.

Figure 31:
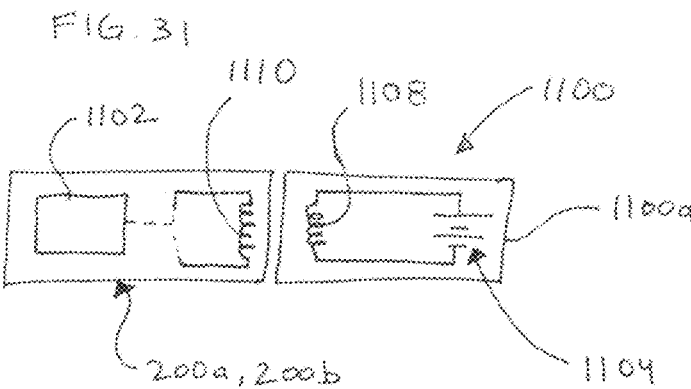
FIG. 31 is a schematic of a removable battery in electrical communication with and supplying power to an electrode assembly or stimulator.

Referring to FIG. 31, as an alternative or in addition to the external hand-held controller 250 being used to power the electrode assembly 350, a modular battery 1100 may be used to enable battery replacement or maintenance operations without compromising the hermetic integrity of the body 200a, 300a (or housing) of the electrode assembly 200, 300 (or other stimulator or electronic medical device). This modular approach may address one of the primary limitations of conventional implantable medical devices, where battery depletion typically necessitates complete device replacement through invasive surgical procedures. Thus, this modular battery 1100 may be applied to and incorporated in any suitable powered implantable medical device, therefore, the teachings set forth below are not necessarily limited to the electrode assembly 350 or other devices that include an electrode assembly. The modular battery 1100 may separate power storage components from the main electronic circuitry housed in the body 200a, 300a, allowing for selective access to power elements while maintaining the scaled, hermetic environment around sensitive electronic components 1102.

The battery 1100 may be housed within a separate hermetically sealed enclosure 1100 that maintains its own protective barrier against moisture, ionic contamination, and other environmental factors that could degrade battery performance or create safety hazards. The separate enclosure 1100 may be fabricated from biocompatible materials similar to those used for the body 200a, 200b, described above, including ceramic materials or metal alloys that provide corrosion resistance and mechanical protection for the enclosed battery cell(s) 1104. The modular battery 1100 and the main electronics 1102 within the body 200a, 300a of the electrode assembly 200, 300, for example, may be inductively coupled to provide electrical connection between the two without requiring direct electrical contacts that could compromise hermetic sealing. The inductive coupling system may comprise primary and secondary coils 1108, 1110, respectively, that enable wireless power transfer across the sealed boundaries of both the battery 1100 and the body 200a, 300a of the electrode assembly 200, 300. The primary coil 1108 may be integrated within the battery 1100, while the secondary coil 1110 may be positioned within the body 200a, 300a at a location that optimizes electromagnetic coupling when the battery 1100 is mechanically attached to the electrode assembly 200, 300, such as by a snap-fit connection, a magnetic connection, an adhesive, or in other ways. The inductive coupling approach may eliminate the need for feedthrough connections or removable electrical contacts that could create potential leak paths or mechanical failure points.

The mechanical attachment system between the battery 1100 and the electrode assembly 200, 300, or more particularly, the body 200a, 300a, may utilize reversible fastening mechanisms that allow for battery removal and replacement while maintaining proper alignment of the inductive coupling coils 1108, 1110 and without damaging or destroying the hermetic seal of the body 200a, 300a. The battery replacement procedure may involve minimally invasive surgical techniques that provide access to the battery 1100 without disturbing the body 200a, 300a or electrode lead position.

In addition to or as an alternative to one or more of the wireless powered and battery powered embodiments, energy harvesting may be used. These energy harvesting approaches may extend the operational lifetime of the electrode assembly 200, 300 or other medical device while reducing the frequency of battery replacement procedures, for example, and associated surgical interventions. The energy harvesting systems may operate continuously or intermittently depending on the availability of energy sources and the power requirements of the neuromodulation protocols. Examples of suitable energy harvesting systems include, but are not limited to, a piezoelectric energy harvesting system to convert mechanical energy from body movements, cardiovascular pulsations, or respiratory motions into electrical energy through the deformation of piezoelectric materials that generate electrical charges in response to applied mechanical stress; a thermoelectric energy harvesting system to utilize temperature differences between the implant location and surrounding tissues or between different anatomical regions to generate electrical power; Peltier heat pump systems to function, in reverse operation, as thermoelectric generators that produce electrical current when exposed to temperature gradients; triboelectric nanogenerators to harvest energy from mechanical friction or contact between different materials during body movement or tissue deformation; and/or biofuel cell energy harvesting systems to convert chemical energy from biological molecules into electrical energy through enzymatic or electrochemical reactions.

In one embodiment, the neuromodulation system may comprise a multi-level artificial intelligence integration architecture including three interconnected components that work in coordination to provide adaptive neuromodulation therapy: the electrode assembly 200, 300 with embedded processing capabilities, the hand-held controller 250, and a cloud-based processing system 255. Communication examples between the hand-held controller 250 and the cloud-based processing system 500 are shown in FIGS. 16-18. The electrode assembly or stimulator 200, 300 may house sensors (see FIG. 8) and localized processing units that continuously collect real-time physiological data including tissue impedance measurements, neural response signals, and biometric feedback parameters. This physiological data may be transmitted wirelessly to the hand-held controller 250 (or another controller or device) which may serve as an intermediary processing node between the electrode assembly and the cloud-based infrastructure 255. Alternatively, the electrode assembly 200, 300 may transmit the data directly to the cloud-based system 255. The cloud-based system 255 may host sophisticated machine learning algorithms that analyze aggregated data from multiple sources to optimize stimulation parameters and develop personalized treatment protocols for individual patients.

Figure 32:
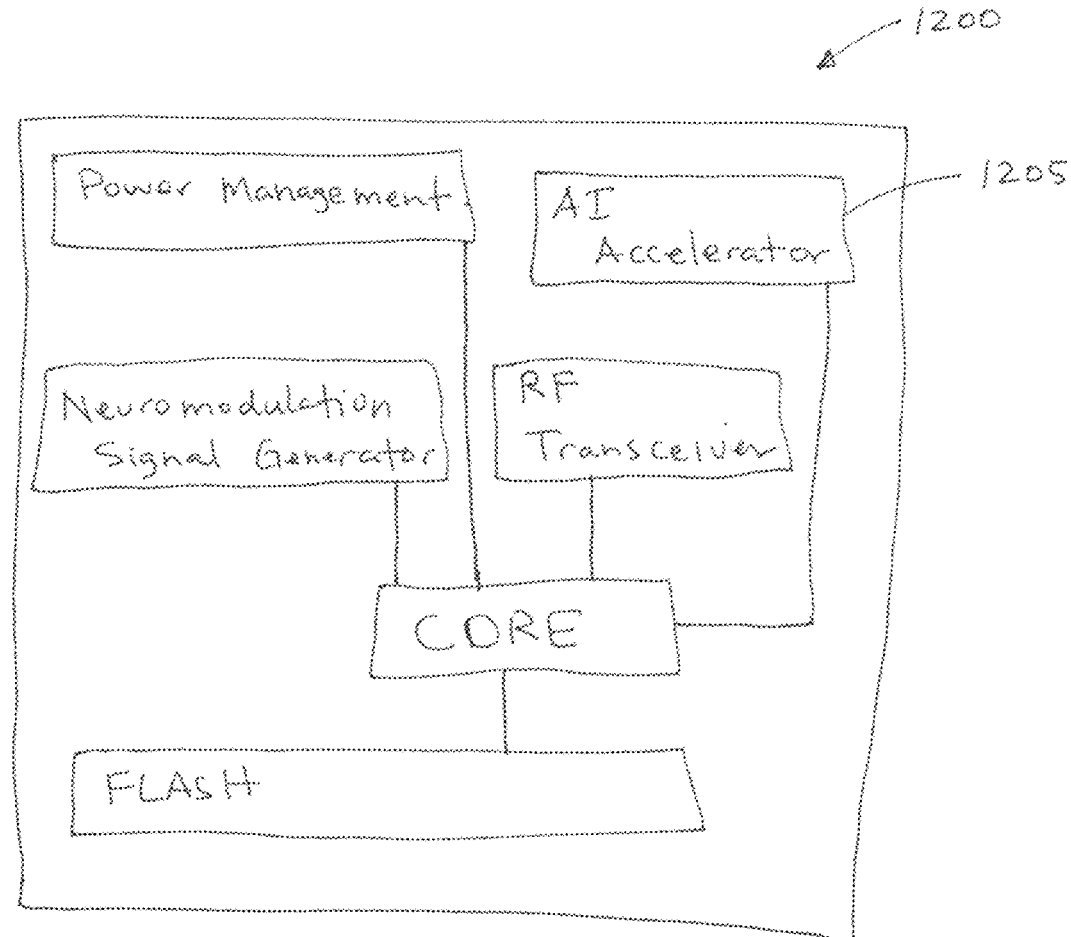
FIG. 32 is a diagram of an ASIC for use with a stimulation system.

The electrode assembly 200, 300 may incorporate artificial intelligence functionality through embedded processing units that enable ultra-low latency real-time adjustments and closed-loop control of stimulation parameters. Machine learning algorithms implemented at the electrode assembly level may utilize technologies such as tinyML frameworks operating on application-specific integrated circuits (ASICS), enabling localized processing of neural and biological signals with minimal power consumption. A schematic of a suitable ASIC 1200 is illustrated in FIG. 32. The embedded processing capabilities may include pre-trained lightweight neural networks, decision tree algorithms, or neuromorphic computing architectures that can classify bio-responses such as blinking, tearing, or other reflexive actions in real-time. These classification algorithms may differentiate between reflexive and pathological responses, enabling more targeted interventions and confirming sphenopalatine ganglion activation during stimulation protocols.

The electrode assembly 200, 300 may implement on-chip data compression and feature extraction algorithms that process physiological signals to identify meaningful bio-markers while reducing power consumption and data transmission requirements. Real-time tissue impedance measurements, nerve response characteristics, and biometric feedback including heart rate variability, blood pressure variations, or electroencephalography signals may be analyzed through embedded machine learning models to provide immediate stimulation adjustments. The localized artificial intelligence capabilities (e.g., AI accelerator 1205) may enable dynamic or adaptive stimulation protocols that respond to changing physiological conditions without requiring communication delays associated with external processing systems. In some cases, the electrode assembly 200, 300 may detect early indications of therapeutic need, such as physiological markers associated with cluster headache onset, and automatically initiate treatment cycles or alert patients through the interface of the handheld controller 250.

In another embodiment, the handheld controller 250 or other computing device (e.g., smart device, such as a smart phone or tablet) may serve as an intermediate processing platform that coordinates data flow between the electrode assembly 200, 300 and cloud-based systems 255 while providing localized artificial intelligence capabilities for patient interaction and treatment management. Machine learning algorithms implemented within the handheld controller 250 may focus on electrode configuration optimization, paresthesia mapping, and session parameter adjustment based on patient-reported feedback and real-time biometric data. The handheld controller 250 may utilize edge machine learning chips or mobile processors running specialized frameworks such as TensorFlow Lite models to provide responsive processing capabilities without requiring continuous cloud connectivity. Artificial intelligence algorithms within the handheld controller 250 may recommend optimal electrode configurations after analyzing initial patient feedback or may provide automated test stimulation protocols to identify the most effective stimulation parameters.

The handheld controller 250 or other hand-held computing device may implement conversational large language model capabilities that operate in offline or cloud-connected modes to assist clinicians in fine-tuning therapy protocols and guide patients through treatment or titration procedures. These language model implementations may utilize lightweight architectures such as LLM-Lite or other compressed language models that can operate within the computational constraints of portable medical devices. The handheld controller may also incorporate pain prediction or forecast models that analyze patient logs, heart rate variability data, and information from connected wearable devices to provide prophylactic treatment recommendations. Session parameters may be continuously adjusted based on patient-reported outcomes, biometric data trends, and historical treatment effectiveness patterns stored within the handheld controller memory systems.

Communication protocols between the handheld controller 250 and electrode assembly 200, 300 may utilize secure Bluetooth Low Energy or WiFi connections that enable real-time data exchange while maintaining patient privacy and data security. The handheld controller may also establish wireless communication links with cloud-based processing systems when network connectivity is available, enabling synchronization of treatment data and algorithm updates. Power management algorithms within the handheld controller 250 may coordinate the operation of different artificial intelligence processing modules to optimize battery life while maintaining responsive user interaction and continuous monitoring capabilities.

Cloud-based processing systems 255 may provide large-scale data analysis, predictive modeling capabilities, and comprehensive clinical decision support through advanced machine learning algorithms that operate on aggregated patient data from multiple sources. The cloud infrastructure may implement patient-specific model training using historical stimulation settings, sensor feedback data, and clinical outcomes to create digital twin representations of individual patient responses to neuromodulation therapy. These digital twin models may incorporate physiological parameters, treatment history, and environmental factors to predict optimal stimulation protocols for specific clinical scenarios or patient conditions. Machine learning pipelines implemented in cloud environments may utilize frameworks such as PyTorch, TensorFlow, or XGBoost to process large datasets and identify patterns that may not be apparent through localized processing alone.

Large language model integration within cloud-based systems may provide clinical assistant capabilities that analyze treatment logs, suggest parameter modifications, and interpret patient feedback to support clinical decision-making processes. The cloud-based artificial intelligence may also enable automatic paresthesia mapping and electrode configuration optimization through probabilistic modeling approaches that consider anatomical variations, tissue properties, and individual patient response characteristics. Research and product development applications may benefit from cloud-based analysis of anonymized treatment data to identify trends, optimize device performance, and develop improved stimulation protocols for future patients.

Federated learning implementations may allow patient data to remain decentralized while still contributing to model training and algorithm improvement processes, enhancing patient privacy and data security compared to centralized data collection approaches. Application programming interfaces may integrate real-world data from wearable devices, electronic medical records, and other health monitoring systems to provide comprehensive patient profiles that inform treatment optimization algorithms. The cloud-based system may also coordinate software updates and algorithm improvements that can be distributed to electrode assemblies and handheld controllers to enhance system performance over time without requiring hardware modifications.

The machine learning algorithms implemented across the multi-level architecture may focus on optimization of stimulation parameters through adaptive learning techniques that continuously refine treatment protocols based on patient responses and physiological feedback. Supervised learning algorithms may be trained using historical patient data to predict optimal amplitude, pulse width, and frequency parameters based on individual patient characteristics and treatment objectives. Unsupervised learning approaches may identify previously unknown patterns in patient response data that can inform the development of new stimulation protocols or reveal biomarkers associated with treatment effectiveness. Reinforcement learning algorithms may enable the system to learn optimal stimulation strategies through trial-and-error approaches that systematically evaluate different parameter combinations and adapt based on observed outcomes.

Closed-loop feedback control may be achieved through machine learning models that process real-time sensor data to provide immediate adjustments to stimulation parameters based on physiological responses or changing patient conditions. The feedback control algorithms may incorporate multiple input sources including tissue impedance measurements, neural response signals, cardiovascular parameters, and patient-reported symptoms to create comprehensive control strategies that maintain therapeutic effectiveness while minimizing adverse effects. Predictive algorithms may anticipate changes in patient condition or treatment needs based on historical patterns and environmental factors, enabling proactive adjustments to stimulation protocols before symptoms or physiological changes become apparent.

Personalized treatment protocols may be developed through machine learning analysis of patient-specific data including treatment history, physiological characteristics, genetic factors, and lifestyle parameters that influence treatment response. The personalization algorithms may consider factors such as time of day, activity levels, sleep patterns, environmental conditions, and concurrent medications to optimize stimulation timing and parameters for individual patients. Machine learning models may also account for disease progression, anatomical changes, or other temporal factors that may affect treatment effectiveness over extended periods, enabling long-term adaptation of therapy protocols to maintain optimal outcomes throughout the course of treatment.

The electrode assembly, or other neuromodulation device for the SPG, may be implanted through various surgical approaches that provide access to the SPG region while accommodating different anatomical considerations and clinical requirements. These surgical methodologies may be selected based on patient-specific anatomical variations, surgeon preference, and the particular clinical objectives of the neuromodulation therapy. Below are descriptions of non-conventional surgical approaches.

Figure 33:
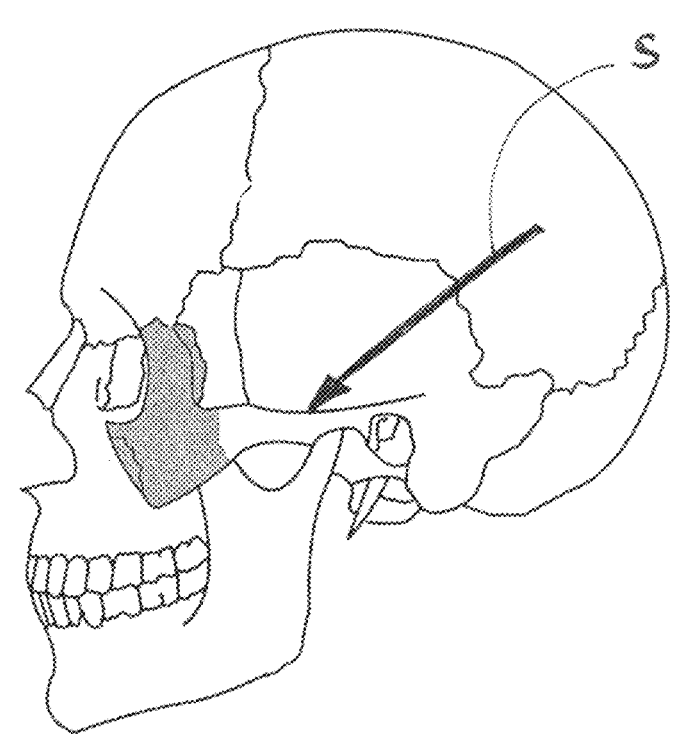
FIG. 33 is a side view of skeletal structure of a human head showing a surgical approach for delivering an electrode lead to the SPG.

Referring to FIG. 33, a suprazygomatic surgical approach may enable electrode lead placement adjacent or at the SPG through a pathway that extends above the zygomatic arch, potentially offering a more direct route to the sphenopalatine ganglion compared to inferior approaches. The direction of this approach is indicated by arrow S. This methodology may involve creating a surgical corridor that bypasses the complex anatomical structures of the infratemporal fossa, potentially reducing the overall surgical time and complexity associated with electrode lead routing. The suprazygomatic approach may accommodate linear electrode lead configurations that follow a more direct path to the target location, potentially allowing for shorter electrode leads and reduced implant volume. This approach may provide advantages in patients with anatomical variations that complicate inferior access routes or in cases where previous surgical interventions have altered the normal anatomical relationships in the infratemporal region.

Figure 34:
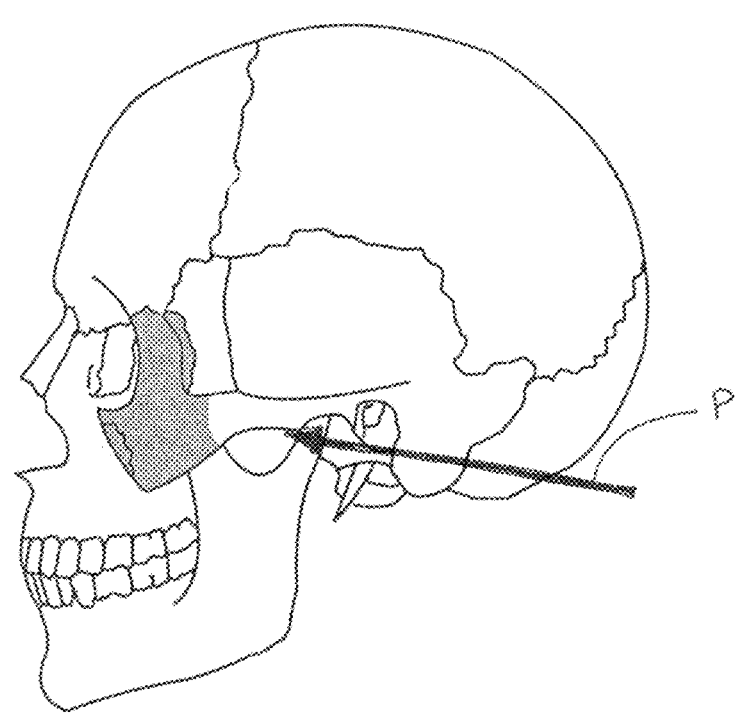
FIG. 34 is a side view of skeletal structure of a human head showing another surgical approach for delivering an electrode lead to the SPG.

Referring to FIG. 34, a posterior surgical approach may enable electrode lead placement adjacent or at the SPG through a pathway that extends behind the mandible and around the posterior aspect of the maxilla, creating an alternative route that avoids both the oral cavity and the traditional zygomatic approaches. The direction of this approach is indicated by arrow P. This methodology may offer advantages in terms of cosmetic outcomes by utilizing incision locations that align with natural skin creases and anatomical contours, potentially reducing the visibility of surgical scars and improving patient satisfaction with the aesthetic results. The posterior approach may also reduce the risk of infection complications by avoiding the oral cavity environment, which contains numerous bacterial species that could potentially contaminate the surgical site or implanted components. The pathway may accommodate curved electrode lead designs that follow the anatomical contours while maintaining appropriate positioning relative to the sphenopalatine ganglion target location.

Drill hole access methods may provide alternative surgical approaches that involve creating controlled bone perforations through or around the zygomatic process to establish direct pathways for electrode placement. These drill hole techniques may utilize precision surgical instruments and computer navigation systems to create bone channels with specific dimensions and orientations that accommodate the electrode lead while minimizing damage to surrounding anatomical structures. The drill hole approach may enable more direct electrode routing compared to soft tissue dissection methods, potentially reducing surgical time and tissue trauma associated with extensive anatomical exposure. Computer-guided drilling techniques may enhance the precision of bone channel creation, allowing for accurate targeting of the sphenopalatine ganglion region while avoiding critical structures such as nerve pathways, blood vessels, and adjacent anatomical spaces. Disclosure of computer navigation that may be used with the computer-guided drilling is disclosed in U.S. Ser. No. 15/299,981, filed Oct. 21, 2016, the entirety of which is hereby incorporated by reference.

The drill hole methodology may incorporate magnetic guidance systems that assist in directing the electrode lead through the created bone channels toward the target location with enhanced accuracy. These magnetic guidance approaches may utilize external magnetic field generators positioned around the surgical site to influence the trajectory of magnetically responsive electrode components during the insertion process. The combination of precision bone drilling and magnetic guidance may enable minimally invasive electrode placement procedures that reduce the extent of soft tissue dissection while maintaining accurate positioning relative to the sphenopalatine ganglion. Post-drilling procedures may involve scaling the bone channels with biocompatible materials or bone cement to prevent fluid ingress and maintain the structural integrity of the surrounding bone tissue. Suitable magnetic guidance may be disclosed in U.S. Ser. No. 12/134,083, the entirety of which is hereby incorporated by reference.

Each surgical approach may be selected based on individual patient characteristics including anatomical variations, previous surgical history, and specific clinical indications that influence the optimal electrode placement strategy. Preoperative imaging studies may guide the selection of the most appropriate surgical approach by providing detailed visualization of anatomical structures, tissue densities, and spatial relationships that affect electrode lead routing and positioning. Intraoperative navigation systems may enhance the precision of electrode placement regardless of the chosen surgical approach, providing real-time feedback regarding electrode position relative to target anatomical landmarks and surrounding critical structures. The surgical approach selection may also consider factors such as patient comfort, recovery time, and long-term maintenance requirements that influence the overall treatment experience and clinical outcomes.

One or more inventions of the present disclosure may be described in the following numbered paragraphs:

1. A method for controlling permeability of a blood-brain barrier of a subject, comprising:

monitoring, using one or more sensors, physiological parameters of the subject;

analyzing, using artificial intelligence algorithms, the monitored physiological parameters to determine optimal stimulation parameters for modulating the blood-brain barrier;

applying, based on the determined optimal stimulation parameters, electrical stimulation to a sphenopalatine ganglion of the subject to increase porosity of the blood-brain barrier;

delivering an active agent to the subject, wherein the active agent crosses the blood-brain barrier due to the increased porosity;

monitoring, using the one or more sensors, a parameter indicating concentration of the active agent; and applying, based on analysis of the monitored parameter by the artificial intelligence algorithms, electrical stimulation to the sphenopalatine ganglion to decrease porosity of the blood-brain barrier.

2. The method of paragraph 1, wherein the physiological parameters comprise at least one of heart rate variability, blood pressure, electroencephalography signals, tissue impedance measurements, or neural response characteristics.

3. The method of paragraph 1, wherein the artificial intelligence algorithms comprise machine learning algorithms that analyze historical treatment data to identify parameter combinations that provide optimal therapeutic outcomes for the subject.

4. The method of paragraph 3, wherein the machine learning algorithms utilize at least one of supervised learning, unsupervised learning, or reinforcement learning techniques.

5. The method of paragraph 1, wherein the electrical stimulation to increase porosity comprises a frequency of from about 10 Hz to about 60 Hz and a biphasic waveform.

6. The method of paragraph 5, wherein the electrical stimulation to decrease porosity comprises a frequency of from about 60 Hz to about 200 Hz and a biphasic waveform.

7. The method of paragraph 1, wherein the active agent is selected from the group consisting of monoclonal antibodies, chemotherapy agents, enzymes, proteins, stem cells, and combinations thereof.

8. A neuromodulation system for modulating permeability of a blood-brain barrier, comprising:

an electrode assembly configured to be implanted adjacent to a sphenopalatine ganglion of a subject and configured to deliver electrical stimulation thereto;

one or more sensors configured to monitor physiological parameters of the subject and parameters indicating active agent concentration;

a processor configured to execute artificial intelligence algorithms; and a memory storing computer-readable instructions that, when executed by the processor, cause the processor to:

analyze the monitored physiological parameters using the artificial intelligence algorithms to determine optimal stimulation parameters;

control the electrode assembly to apply electrical stimulation based on the determined optimal stimulation parameters to increase porosity of the blood-brain barrier;

monitor parameters indicating active agent concentration using the one or more sensors; and control the electrode assembly to apply electrical stimulation to decrease porosity of the blood-brain barrier based on analysis of the monitored parameters by the artificial intelligence algorithms.

9. The neuromodulation system of paragraph 8, wherein the electrode assembly comprises a plurality of electrodes configured in at least one of cylindrical, oval, or single-sided geometries.

10. The neuromodulation system of paragraph 9, wherein the electrodes comprise surface modifications comprises at least one of microfabrication, plasma etching, electrochemical deposition, or abrasive treatments to create roughened surfaces that enhance electrochemical surface area.

11. The neuromodulation system of paragraph 8, wherein the one or more sensors are configured to monitor physiological parameters comprising at least one of heart rate variability, blood pressure, electroencephalography signals, tissue impedance measurements, neural response characteristics, or transendothelial electrical resistance.

12. The neuromodulation system of paragraph 8, wherein the artificial intelligence algorithms comprise machine learning algorithms comprising at least one of supervised learning algorithms, unsupervised learning algorithms, or reinforcement learning algorithms.

13. The neuromodulation system of paragraph 12, wherein the machine learning algorithms are configured to analyze historical treatment data to identify parameter combinations that provide optimal therapeutic outcomes for individual patients.

14. The neuromodulation system of paragraph 8, further comprising a wireless power transfer system configured to provide energy to the electrode assembly through electromagnetic induction, wherein the wireless power transfer system comprises an array of overlapping coils configured to optimize power transfer efficiency through selective coil activation.

15. A computer-implemented method for analyzing sensor data to control blood-brain barrier permeability, comprising:

receiving, from one or more sensors, physiological data from a subject;

processing the physiological data using machine learning algorithms to identify patterns associated with optimal blood-brain barrier modulation;

generating, based on the identified patterns, personalized stimulation parameters for electrical stimulation of a sphenopalatine ganglion;

transmitting the personalized stimulation parameters to a stimulation device;

receiving, from the one or more sensors, data indicating active agent concentration in the subject;

analyzing the active agent concentration data using the machine learning algorithms; and generating, based on the analysis, control signals for modulating the electrical stimulation to adjust porosity of the blood-brain barrier.

16. The computer-implemented method of paragraph 15, wherein the physiological data comprises at least one of heart rate variability, blood pressure, electroencephalography signals, tissue impedance measurements, or neural response characteristics.

17. The computer-implemented method of paragraph 16, wherein the machine learning algorithms comprise at least one of supervised learning algorithms, unsupervised learning algorithms, or reinforcement learning algorithms.

18. The computer-implemented method of paragraph 17, wherein the supervised learning algorithms are trained using historical patient data to predict optimal amplitude, pulse width, or frequency parameters based on individual patient characteristics.

19. The computer-implemented method of paragraph 15, wherein the personalized stimulation parameters comprise frequency parameters of from about 10 Hz to about 60 Hz for increasing porosity of the blood-brain barrier and frequency parameters of from about 60 Hz to about 200 Hz for decreasing porosity of the blood-brain barrier.

20. The computer-implemented method of paragraph 15, wherein the active agent concentration data comprises measurements of at least one of active agent concentration at the blood-brain barrier, change in active agent concentration in brain tissue, or change in concentration of a substance from brain tissue in blood of the subject.

One or more inventions of the present disclosure may be described in the following numbered paragraphs:

1. A method for controlling permeability of a blood-brain barrier of a subject, comprising:

monitoring, using one or more sensors, physiological parameters of the subject;

analyzing, using artificial intelligence algorithms, the monitored physiological parameters to determine optimal stimulation parameters for modulating the blood-brain barrier;

applying, based on the determined optimal stimulation parameters, electrical stimulation to a sphenopalatine ganglion of the subject to increase porosity of the blood-brain barrier;

delivering an active agent to the subject, wherein the active agent crosses the blood-brain barrier due to the increased porosity;

monitoring, using the one or more sensors, a parameter indicating concentration of the active agent; and applying, based on analysis of the monitored parameter by the artificial intelligence algorithms, electrical stimulation to the sphenopalatine ganglion to decrease porosity of the blood-brain barrier.

2. The method of paragraph 1, wherein the physiological parameters comprise at least one of heart rate variability, blood pressure, electroencephalography signals, tissue impedance measurements, or neural response characteristics.

3. The method of paragraph 1, wherein the artificial intelligence algorithms comprise machine learning algorithms that analyze historical treatment data to identify parameter combinations that provide optimal therapeutic outcomes for the subject.

4. The method of paragraph 3, wherein the machine learning algorithms utilize at least one of supervised learning, unsupervised learning, or reinforcement learning techniques.

5. The method of paragraph 1, wherein the electrical stimulation to increase porosity comprises a frequency of from about 10 Hz to about 60 Hz and a biphasic waveform.

6. The method of paragraph 5, wherein the electrical stimulation to decrease porosity comprises a frequency of from about 60 Hz to about 200 Hz and a biphasic waveform.

7. The method of paragraph 1, wherein the active agent is selected from the group consisting of monoclonal antibodies, chemotherapy agents, enzymes, proteins, stem cells, and combinations thereof.

8. A neuromodulation system for modulating permeability of a blood-brain barrier, comprising:

an electrode assembly configured to be implanted adjacent to a sphenopalatine ganglion of a subject and configured to deliver electrical stimulation thereto;

one or more sensors configured to monitor physiological parameters of the subject and parameters indicating active agent concentration;

a processor configured to execute artificial intelligence algorithms; and a memory storing computer-readable instructions that, when executed by the processor, cause the processor to:

analyze the monitored physiological parameters using the artificial intelligence algorithms to determine optimal stimulation parameters;

control the electrode assembly to apply electrical stimulation based on the determined optimal stimulation parameters to increase porosity of the blood-brain barrier;

monitor parameters indicating active agent concentration using the one or more sensors; and control the electrode assembly to apply electrical stimulation to decrease porosity of the blood-brain barrier based on analysis of the monitored parameters by the artificial intelligence algorithms.

9. The neuromodulation system of paragraph 8, wherein the electrode assembly comprises a plurality of electrodes configured in at least one of cylindrical, oval, or single-sided geometries.

10. The neuromodulation system of paragraph 9, wherein the electrodes comprise surface modifications comprises at least one of microfabrication, plasma etching, electrochemical deposition, or abrasive treatments to create roughened surfaces that enhance electrochemical surface area.

11. The neuromodulation system of paragraph 8, wherein the one or more sensors are configured to monitor physiological parameters comprising at least one of heart rate variability, blood pressure, electroencephalography signals, tissue impedance measurements, neural response characteristics, or transendothelial electrical resistance.

12. The neuromodulation system of paragraph 8, wherein the artificial intelligence algorithms comprise machine learning algorithms comprising at least one of supervised learning algorithms, unsupervised learning algorithms, or reinforcement learning algorithms.

13. The neuromodulation system of paragraph 12, wherein the machine learning algorithms are configured to analyze historical treatment data to identify parameter combinations that provide optimal therapeutic outcomes for individual patients.

14. The neuromodulation system of paragraph 8, further comprising a wireless power transfer system configured to provide energy to the electrode assembly through electromagnetic induction, wherein the wireless power transfer system comprises an array of overlapping coils configured to optimize power transfer efficiency through selective coil activation.

15. A computer-implemented method for analyzing sensor data to control blood-brain barrier permeability, comprising:

receiving, from one or more sensors, physiological data from a subject;

processing the physiological data using machine learning algorithms to identify patterns associated with optimal blood-brain barrier modulation;

generating, based on the identified patterns, personalized stimulation parameters for electrical stimulation of a sphenopalatine ganglion;

transmitting the personalized stimulation parameters to a stimulation device;

receiving, from the one or more sensors, data indicating active agent concentration in the subject;

analyzing the active agent concentration data using the machine learning algorithms; and generating, based on the analysis, control signals for modulating the electrical stimulation to adjust porosity of the blood-brain barrier.

16. The computer-implemented method of paragraph 15, wherein the physiological data comprises at least one of heart rate variability, blood pressure, electroencephalography signals, tissue impedance measurements, or neural response characteristics.

17. The computer-implemented method of paragraph 16, wherein the machine learning algorithms comprise at least one of supervised learning algorithms, unsupervised learning algorithms, or reinforcement learning algorithms.

18. The computer-implemented method of paragraph 17, wherein the supervised learning algorithms are trained using historical patient data to predict optimal amplitude, pulse width, or frequency parameters based on individual patient characteristics.

19. The computer-implemented method of paragraph 15, wherein the personalized stimulation parameters comprise frequency parameters of from about 10 Hz to about 60 Hz for increasing porosity of the blood-brain barrier and frequency parameters of from about 60 Hz to about 200 Hz for decreasing porosity of the blood-brain barrier.

20. The computer-implemented method of paragraph 15, wherein the active agent concentration data comprises measurements of at least one of active agent concentration at the blood-brain barrier, change in active agent concentration in brain tissue, and change in concentration of a substance from brain tissue in blood of the subject.

One or more inventions of the present disclosure may be described in the following numbered paragraphs:

1. A method for controlling permeability of a blood-brain barrier of a subject, comprising:

monitoring, using one or more sensors, physiological signals from the subject to identify biomarkers indicative of blood-brain barrier status;

processing the physiological signals using artificial intelligence algorithms to determine when to modulate the blood-brain barrier;

applying electrical stimulation to a sphenopalatine ganglion of the subject to increase porosity of the blood-brain barrier based on the determination; and applying electrical stimulation to the sphenopalatine ganglion of the subject to decrease porosity of the blood-brain barrier based on the determination.

2. The method of paragraph 1, wherein the physiological signals comprise at least one of heart rate variability, blood pressure, electroencephalography signals, tissue impedance measurements, neural response signals, or biometric feedback.

3. The method of paragraph 1, wherein the artificial intelligence algorithms comprise machine learning algorithms that analyze the physiological signals to identify patterns associated with blood-brain barrier permeability changes.

4. The method of paragraph 3, wherein the machine learning algorithms comprise at least one of supervised learning algorithms, unsupervised learning algorithms, and reinforcement learning algorithms.

5. The method of paragraph 1, wherein applying electrical stimulation to increase porosity comprises delivering electrical stimulation at a frequency of about 10 Hz to about 60 Hz.

6. The method of paragraph 1, wherein applying electrical stimulation to decrease porosity comprises delivering electrical stimulation at a frequency of about 60 Hz to about 200 Hz.

7. The method of paragraph 5, wherein the electrical stimulation comprises a biphasic waveform with charge-balanced pulses.

8. A system for modulating blood-brain barrier permeability, comprising:

one or more sensors configured to monitor physiological signals from a subject to identify biomarkers;

an electrode assembly configured to deliver electrical stimulation to a sphenopalatine ganglion of the subject;

a processor configured to execute artificial intelligence algorithms to analyze the physiological signals and determine when to open or close the blood-brain barrier; and a controller configured to control the electrode assembly to selectively increase or decrease porosity of the blood-brain barrier based on the determination from the processor.

9. The system of paragraph 8, wherein the one or more sensors comprise at least one of heart rate variability sensors, blood pressure sensors, electroencephalography sensors, tissue impedance sensors, neural response sensors, or biometric feedback sensors.

10. The system of paragraph 8, wherein the electrode assembly comprises one or more electrodes configured to be implanted adjacent to the sphenopalatine ganglion.

11. The system of paragraph 10, wherein the one or more electrodes comprise surface modifications to increase electrochemical surface area for charge injection.

12. The system of paragraph 11, wherein the surface modifications comprise roughened surfaces created by at least one of microfabrication, plasma etching, electrochemical deposition, or abrasive treatments.

13. The system of paragraph 8, wherein the artificial intelligence algorithms comprise machine learning algorithms configured to analyze physiological signals to identify patterns associated with blood-brain barrier permeability changes.

14. The system of paragraph 13, wherein the machine learning algorithms comprise at least one of supervised learning algorithms, unsupervised learning algorithms, or reinforcement learning algorithms configured to optimize stimulation parameters based on patient responses.

15. A computer-implemented method for analyzing sensor data to control blood-brain barrier modulation, comprising:

receiving physiological signal data from one or more sensors monitoring a subject;

processing the physiological signal data using machine learning algorithms to identify biomarkers indicative of blood-brain barrier status;

determining, based on the identified biomarkers, optimal timing for opening the blood-brain barrier;

determining, based on the identified biomarkers, optimal timing for closing the blood-brain barrier; and generating control signals for an electrode assembly to modulate electrical stimulation of a sphenopalatine ganglion based on the determined timing.

16. The computer-implemented method of paragraph 15, wherein the physiological signal data comprises at least one of heart rate variability, blood pressure, electroencephalography signals, tissue impedance measurements, neural response signals, or biometric feedback.

17. The computer-implemented method of paragraph 16, wherein the machine learning algorithms comprise at least one of supervised learning algorithms, unsupervised learning algorithms, or reinforcement learning algorithms.

18. The computer-implemented method of paragraph 17, wherein the supervised learning algorithms are trained using historical patient data to predict optimal stimulation parameters based on individual patient characteristics.

19. The computer-implemented method of paragraph 15, wherein generating control signals comprises determining stimulation frequency parameters, wherein opening the blood-brain barrier uses frequencies of about 10 Hz to about 60 Hz and closing the blood-brain barrier uses frequencies of about 60 Hz to about 200 Hz.

20. The computer-implemented method of paragraph 19, wherein the control signals specify biphasic waveforms with charge-balanced pulses for the electrical stimulation.

One or more inventions of the present disclosure may be described in the following numbered paragraphs:

1. An electrode assembly for neural body stimulation, comprising:

an electrode body configured to house micro-electronics;

an electrode lead extending from the electrode body and including at least one electrode having a surface with texture modifications to increase effective electrochemical surface area available for charge injection at a neural body to be stimulated, wherein the texture modifications comprise roughened topographies that facilitate improved ionic conduction and energy coupling.

2. The electrode assembly of paragraph 1, wherein the at least one electrode is fabricated from a biocompatible conductive material comprising at least one of platinum, iridium oxide, or titanium nitride.

3. The electrode assembly of paragraph 2, wherein the biocompatible conductive material has high charge-injection capacity and stability in neural environments.

4. The electrode assembly of paragraph 1, wherein the texture modifications are created through a process comprising at least one of microfabrication, plasma etching, electrochemical deposition, or abrasive treatments.

5. The electrode assembly of paragraph 4, wherein the microfabrication process includes photolithography to create controlled surface features with dimensions ranging from nanometer to micrometer scales.

6. The electrode assembly of paragraph 1, wherein the at least one electrode has a geometry selected from the group consisting of cylindrical, oval, or single-sided configurations to accommodate anatomical variations of a sphenopalatine ganglion region.

7. The electrode assembly of paragraph 1, further comprising a fixation apparatus configured to anchor the electrode assembly adjacent the neural body, wherein the fixation apparatus comprises suture anchors configured to enable flexible attachment to soft tissue structures including fascia, muscle tissue, or periosteal layers.

8. A neuromodulation system for affecting porosity of a blood-brain barrier, comprising:

an electrode assembly including an electrode body and an electrode lead with electrodes having surface modifications created through microfabrication techniques to enhance charge injection efficiency;

a controller configured to deliver electrical stimulation through the electrodes to a sphenopalatine ganglion; and wherein the surface modifications comprise surface features with dimensions ranging from nanometer to micrometer scales to reduce impedance at target frequency ranges.

9. The neuromodulation system of paragraph 8, wherein the electrodes are fabricated from a biocompatible conductive material comprising at least one of platinum, iridium oxide, or titanium nitride.

10. The neuromodulation system of paragraph 9, wherein the biocompatible conductive material has high charge-injection capacity and stability in neural environments.

11. The neuromodulation system of paragraph 8, wherein the microfabrication techniques include photolithography, electron beam lithography, or focused ion beam milling to create the controlled surface features.

12. The neuromodulation system of paragraph 8, wherein the surface modifications further comprise roughened topographies created through plasma etching using reactive ion etching processes.

13. The neuromodulation system of paragraph 12, wherein plasma etching parameters including gas composition, pressure, or power levels are adjusted to achieve desired surface roughness characteristics and feature geometries.

14. The neuromodulation system of paragraph 8, wherein the controller is configured to deliver charge-balanced biphasic pulses in frequency ranges of approximately 10-100 Hz to prevent irreversible electrochemical reactions while achieving desired permeability changes in the blood-brain barrier.

Other inventions of the present disclosure may be described above.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. A method for controlling permeability of a blood-brain barrier in a subject, comprising:

measuring a predetermined parameter using a sensor to determine when an active agent is available in the subject for passing through the blood-brain barrier;

applying a first electrical stimulation to a sphenopalatine ganglion of the subject at a first frequency to selectively increase a porosity of the blood-brain barrier when the predetermined parameter indicates the active agent is available;

monitoring a physiological response of the subject; and applying a second electrical stimulation to the sphenopalatine ganglion of the subject at a second frequency different than the first frequency to selectively decrease the porosity of the blood-brain barrier based on the monitored physiological response.

2. The method of claim 1, wherein the predetermined parameter comprises at least one of time elapsed, delivered active agent dosage, active agent concentration in the body, change in active agent concentration, or change of concentration of a substance in blood of the patient indicating that the substance has passed through the blood-brain barrier.

3. The method of claim 1, wherein the electrical stimulation to increase porosity comprises a frequency of 10 Hz to 40 Hz and a current of 0.1 to 3 mA.

4. The method of claim 3, wherein the electrical stimulation to decrease porosity comprises a frequency of 60 Hz to 200 Hz and a current of 0.1 to 3 mA.

5. The method of claim 1, wherein the electrical stimulation comprises a biphasic, charge-balanced waveform.

6. The method of claim 5, wherein the biphasic waveform is amplitude modulated with a sinusoidal frequency.

7. The method of claim 1, wherein the physiological response comprises transendothelial electrical resistance measurements to determine blood-brain barrier integrity.

8. A system for modulating blood-brain barrier permeability of a subject, comprising:

an electrode assembly configured to deliver electrical stimulation to a sphenopalatine ganglion of the subject;

a sensor configured to monitor a predetermined parameter related to an active agent concentration in the subject; and a controller, including a processor, configured to:

execute a machine learning algorithm to analyze sensor data received from the sensor and determine optimal stimulation parameters for the electrode assembly; and automatically adjust the electrical stimulation delivered by the electrode assembly based on the optimal stimulation parameters determined by the machine learning algorithm analysis to selectively increase and decrease porosity of the blood-brain barrier.

9. The system of claim 8, wherein the electrode assembly comprises an electrode body positioned medial to a zygoma on a posterior maxilla within a buccal fat pad of a cheek, and an electrode lead positioned within a pterygopalatine fossa in proximity to the sphenopalatine ganglion.

10. The system of claim 9, wherein the electrode assembly further comprises a fixation apparatus configured to anchor to a zygomaticomaxillary buttress.

11. The system of claim 8, wherein the sensor is configured to monitor a parameter comprising at least one of time elapsed, delivered active agent dosage, active agent concentration in the body, change in active agent concentration, or change of concentration of a substance in blood of the patient indicating that the substance has passed through the blood-brain barrier.

12. The system of claim 11, wherein the controller is configured to automatically initiate electrical stimulation at a frequency of 10 Hz to 40 Hz to increase porosity of the blood-brain barrier when the predetermined parameter indicates an active agent is available for passing through the blood-brain barrier.

13. The system of claim 12, wherein the controller is further configured to automatically adjust the electrical stimulation to a frequency of 60 Hz to 200 Hz to decrease porosity of the blood-brain barrier based on the machine learning algorithm analysis of the sensor data.

14. A computer-implemented method for optimizing blood-brain barrier modulation of a subject using artificial intelligence, comprising:

receiving sensor data indicating a physiological parameter of the subject;

processing the sensor data using a machine learning algorithm to predict a stimulation parameter for increasing a permeability of the blood-brain barrier;

generating a first control signal for an electrode assembly based on the predicted stimulation parameter to increase the permeability of the blood-brain barrier;

analyzing real-time feedback data from a feedback sensor to determine when to decrease the permeability of the blood-brain barrier; and generating a second control signal for the electrode assembly based on the analysis of the real-time feedback data to decrease the permeability of the blood-brain barrier.

15. The computer-implemented method of claim 14, wherein the machine learning algorithms comprise supervised learning algorithms trained using historical patient data to predict optimal amplitude, pulse width, or frequency parameters.

16. The computer-implemented method of claim 15, wherein the machine learning algorithms further comprise reinforcement learning algorithms that systematically evaluate different parameter combinations and adapt based on observed outcomes.

17. The computer-implemented method of claim 14, wherein the physiological parameters comprise tissue impedance measurements, neural response signals, heart rate variability, blood pressure variations, or electroencephalography signals.

18. The computer-implemented method of claim 17, wherein analyzing the real-time feedback data comprises processing transendothelial electrical resistance measurements to determine blood-brain barrier integrity.

19. The computer-implemented method of claim 14, wherein the control signals comprise biphasic, charge-balanced waveforms with frequencies of 10 Hz to 40 Hz for opening the blood-brain barrier and frequencies of 60 Hz to 200 Hz for closing the blood-brain barrier.

20. The computer-implemented method of claim 19, wherein the biphasic waveforms are amplitude modulated with a sinusoidal frequency and the machine learning algorithms automatically adjust at least one of pulse width modulation, frequency modulation, or amplitude modulation to optimize blood-brain barrier permeability.

* * * * *

68